US011174518B2

(12) United States Patent
You et al.

(10) Patent No.: US 11,174,518 B2
(45) Date of Patent: Nov. 16, 2021

(54) METHOD OF CLASSIFYING AND DIAGNOSING CANCER

(71) Applicant: Cedars-Sinai Medical Center, Los Angeles, CA (US)

(72) Inventors: Sungyong You, Los Angeles, CA (US); Michael Freeman, West Hollywood, CA (US); Jayoung Kim, Beverly Hills, CA (US); Beatrice Knudsen, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 496 days.

(21) Appl. No.: 15/764,185

(22) PCT Filed: Oct. 5, 2016

(86) PCT No.: PCT/US2016/055573
§ 371 (c)(1),
(2) Date: Mar. 28, 2018

(87) PCT Pub. No.: WO2017/062505
PCT Pub. Date: Apr. 13, 2017

(65) Prior Publication Data
US 2018/0282817 A1    Oct. 4, 2018

Related U.S. Application Data

(60) Provisional application No. 62/237,354, filed on Oct. 5, 2015.

(51) Int. Cl.
| | | |
|---|---|---|
| *C12Q 1/6886* | (2018.01) | |
| *G16B 25/00* | (2019.01) | |
| *G16B 20/00* | (2019.01) | |
| *A61K 33/243* | (2019.01) | |
| *G16B 20/20* | (2019.01) | |
| *G16B 25/10* | (2019.01) | |
| *A61K 31/337* | (2006.01) | |
| *A61K 31/4166* | (2006.01) | |
| *A61K 31/506* | (2006.01) | |

(52) U.S. Cl.
CPC .......... *C12Q 1/6886* (2013.01); *A61K 31/337* (2013.01); *A61K 31/4166* (2013.01); *A61K 31/506* (2013.01); *A61K 33/243* (2019.01); *G16B 20/00* (2019.02); *G16B 20/20* (2019.02); *G16B 25/00* (2019.02); *G16B 25/10* (2019.02); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 9,631,239 B2* | 4/2017 | Perou | .......... C12Q 1/6886 |
| 10,527,624 B2* | 1/2020 | Dittamore | ........ G01N 33/57434 |
| 2011/0165566 A1 | 7/2011 | Wittliff et al. | |
| 2013/0281312 A1 | 10/2013 | Richardson et al. | |
| 2014/0235479 A1 | 8/2014 | Depinho et al. | |
| 2014/0243433 A1 | 8/2014 | Li et al. | |
| 2014/0308202 A1 | 10/2014 | Matusik et al. | |
| 2014/0342924 A1 | 11/2014 | Harkin et al. | |
| 2015/0100244 A1 | 4/2015 | Hannum | |
| 2016/0312294 A1* | 10/2016 | Walker | ........ A61P 13/08 |

FOREIGN PATENT DOCUMENTS

| | | |
|---|---|---|
| CA | 2996426 A1 | 4/2017 |
| EP | 0430402 A2 | 6/1991 |
| EP | 3359692 A1 | 8/2018 |
| WO | 2007/114896 A2 | 10/2007 |
| WO | 2008086342 A2 | 7/2008 |
| WO | 2012/135008 A1 | 10/2012 |
| WO | 2013/116144 A1 | 8/2013 |
| WO | 2015065919 A1 | 5/2015 |
| WO | 2017062505 | 4/2017 |

OTHER PUBLICATIONS

Lapointe et al. Gene expression profiling identifies clinically relevant subtypes of prostate cancer. PNAS,2004;101(3):811-816 (Year: 2004).*
Logothetis et al. Molecular Classifi cation of Prostate Cancer Progression: Foundation for Marker-Driven Treatment of Prostate Caner.Cancer Discov;2013;3(8): 849-861. (Year: 2013).*
Logothetis et al. Molecular Classification of Prostate Cancer Progression: Foundation for Marker-Driven Treatment of Prostate Cancer. Cancer Discov; 2013; 3(8); 849-861. (Year: 2013).*
Herbst and Khuri. Mode of action of docetaxel—a basis for combination with novel anticancer agents. Cancer Treatment Reviews 2003; 29: 407-415. (Year: 2003).*
Affymetrix U133 Plus 2 array, PDF attachment, retried from internet on Oct. 5, 2020.p. 1-15. (Year: 2014).*
International Search Report and Written Opinion for PCT/US2016/055573 dated Feb. 27, 2017, 26 pages.
Bolstad et al., A comparison of normalization methods for high density oligonucleotide array data based on variance and bias. Bioinformatics, 2003, 19, pp. 185-193.
You et al., A Systems Approach to Rheumatoid Arthritis, PLoS One, 2012, 7(12): e51508, p. 1-11.
Albertson, Localization of the ribosomal genes in Caenorhabditis elegans chromosomes by in situ hybridization using biotin-labeled probes, The EMBO Journal, 1984, 3(6), pp. 1227-1234.

(Continued)

*Primary Examiner* — Jehanne S Sitton
*Assistant Examiner* — Wahwah T Johnson
(74) *Attorney, Agent, or Firm* — Linda B. Huber; Nixon Peabody LLP

(57) ABSTRACT

The invention provides various methods for classifying prostate cancers into subtypes. The classification methods may be used to diagnose or prognose prostate cancers. In one embodiment, the subtypes are PCS1, PCS2, or PCS3. In one embodiment, the PCS1 subtype is most likely to progress to metastatic disease or prostate cancer specific mortality when compared to the PCS2 subtype or PCS3 subtype. In one embodiment, the PCS1 subtype is resistant to enzalutamide.

16 Claims, 21 Drawing Sheets

(56) References Cited

OTHER PUBLICATIONS

Pinkel et al., Fluorescence in situ hybridization with human chromosome-specific libraries: Detection of trisomy 21 and translocations of chromosome 4, Proc. Natl. Acad. Sci. USA, 1988, 85, pp. 9138-9142.
Kallioniemi et al., ERBB2 amplification in breast cancer analyzed by fluorescence in situ hybridization, Proc. Nat. Acad. Sci. USA, 1992, 89, pp. 5321-5325.
Ginzinger et al., Measurement of DNA Copy Number at Microsatellite Loci Using Quantitative PCR Analysis, Cancel Research, 2000, 60, pp. 5405-5409.
Kwoh et al., Transcription-based amplification system and detection of amplified human immunodeficiency virus type 1 with a bead-based sandwich hybridization format, PNAS, 1989, 86, pp. 1173-1177.
Guatelli et al., Isothermal, in vitro amplification of nucleic acids by a multienzyme reaction modeled after retoviral replication, PNAS, 1990, 87, pp. 1874-1878.
Shabalin et al., Merging two gene-expression studies via cross-platform normalization, Bioinformatics, 2008, 24(9), pp. 1154-1160.
Piccolo et al., A single-sample microarray normaliztion method to facilitate personalized-medicine workflows, Genomics, 2012, 100, pp. 337-344.
Levine et al., Pathway and gene-set activation measurement form mRNA expression data: the tissue distribution of human pathways, Genome Biology, 2006, 7(10), R93, 17 pages.
Carrasco et al., High-resolution genomic profiles define distinct clinico-pathogenetic subgroups of multiple myeloma patients. Cancer Cell, 2006, 9, pp. 313-325.
Brunet et al., Metagenes and molecular pattern discovery using matrix factorization, PNAS, 2004, 101(12), pp. 4164-4169.
Storey, A direct approach to false discovery rates, J.R. Statist. Soc. B, 2002, 64, pp. 479-498.
Markert et al., Molecular classification of prostate cancer using curated expression signatures, PNAS, 2011, 108(52), pp. 21276-21281.
Drier et al., Pathway-based personalized analysis of cancer, PNAS, 2013, 110(16), pp. 6388-6393.
Tomlins et al., Distinct classes of chromosomal rearrangements create oncogenic ETS gene fusions in prostate cancer, Nature, 2007, 448, pp. 595-599.
Singh et al., Gene expression correlates of clinical prostate cancer behavior, Cancer Cell, 2002, 1, pp. 203-209.
Lapointe et al., Gene expression profiling indentifies clinically relevant subtypes of prostate cancer, PNAS, 2004, 101(3), pp. 811-816.
Taylor et al., Integrative Genomic Profiling of Human Prostate Cancer, Cancer Cell, 2010, 18, pp. 11-22.
Stuart et al., In silico dissection of cell-type-associated patterns of gene expression in prostate cancer, PNAS, 2014, 101(2), pp. 615-620.
Aytes et al., Cross-Species Regulatory Network Analysis Identifies a Synergistic Interaction between FOXM1 and CENPF that Drives Prostate Cancer Malignancy, Cancer Cell, 2014, 25, pp. 638-651.
Mulholland et al., Pten Loss and RAS/MAPK Activation Cooperate to Promote EMT and Metastasis Initiated from Prostate Cancer Stem/Progenitor Cells, Cancer Research, 2012, 72(7), pp. 1878-1889.
Erho et al., Discovery and Validation of a Prostate Cancer Genomic Classifier that Predicts Early Metastasis Following Radical Prostatectomy, PLoS ONE 2013, 8(6), e66855, pp. 1-12.

The Cancer Genome Atlas Research Network, The Molecular Taxonomy of Primary Prostate Cancer, Cell, 2015, 163, pp. 1011-1025.
Robinson et al., Integrative Clinical Genomics of Advanced Prostate Cancer, Cell, 2015, 161, pp. 1251-1228.
Baird et al., Membrane hyperpolarization cyclic nucleotide levels and relaxation in the guinea-pig internal anal sphincter, Br. J. Pharmacol., 1990,100, pp. 329-335.
Visvader, Keeping abreast of the mammary epithelial hierarchy and breast tumorigenesis. Genes & Development, 2009, 23, pp. 2563-2577.
Liu et al., Differential Gene Expression Profiling of Functionally and Developmentally Distinct Human Prostate Epithelial Populations, The Prostate, 2015, 75, pp. 764-776.
Smith et al., A basal stem cell signature identifies aggressive prostate cancer phenotypes, PNAS, 2015, E6544-E6552, 9 pages.
Morrison et al., Nanoliter high throughput quantitative PCR, Nucleic Acids Research, 2006, 34(18), e123, p. 1-9.
Pinkel et al., High resolution analysis of DNA copy number variation using comparative genomic hybridization to microarrays. Nature Genetics, 1998, 20, 207-211.
Gatza et al., An integrated genomics approach identifies drivers of proliferation in luminal subtype human breast cancer. Nature Genetics, 2014, 46(10), 1051-1059.
Grasso et al., The mutational landscape of lethal castration-resistant prostate cancer. Nature, 2012, 487, 239-243.
Tomlins et al., Characterization of 1577 Primary Prostate Cancers Reveals Novel Biological and Clinicopathologic Insights into Molecular Subtypes. European Urology, 2015, 68(4), 555-567.
Barretina et al., The Cancer Cell Line Encyclopedia enables predictive modelling of anticancer drug sensitivity. Nature, 2012, 483, 603-607.
Goldstein et al., Identification of a Cell of Origin for Human Prostate Cancer. Science, 2010, 329(5991), 568-571.
Wang et al., Lineage analysis of basal epithelial cells reveals their unexpected plasticity and supports a cell-of-origin model for prostate cancer heterogeneity Nature Cell Biology, 2013, 15, 274-283.
Miyamoto et al., RNA-Seq of single prostate CTCs implicates noncanonical Wnt signaling in antiandrogen resistance. Science, 2015, 349(6254), 1351-1356.
Geiss et al., Direct multiplexed measurement of gene expression with color-coded probe pairs. Nature Biotechnology, 2008, 26, 317-325.
Martin et al., Prognostic Determinants in Prostate Cancer. Cancer J., 2011, 17(6), 429-437.
EP 16854250.4 European Extended Search Report dated Apr. 1, 2019, 10 pages.
Melling et al., Overexpression of Enhancer of Zeste Homolog 2 (EZH2) Characterizes an Aggressive Subset of Prostate Cancers and Predicts Patient Prognosis Independently from Pre- and Postperatively assessed Clinicopathological parameters, Carcinogenesis, 2015, vol. 36(11), pp. 1333-1340.
Van Leenders et al., Polycomb-Group Oncogenes EZH2, BMI1, and RING1 are Overexpressed in Prostate Cancer with Adverse Pathologic and Clinical Features, European Urology, 2007, vol. 52(2), pp. 455-463.
You et al., Integrated Classification of Prostate Cancer Reveals a Novel Luminal Subtype with Poor Outcome, Cancer Research, 2016, vol. 76(17), pp. 4948-4958.
International Preliminary Report on Patentability for PCT/US2016/055573 dated Apr. 19, 2018, 17 pages.
Jan et al., A Circulating Tumor Cell-RNA Assay for Assessment of Adrogen Receptor Signaling Inhibitor Sensitivity in Metastatic Castration-Resistant Prostate Cancer, Theranostics, 2019, vol. 9(10), pp. 2812-2826.

\* cited by examiner

| Disease status | Number of samples | Sample composition |
|---|---|---|
| Benign | 794 | Benign prostate tissue |
| GS < 7 | 328 | Primary PC with Gleason sum < 7 |
| GS = 7 | 530 | Primary PC with Gleason sum = 7 |
| GS > 7 | 203 | Primary PC with Gleason sum > 7 |
| CRPC/Met | 260 | metastatic or castration-resistant PC |

Non-CRPC/Met     CRPC/Met

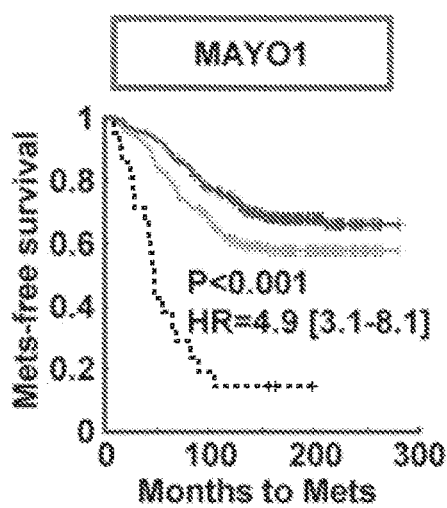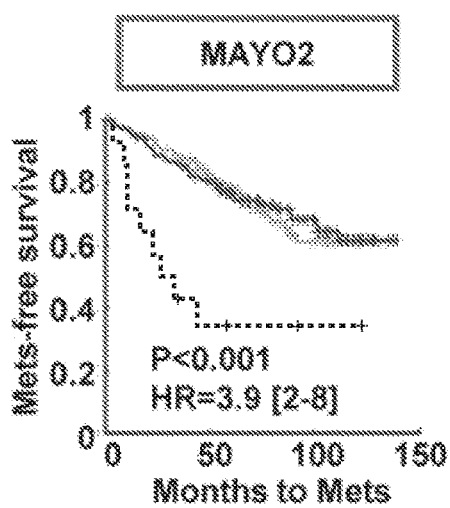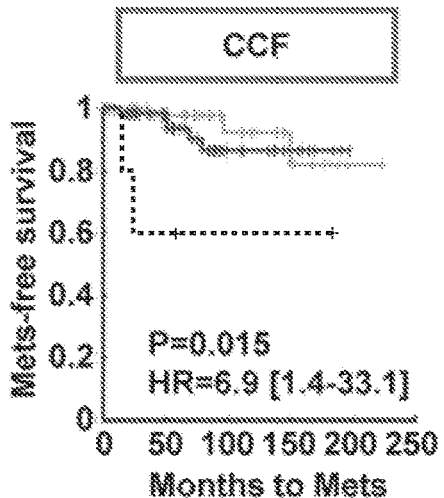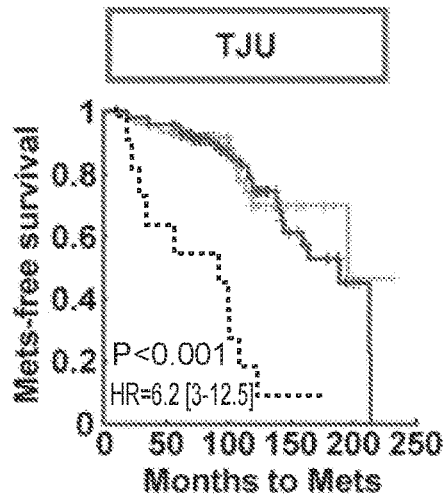

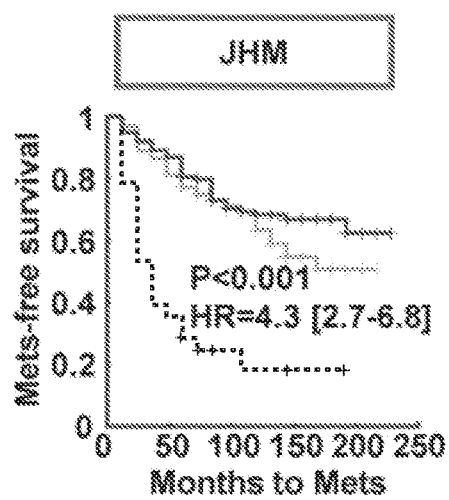
FIG. 3H(v)
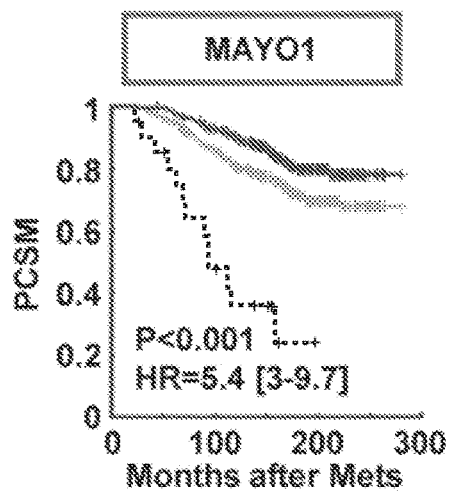
FIG. 3H(vi)
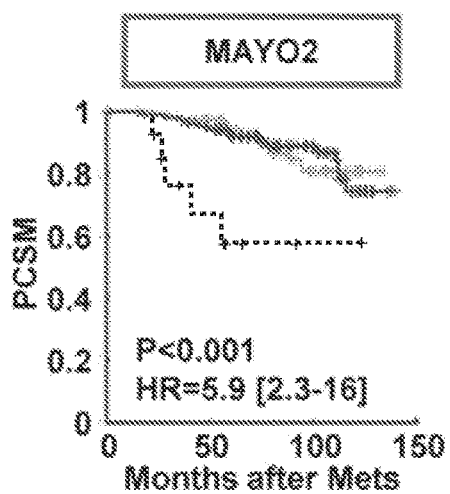
FIG. 3H(vii)
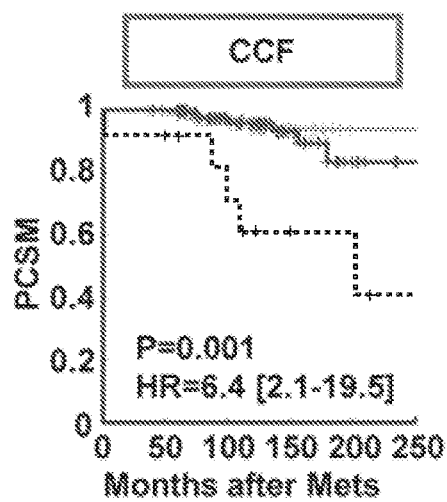
FIG. 3H(viii)

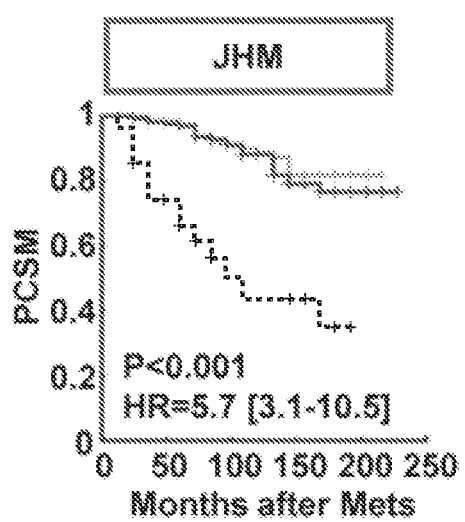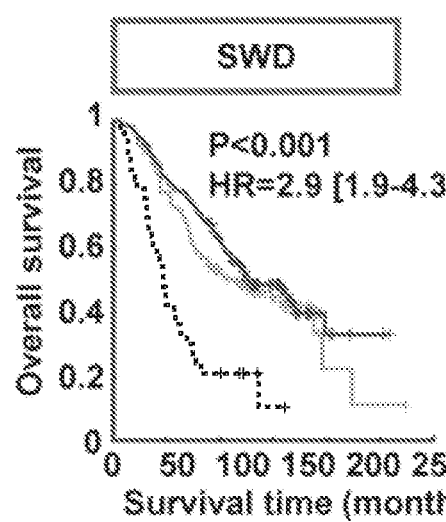

| | Term | P |
|---|---|---|
| SEG1 | Chromosome organization | <0.001 |
| SEG1 | Cell proliferation | <0.001 |
| SEG1 | DNA repair | 0.001 |
| SEG2 | Lipid biosynthetic process | 0.008 |
| SEG2 | Steriod biosynthetic process | 0.022 |
| SEG3 | Extracellular matrix organization | <0.001 |
| SEG3 | inflammatory response | <0.001 |
| SEG3 | cell migration | 0.003 |

METHOD OF CLASSIFYING AND DIAGNOSING CANCER

CROSS-REFERENCE TO RELATED APPLICATIONS

This application is a National Phase of International Application No. PCT/US2016/055573, filed Oct. 5, 2016, which designated the U.S. and that International Application was published under PCT Article 21(2) in English. This application claims priority under 35 U.S.C. § 119(e) to U.S. Provisional Application No. 62/237,354, filed Oct. 5, 2015, the contents of which are herein incorporated by reference in their entirety.

STATEMENT REGARDING FEDERALLY SPONSORED RESEARCH OR DEVELOPMENT

This invention was made with government support under Grant Nos. DK087806, CA143777, and CA098912 awarded by National Institutes of Health and under Grant No. W81XWH-14-1-0152 awarded by the Department of Defense. The government has certain rights in the invention.

FIELD OF THE INVENTION

The invention relates to medicine and oncology, for example, methods, compositions and kits for classifying cancers and methods, compositions and kits for treating cancers.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Prostate cancer (PC) is a heterogeneous disease. Currently defined molecular subtypes are based on gene translocations, gene expression, mutations, and oncogenic signatures. In other cancer types, such as breast cancer, molecular classifications predict survival and are routinely used to guide treatment decisions. However, the heterogeneous nature of prostate cancer, and the relative paucity of redundant genomic alterations that drive progression, or that can be used to assess likely response to therapy, have hindered attempts to develop a classification system with clinical relevance.

Recently, molecular lesions in aggressive prostate cancer have been identified. For example, overexpression of the androgen receptor (AR) due to gene amplification has been observed in castration-resistant prostate cancer (CRPC). Presence of AR variants (AR-V) that do not require ligand for activation have been reported in a large percentage of CRPCs and have been correlated with resistance to AR-targeted therapy. The oncogenic function of enhancer of zeste homolog 2 (EZH2) was found in cells of CRPC, and recurrent mutations in the speckle-type POZ protein (SPOP) gene occur in approximately 15% of prostate cancers. Expression signatures related to these molecular lesions have also been developed to predict patient outcomes. While, in principle, signature-based approaches could be used independently in small cohorts, there is a potential for an increase in diagnostic or prognostic accuracy if signatures reflecting gene expression perturbations relevant to prostate cancer could be applied to large cohorts containing thousands of clinical specimens.

Here we present the results of an integrated analysis of an unprecedentedly large set of transcriptome data, including from over 4,600 clinical prostate cancer specimens. This study revealed that RNA expression data can be used to categorize prostate cancer tumors into 3 distinct subtypes, based on molecular pathway representation encompassing molecular lesions and cellular features related to prostate cancer biology. Application of this sub-typing scheme to 10 independent cohorts and a wide range of preclinical prostate cancer models strongly suggest that the subtypes we define originate from inherent differences in prostate cancer origins and/or biological features. We provide evidence that this novel prostate cancer classification scheme can be useful for detection of aggressive tumors using tissue as well as blood from patients with progressing disease. It also provides a starting point for development of subtype-specific treatment strategies and companion diagnostics As such, for an informed clinical decision, there still exists a great need for methods, compositions and kits that can categorize/classify/stratify/subtype PC and methods, compositions and kits that can treat PC.

SUMMARY OF THE INVENTION

The following embodiments and aspects thereof are described and illustrated in conjunction with compositions, methods, systems, and kits which are meant to be exemplary and illustrative, not limiting in scope.

Various embodiments of the present invention provide a method for classifying prostate cancer into subtypes, comprising: a) obtaining a sample from a subject; b) assaying the sample to detect changes in gene expression of one or more genes relative to reference samples or values; c) determining the presence of an expression pattern of the one or more genes associated with the subtype in the sample based on the detected changes; and d) classifying the cancer in the subject into the subtype if the expression pattern of the one or more genes associated with the subtype is detected in the sample. In some embodiments, the subtype is PCS1, PCS2, or PCS3. In some embodiments, the one or more genes comprise one, two, three, four, five, six, or more, or all of the genes listed in Table 1. In some embodiments, the genes are STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45. In some embodiments, the one or more genes comprise one, two, three, four, five, six, or more, or all of STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45. In some embodiments, the sample is a tissue sample or blood. In some embodiments, the sample is a prostate tissue or blood circulating tumor cells. In some embodiments, the blood circulating tumor cells are classified into the PCS1 subtype. In some embodiments, the PCS1 subtype is resistant to enzalutamide. In some embodiments, the PCS1 subtype is characterized in that it has an increased probability of progressing to metastatic disease or prostate cancer specific mortality when compared to the PCS2 subtype or PCS3 subtype. In some embodiments, wherein the PCS1 subtype has increased expression levels in STMN1, MCM4, CCNB1, CDC6, CDKN3, EZH2, TPX2, FOXM1, KIF11, HMMR, MKI67, and KNTC1 genes; and decreased expression levels in RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45 genes. In some embodiments, the PCS2 subtype has increased expression levels in RAB3B, SLC4A4, ANK3, GJB1, and SLC12A2 genes; and decreased expression levels in STMN1, MCM4, CCNB1, CDC6, CDKN3, EZH2, TPX2, FOXM1, KIF11, HMMR, MKI67, KNTC1, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45 genes. In some embodiments, the PCS3 subtype has increased expression levels in CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45 genes; and decreased expression levels in STMN1, MCM4, CCNB1, CDC6, CDKN3, EZH2, TPX2, FOXM1, KIF11, HMMR, MKI67, KNTC1, RAB3B, SLC4A4, ANK3, GJB1, and SLC12A2 genes. In some embodiments, the subtype is PCS1, and the method further comprises administering to the subject a therapeutically effective amount of one or more DNA damaging agents selected from cisplatin, PARP inhibitors, or combinations thereof. In some embodiments, the subtype is PCS2, and the method further comprises administering to the subject a therapeutically effective amount of an antiandrogen, an androgen receptor (AR) antagonist, a selective AR modulator, an androgen synthesis inhibitor, enzalutamide, a mitotic inhibitor, or docetaxel, or combinations thereof. In some embodiments, the subtype is PCS3, and the method further comprises administering to the subject a therapeutically effective amount of dasatinib or docetaxel, or combinations thereof.

Various embodiments of the present invention provide a method for prognosing a cancer in a subject, comprising: a) obtaining a sample from the subject; b) assaying the sample to detect changes of expression levels of one or more genes relative to reference samples or values; c) determining the presence of a subtype's expression pattern of the one or more genes in the sample based on the detected changes; and d) prognosing the cancer in the subject. In some embodiments, the subtype is PCS1, and the cancer is prognosed with a poor clinical outcome. In some embodiments, the poor clinical outcome comprises lower metastasis-free survival, higher risk of metastatic progression, higher rate of cancer specific mortality, lower overall survival, or more aggressive form of cancer, or a combination thereof.

Various embodiments of the present invention provide a method for treating, preventing, reducing the likelihood of having, reducing the severity of and/or slowing the progression of a cancer in a subject, comprising: a) obtaining a sample from the subject; b) assaying the sample to detect changes of expression levels of one or more genes relative to reference samples or values; c) determining the presence of a subtype's expression pattern of the one or more genes in the sample based on the detected changes; and d) administering a therapeutically effective amount of a therapeutic agent to the subject, thereby treating, preventing, reducing the likelihood of having, reducing the severity of and/or slowing the progression of the cancer. In some embodiments, the subtype is PCS1, and the administered therapeutic agent is one or more DNA damaging agents selected from cisplatin, PARP inhibitors, or combinations thereof. In some embodiments, the subtype is PCS1, and the administered therapeutic agent is a mitotic inhibitor. In some embodiments, the subtype is PCS1, and the administered therapeutic agent is docetaxel, or a functional equivalent, analog, derivative or salt of docetaxel, or a combination thereof. In some embodiments, the subtype is PCS2, and the administered therapeutic agent is an antiandrogen, an androgen receptor (AR) antagonist, a selective AR modulator, or an androgen synthesis inhibitor, or a combination thereof. In some embodiments, the subtype is PCS2, and the administered therapeutic agent is enzalutamide, or a functional equivalent, analog, derivative or salt of enzalutamide, or a combination thereof. In some embodiments, the subtype is PCS2, and the administered therapeutic agent is a mitotic inhibitor. In some embodiments, the subtype is PCS2, and the administered therapeutic agent is docetaxel, or a functional equivalent, analog, derivative or salt of docetaxel, or a combination thereof. In some embodiments, the subtype is PCS3, and the administered therapeutic agent is a Src signaling inhibitor, a Src family tyrosine kinase inhibitor, or a Bcr-Abl tyrosine kinase inhibitor, or a combination thereof. In some embodiments, the subtype is PCS3, and the administered therapeutic agent is dasatinib, or a functional equivalent, analog, derivative or salt of dasatinib, or a combination thereof. In some embodiments, the subtype is PCS3 and the administered therapeutic agent is docetaxel, or a functional equivalent, analog, derivative or salt of docetaxel, or a combination thereof.

Various embodiments of the present invention provide a method for treating, preventing, reducing the likelihood of having, reducing the severity of and/or slowing the progression of a cancer in a subject, comprising: a) obtaining a sample from the subject; b) assaying the sample to detect a marker for a subtype of the cancer; c) detecting the marker for the subtype in the sample; and d) administering a therapeutically effective amount of a therapeutic agent to the subject, thereby treating, preventing, reducing the likelihood of having, reducing the severity of and/or slowing the progression of the cancer. In some embodiments, the marker for the subtype comprises: a) an increased expression level in one, two, three, four, five, six, or more, or all of the PCS1 SEGs (SubtypeID=1) listed in Table 1; and/or b) a decreased or insignificantly changed expression level in one, two, three, four, five, six, or more, or all of the non-PCS1 SEGs (SubtypeID≠1) listed in Table 1. In some embodiments, the marker for the subtype comprises: a) an increased expression level in one, two, three, four, five, six, or more, or all of STMN1, MCM4, CCNB1, CDC6, CDKN3, EZH2, TPX2, FOXM1, KIF11, HMMR, MKI67, and KNTC1; and/or b) a decreased or insignificantly changed expression level in one, two, three, four, five, six, or more, or all of RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45. In some embodiments, the marker for the subtype comprises: a) an increased expression level in one, two, three, four, five, six, or more, or all of the PCS2 SEGs (SubtypeID=2) listed in Table 1; and/or b) a decreased or insignificantly changed expression level in one, two, three, four, five, six, or more, or all of the non-PCS2 SEGs (SubtypeID≠2) listed in Table 1. In some embodiments, the marker for the subtype comprises: a) an increased expression level in one, two, three, four, five, six, or more, or all of RAB3B, SLC4A4, ANK3, GJB1, and SLC12A2; and/or b) a decreased or insignificantly changed expression level in one, two, three, four, five, six, or more, or all of STMN1, MCM4, CCNB1, CDC6, CDKN3, EZH2, TPX2, FOXM1, KIF11, HMMR, MKI67, KNTC1, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45. In some embodiments, the marker for the subtype comprises: a) an increased expression level in one, two, three, four, five, six, or more, or all of the PCS3 SEGs (SubtypeID=3) listed in Table 1; and/or b) a decreased or insignificantly changed expression level in one, two, three, four, five, six, or more, or all of the non-PCS3 SEGs (SubtypeID≠3) listed in Table 1. In some embodiments, the marker for the subtype comprises: a) an increased expression level in one, two, three, four, five, six, or more, or all of CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45; and/or b) a decreased or insignificantly changed expression level in one, two, three, four, five, six, or more, or all of STMN1, MCM4, CCNB1, CDC6, CDKN3, EZH2, TPX2, FOXM1, KIF11, HMMR, MKI67, KNTC1, RAB3B, SLC4A4, ANK3, GJB1, and SLC12A2.

Various embodiments of the present invention provide a method for classifying a prostate cancer into a prostate cancer subtype, comprising: a) determining pathway activation gene expression signatures in a plurality of prostate cancer specimens; b) converting the pathway activation gene expression signatures into pathway activation profiles; c) grouping the pathway activation profiles into independent clusters, wherein each independent cluster corresponds to the prostate cancer subtype; and d) classifying the prostate cancer into the prostate cancer subtype if the pathway activation profile corresponding to the prostate cancer subtype is detected in the prostate cancer. In some embodiments, the pathway activation profiles are selected from PTEN, ES, AR-V, PRF, EZH2, AV, AR, SPOP, FOXA1, ERG, RAS, MES, PRC, and PN. In some embodiments, the prostate cancer subtype is PCS1, PCS2, or PCS3. In some embodiments, the PCS1 subtype comprises pathway activation profiles PTEN, ES, AR-V, PRF, EZH2, or AV, or combinations thereof; the PCS2 subtype comprises pathway activation profiles AR, SPOP, FOXA1, or ERG, or combinations thereof; and the PCS3 subtype comprises pathway activation profiles RAS, MES, PRC, or PN, or combinations thereof. In some embodiments, determining pathway activation gene expression signatures in the prostate cancer specimens comprises: a) obtaining a first prostate cancer dataset, wherein the first prostate cancer dataset comprises gene expression profiles; b) selecting a second prostate cancer dataset from the first prostate dataset, wherein the second prostate cancer dataset is numerically smaller than the first prostate cancer dataset; c) normalizing the second prostate cancer dataset; d) removing gene expression profiles for benign prostate tissues; and e) normalizing the gene expression profiles to obtain a merged dataset comprising the pathway activation gene expression signatures. In some embodiments, the gene expression profiles comprise gene expression profiles for benign prostate tissues and gene expression profiles for malignant prostate tissues. In some embodiments, the malignant prostate tissues are primary tumors, metastatic prostate cancers, or castration resistant prostate cancers, or combinations thereof. In some embodiments, normalizing the second prostate cancer dataset is performed using a quantile method. In some embodiments, normalizing the gene expression profiles is performed using median centering and quantile scaling. In some embodiments, converting the pathway activation gene expression signatures into pathway activation profiles comprises: a) calculating the difference between (i) an error-weighted mean of expression values of the genes in the pathway activation gene expression signatures and (ii) an error-weighted mean of all genes after normalization; b) calculating Z-scores for the pathway activation gene expression signatures; and c) preparing a matrix of pathway activation scores from the pathway activation gene expression signatures. In some embodiments, grouping the pathway activation profiles into independent clusters comprises, determining a number of independent clusters by applying a consensus non-negative matrix factorization clustering method.

Various embodiments of the present invention provide a method for classifying a prostate cancer in a subject, comprising: a) determining pathway activation gene expression signatures in a plurality of prostate cancer specimens; b) converting the pathway activation gene expression signatures into pathway activation profiles; c) grouping the pathway activation profiles into independent clusters, wherein each independent cluster corresponds to a prostate cancer subtype; d) obtaining a sample from the subject; e) determining a pathway activation profile in the sample; and f) classifying the prostate cancer in the subject into the prostate cancer subtype if the pathway activation profile corresponding to the prostate cancer subtype is detected in the sample. In some embodiments, the pathway activation profiles are selected from PTEN, ES, AR-V, PRF, EZH2, AV, AR, SPOP, FOXA1, ERG, RAS, MES, PRC, and PN. In some embodiments, the prostate cancer subtype is PCS1, PCS2, or PCS3. In some embodiments, the PCS1 subtype comprises pathway activation profiles PTEN, ES, AR-V, PRF, EZH2, or AV, or combinations thereof; the PCS2 subtype comprises pathway activation profiles AR, SPOP, FOXA1, or ERG, or combinations thereof; and the PCS3 subtype comprises pathway activation profiles RAS, MES, PRC, or PN, or combinations thereof. In some embodiments, the PCS1 subtype is characterized in that it has an increased probability of progressing to metastatic disease or prostate cancer specific mortality when compared to the PCS2 subtype or PCS3 subtype. In some embodiments, determining pathway activation gene expression signatures in the prostate cancer specimens comprises: a) obtaining a first prostate cancer dataset, wherein the first prostate cancer dataset comprises gene expression profiles; b) selecting a second prostate cancer dataset from the first prostate dataset, wherein the second prostate cancer dataset is numerically smaller than the first prostate cancer dataset; c) normalizing the second prostate cancer dataset; d) removing gene expression profiles for benign prostate tissues; and e) normalizing the gene expression profiles to obtain a merged dataset comprising the pathway activation gene expression signatures. In some embodiments, the gene expression profiles comprise gene expression profiles for benign prostate tissues and gene expression profiles for malignant prostate tissues. In some embodiments, the malignant prostate tissues are primary tumors, metastatic prostate cancers, or castration resistant prostate cancers, or combinations thereof. In some embodiments, normalizing the second prostate cancer dataset is performed using a quantile method. In some embodiments, normalizing the gene expression profiles is performed using median centering and quantile scaling. In some embodiments, converting the pathway activation gene expression signatures into pathway activation profiles comprises: a)

calculating the difference between (i) an error-weighted mean of expression values of the genes in the pathway activation gene expression signatures and (ii) an error-weighted mean of all genes after normalization; b) calculating Z-scores for the pathway activation gene expression signatures; and c) preparing a matrix of pathway activation scores from the pathway activation gene expression signatures. In some embodiments, grouping the pathway activation profiles into independent clusters comprises, determining a number of independent clusters by applying a consensus non-negative matrix factorization clustering method. In some embodiments, the sample is a tissue sample or blood. In some embodiments, the sample is a prostate tissue or blood circulating tumor cells. In some embodiments, the blood circulating tumor cells are classified into the PCS1 subtype. In some embodiments, the method further comprises identifying the cancer as having resistance to enzalutamide.

BRIEF DESCRIPTION OF DRAWINGS

FIG. 1A, schematic showing the process of collecting and merging prostate cancer transcriptomes. FIG. 1B, clinical composition of 2,115 prostate cancer cases. FIG. 1C, MDS of merged expression profiles after MCQ or XPN correction in the DISC cohort. Dots with different colors and/or shading represent different batches or datasets. FIG. 1D, hierarchical clustering illustrates the sample distribution of uncorrected (top), corrected by MCQ (middle), and corrected by XPN (bottom). Different colors and/or shading on "Batches" rows represent different batches or datasets from the individual studies. FIG. 1E, MDS of pathway activation profiles in the DISC cohort shows distribution of the samples from same batches. Dots with different colors and/or shading represent different batches or datasets.

FIG. 2A, consensus matrix depicts robust separation of tumors into three subtypes. FIG. 2B, changes of cophenetic coefficient and silhouette score at rank 2 to 6. FIG. 2C, pathway activation profiles of 1,321 tumors defines three prostate cancer subtypes. FIG. 2D, score plot of PCA for benign and three subtypes. FIG. 2E and FIG. 2F, the three subtypes were recognized in 10 independent cohorts. FIG. 2G and FIG. 2H, correlation of pathway activation profiles in 8 prostate cancer cell lines from the CCLE and 11 prostate cancer mouse models and probability from the pathway classifier. FIG. 2I depicts the pathway activation scores. FIG. 2J depicts the Z score of benign signature.

FIG. 3A-FIG. 3H(i)-(x) illustrate, in accordance with various embodiments of the present invention, comparison of the PCS subtypes with previously described subtypes. FIG. 3A, distribution of TCGA tumors (n=333) using the PCS subtypes compared with TCGA subtypes. FIG. 3B, relationship between PCS subtyping and TCGA subtypes. FIG. 3C, distribution of GRID tumors (n=1,626) using PCS categories compared with Tomlins subtypes. FIG. 3D, relationship between PCS subtyping and Tomlins subtypes. FIG. 3E and FIG. 3F, association of metastasis-free survival using Tomlins subtypes and using the PCS subtypes in the GRID tumors. FIG. 3G, metastasis-free survival in tumors of $GS \leq 7$ (left) and $GS \geq 8$ (right). FIG. 3H(i)-(x) depicts the correlation of the subtypes with clinical outcomes in independent cohorts.

FIG. 4A, relative gene expression (left) and pathway inclusion (right) of SEGs are displayed. FIG. 4B, cellular processes enriched by each of the three subtype enriched genes (SEGs) (P<0.05). FIG. 4C, expression of the luminal and basal markers in the three subtypes. FIG. 4D, enrichment of basal stem cell signature. FIG. 4E, correlation of pathway activities between samples from human and mouse prostate (left) and probability from the pathway classifier (right).

FIG. 5A, heatmap displays the mean expression pattern of the 37-gene panel in the three subtypes from the DISC cohort. FIG. 5B, hierarchical clustering of 77 CTCs obtained from CRPC patients by gene expression of the 37-gene panel. Bar plot in the bottom displays probability of PCS assignment from application of the classifier. FIG. 5C, schematic showing process of gene selection from 428 SEGs. FIG. 5D, graph showing comparison of mean squared errors (MSE) of 428 genes and 37 genes.

DETAILED DESCRIPTION OF THE INVENTION

Figures 1A, 1B:
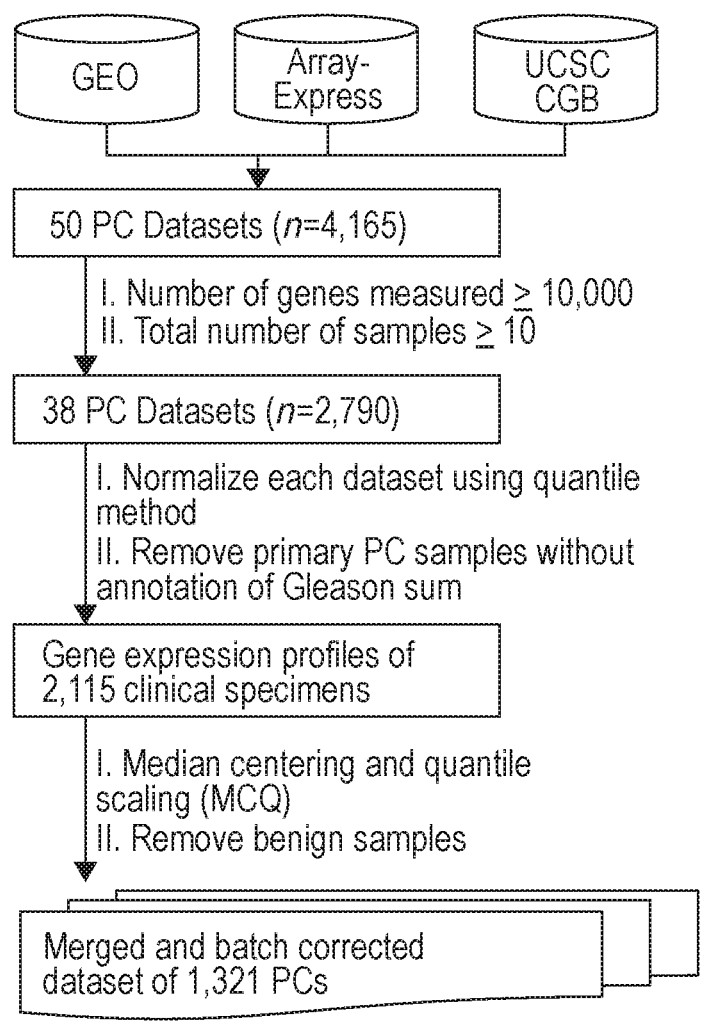
FIG. 1A-FIG. 1E illustrate, in accordance with various embodiments of the present invention, integration of prostate cancer transcriptome and quality control.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual 4th ed.*, Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of a tumor, delay or slowing of a tumor, and amelioration or palliation of symptoms associated with a tumor.

"Disorders", "diseases", "conditions" and "disease conditions," as used herein may include, but are in no way limited to any form of malignant neoplastic cell proliferative disorders or diseases. Examples of such disorders include but are not limited to cancer and tumor.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant cancers, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, via inhalation, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism, e.g., a tumor sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; tissue sample; tumor sample; and/or tumor biopsy etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In one embodiment, the subject is human.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., prostate cancer) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

As used herein, "variants" can include, but are not limited to, those that include conservative amino acid mutations, SNP variants, splicing variants, degenerate variants, and biologically active portions of a gene. A "degenerate variant" as used herein refers to a variant that has a mutated nucleotide sequence, but still encodes the same polypeptide due to the redundancy of the genetic code.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As used herein, the term "antiandrogen" (also interchangeably called as androgen signaling inhibitor or blocker) refers to any agent that inhibits the androgen signaling, including inhibition of any molecular signaling steps upstream or downstream of androgen. An antiandrogen can be a small molecule; a nucleic acid such as siRNA, shRNA, and miRNA; a nucleic acid analogue such as PNA, pc-PNA, and LNA; an aptamer; a ribozyme; a peptide; a protein; an avimer; or an antibody, or variants and fragments thereof. Antiandrogens prevent androgens from expressing their biological effects on responsive cells, tissues and organs. Antiandrogens alter the androgen pathway by inhibiting androgen receptors (ARs) or suppressing androgen production. Examples of antiandrogens include but are not limited to AR ligands such as AR antagonists and selective AR modulators (SARMs), and androgen synthesis inhibitors such as enzyme inhibitors and antigonadotropins. Examples of AR antagonists include but are not limited to flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), and cimetidine. Examples of SARMs include but are not limited to andarine and enobosarm (ostarine). Examples of enzyme inhibitors include but are not limited to 5α-reductase inhibitors (e.g., finasteride, dutasteride, alfatradiol, and saw palmetto extract), CYP17A1 (e.g., 17α-hydroxylase/17,20-lyase) inhibitors (e.g., cyproterone acetate, spironolactone, danazol, gestrinone, ketoconazole, and abiraterone acetate), 3β-Hydroxysteroid dehydrogenase inhibitors (e.g., danazol, gestrinone, and abiraterone acetate), 17β-Hydroxysteroid dehydrogenase inhibitors (e.g., danazol and simvastatin), CYP11A1 (cholesterol side-chain cleavage enzyme) inhibitors (e.g., aminoglutethimide and danazol), and HMG-CoA reductase inhibitors (e.g., statins such as atorvastatin, simvastatin). Examples of antigonadotropins include but are not limited to progestogens (e.g., progesterone, cyproterone acetate, medroxyprogesterone acetate, megestrol acetate, chlormadinone acetate, spironolactone, and drospirenone), estrogens (e.g., estradiol, ethinyl estradiol, diethylstilbestrol, and conjugated equine estrogens), GnRH analogues such as GnRH agonists (e.g., buserelin, deslorelin, gonadorelin, goserelin, histrelin, leuprorelin, nafarelin, and triptorelin) and GnRH antagonists (e.g., abarelix, cetrorelix, degarelix, and ganirelix), and anabolic steroids (e.g., nandrolone and oxandrolone).

As used herein, the term "Src signaling inhibitor" (also interchangeably called as Src signaling blocker, Src inhibitor, Src blocker, anti-Src agent, reagent, molecule, compound, or drug) refers to any agent that inhibits the Src signaling, including inhibition of any molecular signaling steps upstream or downstream of Src. A Src signaling inhibitor can be a small molecule; a nucleic acid such as siRNA, shRNA, and miRNA; a nucleic acid analogue such as PNA, pc-PNA, and LNA; an aptamer; a ribozyme; a peptide; a protein; an avimer; or an antibody, or variants and fragments thereof. Examples of Src signaling inhibitor include but are not limited to Src family tyrosine kinase inhibitor and Bcr-Abl tyrosine kinase inhibitor. Examples of Bcr-Abl tyrosine kinase inhibitor include but are not limited to imatinib, bafetinib, nilotinib, dasatinib, bosutinib, ponatinib, and 1,3,4 thiadiazole derivatives such as substance 14.

As used herein, the term "mitotic inhibitor" or "mitotic blocker" refers to any agent that inhibits mitosis or cell division, including inhibition of any molecular signaling steps involved in mitosis or cell division. A mitotic inhibitor can be a small molecule; a nucleic acid such as siRNA, shRNA, and miRNA; a nucleic acid analogue such as PNA, pc-PNA, and LNA; an aptamer; a ribozyme; a peptide; a protein; an avimer; or an antibody, or variants and fragments thereof. Mitotic inhibitors interfere with the assembly and disassembly of tubulin into microtubule polymers, which are structures that pull the cell apart when it divides. Examples of mitotic inhibitors include but are not limited to taxanes, vinca alkaloids, colchicine, podophyllotoxin, and griseofulvin. Examples of taxanes include but are not limited to paclitaxel, docetaxel, and cabazitaxel. Examples of vinca alkaloids include but are not limited to vinblastine, vincristine, vindesine, and vinorelbine.

As used herein, the terms "categorizing", "classifying", "stratifying", "subtyping", and "subgrouping" are interchangeable. As used herein, the terms "category", "class", "strata", "subtype", and "subgroup" are interchangeable. As used herein in, the terms "profile", "pattern", and "signature" are interchangeable. For example, "expression profile", "expression pattern", and "expression signature" are interchangeable, and "pathway activation profile", "pathway activation pattern", and "pathway activation signature" are interchangeable.

As used herein, the terms "computed" and "calculated" are interchangeable. As used herein, the terms "computing" and "calculating" are interchangeable.

In various embodiments of the present invention, the inventors describe an integrated approach involving an atypically large set of transcriptome data from over 4,600 clinical prostate cancer (PC) specimens via analysis based on pathway activation in order to identify clinically relevant prostate cancer subtypes. This approach has resulted in three distinct prostate cancer subtypes. The inventors validated the three subtypes and their prognostic significance using data from the independent patient series and various prostate cancer models. By further analyzing the gene expression profiles of the three subtypes, the inventors identified genes enriched in each of the three prostate cancer subtypes, which are associated with cell types of origin of the prostate cancer, and investigated potential therapeutic implications of the subtypes. Finally, the inventors present a 37 gene panel that can classify prostate cancer in patients into the subtypes for preclinical, clinical, and translational applications. The inventors present evidence that this new prostate cancer classification scheme may improve prognostic accuracy of evaluation of low grade tumors and may enable the development of subtype-specific therapies and companion diagnostics.

Classification System/Classification Method

In various embodiments, the present invention provides a method for classifying a prostate cancer into a prostate cancer subtype, comprising: a) determining pathway activation gene expression signatures in a plurality of prostate cancer specimens; b) converting the pathway activation gene expression signatures into pathway activation profiles; c) grouping the pathway activation profiles into independent clusters, wherein each independent cluster corresponds to the prostate cancer subtype; and d) classifying the prostate cancer into the prostate cancer subtype if the pathway activation profile corresponding to the prostate cancer subtype is detected in the prostate cancer. In some embodiments, determining pathway activation gene expression signatures in the prostate cancer specimens comprises, a) obtaining a first prostate cancer dataset, wherein the first prostate cancer dataset comprises gene expression profiles (for example as shown in FIG. 1A "50 PC Datasets"); b) selecting a second prostate cancer dataset from the first prostate dataset, wherein the second prostate cancer dataset is numerically smaller than the first prostate cancer dataset (for example as shown in FIG. 1A "38 PC Datasets"); c) normalizing the second prostate cancer dataset; d) removing gene expression profiles for benign prostate tissues; and e) normalizing the gene expression profiles to obtain a merged dataset comprising the pathway activation gene expression signatures. In some embodiments, the gene expression profiles comprise gene expression profiles for benign prostate tissues and gene expression profiles for malignant prostate tissues. In some embodiments, the malignant prostate tissues are primary tumors, metastatic prostate cancers, or castration resistant prostate cancers, or combinations thereof. In some embodiments, the second prostate cancer dataset is performed using a quantile method (Bolstad B M, Irizarry R A, Astrand M, Speed T P. A comparison of normalization methods for high density oligonucleotide array data based on variance and bias. Bioinformatics 2003; 19:185-93). In some embodiments, the normalizing the gene expression profiles is performed using median centering and quantile scaling (You S, Cho C S, Lee I, Hood L, Hwang D, Kim W U. A systems approach to rheumatoid arthritis. PLoS One 2012; 7:e51508). In some embodiments, converting the pathway activation gene expression signatures into pathway activation profiles comprises, a) calculating the difference between (i) an error-weighted mean of expression values of the genes in the pathway activation gene expression signatures and (ii) an error-weighted mean of all genes after normalization; b) calculating Z-scores for the pathway activation gene expression signatures; and c) preparing a matrix of pathway activation scores from the pathway activation gene expression signatures. In some embodiments, grouping the pathway activation profiles into independent clusters comprises, determining a number of independent clusters by applying a consensus non-negative matrix factorization clustering method. In some embodiments, the pathway activation profiles obtained from the classification method described herein are selected from but not limited to PTEN, ES, AR-V, PRF, EZH2, AV, AR, SPOP, FOXA1, ERG, RAS, MES, PRC, and PN. In some embodiments, the prostate cancer subtype is PCS1, PCS2, or PCS3. In some embodiments, the PCS1 subtype comprises pathway activation profiles PTEN, ES, AR-V, PRF, EZH2, or AV, or combinations thereof; the PCS2 subtype comprises pathway activation profiles AR, SPOP, FOXA1, or ERG, or combinations thereof; and the PCS3 subtype comprises pathway activation profiles RAS, MES, PRC, or PN, or combinations thereof.

In various embodiments, the present invention provides a method for classifying a prostate cancer in a subject, comprising: a) determining pathway activation gene expression signatures in a plurality of prostate cancer specimens; b) converting the pathway activation gene expression signatures into pathway activation profiles; c) grouping the pathway activation profiles into independent clusters, wherein each independent cluster corresponds to a prostate cancer subtype; d) obtaining a sample from the subject; e) determining a pathway activation profile in the sample; and f) classifying the prostate cancer in the subject into the prostate cancer subtype if the pathway activation profile corresponding to the prostate cancer subtype is detected in the sample.

In some embodiments, determining pathway activation gene expression signatures in the prostate cancer specimens comprises: a) obtaining a first prostate cancer dataset, wherein the first prostate cancer dataset comprises gene expression profiles (for example as shown in FIG. 1A "50 PC Datasets"); b) selecting a second prostate cancer dataset from the first prostate dataset, wherein the second prostate cancer dataset is numerically smaller than the first prostate cancer dataset (for example as shown in FIG. 1A "38 PC Datasets"); c) normalizing the second prostate cancer dataset; d) removing gene expression profiles for benign prostate tissues; and e) normalizing the gene expression profiles to obtain a merged dataset comprising the pathway activation gene expression signatures. In some embodiments, the gene expression profiles comprise gene expression profiles for benign prostate tissues and gene expression profiles for malignant prostate tissues. In some embodiments, the malignant prostate tissues are primary tumors, metastatic prostate cancers, or castration resistant prostate cancers, or combinations thereof. In some embodiments, normalizing the second prostate cancer dataset is performed using a quantile method (Bolstad B M, Irizarry R A, Astrand M, Speed T P. A comparison of normalization methods for high density oligonucleotide array data based on variance and bias. Bioinformatics 2003; 19:185-93). In some embodiments, normalizing the gene expression profiles is performed using median centering and quantile scaling (You S, Cho C S, Lee I, Hood L, Hwang D, Kim W U. A systems approach to rheumatoid arthritis. PLoS One 2012; 7:e51508). In some embodiments, converting the pathway activation gene expression signatures into pathway activation profiles comprises, a) calculating the difference between (i) an error-weighted mean of expression values of the genes in the pathway activation gene expression signatures and (ii) an error-weighted mean of all genes after normalization; b) calculating Z-scores for the pathway activation gene expression signatures; and c) preparing a matrix of pathway activation scores from the pathway activation gene expression signatures. In some embodiments, grouping the pathway activation profiles into independent clusters comprises, determining a number of independent clusters by applying a consensus non-negative matrix factorization clustering method. In some embodiments, the pathway activation profiles obtained from the classification method described herein are selected from but not limited to PTEN, ES, AR-V, PRF, EZH2, AV, AR, SPOP, FOXA1, ERG, RAS, MES, PRC, and PN. In some embodiments, the prostate cancer subtype is PCS1, PCS2, or PCS3. In some embodiments, the PCS1 subtype comprises pathway activation profiles PTEN, ES, AR-V, PRF, EZH2, or AV, or combinations thereof; the PCS2 subtype comprises pathway activation profiles AR, SPOP, FOXA1, or ERG, or combinations thereof; and the PCS3 subtype comprises pathway activation profiles RAS, MES, PRC, or PN, or combinations thereof. In some embodiments, the PCS1 subtype is characterized in that it has an increased probability of progressing to metastatic disease and/or prostate cancer specific mortality when compared to the PCS2 subtype or PCS3 subtype. In some embodiments, the sample is a tissue sample or blood. In some embodiments, the sample is a prostate tissue or blood circulating tumor cells. In some embodiments, the blood circulating tumor cells are classified into the PCS1 subtype. In some embodiments, the method further comprises identifying the cancer as having resistance to enzalutamide. In one embodiment, PCS1 subtype prostate cancer is resistant to enzalutamide.

In various embodiments, the present invention provides a method for classifying prostate cancer into subtypes, comprising: a) obtaining a sample from a subject; b) assaying the sample to detect changes in gene expression of one or more genes relative to reference samples or values; c) determining the presence of an expression pattern of the one or more genes associated with the subtype in the sample based on the detected changes; and d) classifying the cancer in the subject into the subtype if the expression pattern of the one or more genes associated with the subtype is detected in the sample. In some embodiments, the subtype is PCS1, PCS2, or PCS3. In some embodiments, the one or more genes comprise one, two, three, four, five, six, or more, or all of the genes listed in Table 1. In some embodiments, the one or more genes comprise one, two, three, four, five, six, or more, or all of STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45. In some embodiments, the sample is a tissue sample or blood. In some embodiments, the sample is a prostate tissue or blood circulating tumor cells. In some embodiments, the blood circulating tumor cells are classified into the PCS1 subtype. In some embodiments, the method further comprises identifying the cancer as having resistance to enzalutamide. In one embodiment, PCS1 subtype prostate cancer is resistant to enzalutamide Diagnostic and Prognostic Methods Various embodiments of the present invention provide a method for classifying a cancer into one or more subtypes in a subject having or suspected of having the cancer. The method comprises: obtaining a sample from the subject; assaying the sample to detect changes in gene expression in one or more pathways relative to reference samples or values; computing activity scores (as described herein) of the one or more pathways based on the detected changes in the gene expression; determining, in the sample, a pathway activation profile of the one or more pathways associated with the subtype of the cancer based on the computed activity scores of the one or more pathways; and classifying a cancer into the subtype in the subject if the pathway activation profile associated with the subtype is detected in the sample. In one embodiment, computing activity scores, as described herein, comprises a) calculating the difference between (i) an error-weighted mean of expression values of the genes in the pathway activation gene expression signatures and (ii) an error-weighted mean of all genes after normalization; b) calculating Z-scores for the pathway activation gene expression signatures; and c) preparing a matrix of pathway activation scores from the pathway activation gene expression signatures. In one embodiment, the change in the gene expression is an increase in the gene expression level of the one or more genes in the pathway. In another embodiment, the change in the gene expression is a decrease in the gene expression level of the one or more genes in the pathway. In one embodiment, the cancer is prostate cancer. In some embodiments, the prostate cancer subtypes are PCS1, PCS2 or PCS3 as described herein. In various embodiments, the activity scores are computed as described herein.

Various embodiments of the present invention provide a method for classifying a cancer in a subject having or suspected of having the cancer. The method comprises: obtaining a sample from the subject; assaying the sample to detect changes in gene expression of one or more genes relative to reference samples or values; determining the presence of gene expression patterns of the one or more genes associated with the subtype in the sample based on the detected changes; and classifying the cancer in the subject into the subtype if the gene expression pattern of the one or more genes associated with the subtype is detected in the sample. In one embodiment, the change in the gene expression is an increase in expression level of the gene. In another embodiment, the change in the gene expression is a decrease in gene expression level of the gene. In one embodiment, the cancer is prostate cancer. In some embodiments, the prostate cancer subtypes are PCS1, PCS2 or PCS3 as described herein.

In some embodiments, provided herein are methods for prognosing prostate cancer in a subject having or suspected of having prostate cancer. The methods comprise classifying the cancer comprising: obtaining a sample from the subject; assaying the sample to detect changes in gene expression in one or more pathways relative to reference samples or values; computing activity scores (as described herein) of the one or more pathways based on the detected changes in the gene expression; determining, in the sample, the pathway activation profile of the one or more pathways associated with the subtype of the cancer based on the computed activity scores of the one or more pathways; and classifying the cancer into the subtype in the subject if the pathway activation profile associated with the subtype is detected in the sample. In one embodiment, the subject has PCS1 prostate cancer subtype. In an embodiment, the PCS1 subtype is associated with poor prognosis. In one embodiment, the change in the gene expression is an increase in the gene expression level of the one or more genes in the pathway. In another embodiment, the change in the gene expression is a decrease in the gene expression level of the one or more genes in the pathway.

In some embodiments, provided herein are methods for prognosing prostate cancer in a subject having or suspected of having prostate cancer. The methods comprise classifying the cancer comprising: obtaining a sample from the subject; assaying the sample to detect changes in gene expression of one or more genes relative to reference samples or values; determining the presence of gene expression patterns of the one or more genes associated with the subtype in the sample based on the detected changes; and classifying the cancer in the subject into the subtype if the gene expression pattern of the one or more genes associated with the subtype is detected in the sample. In one embodiment, the subject has PCS1 prostate cancer subtype. In an embodiment, the PCS1 subtype is associated with poor prognosis. In one embodiment, the change in the gene expression is an increase in the gene expression level of the one or more genes in the pathway. In another embodiment, the change in the gene expression is a decrease in the gene expression level of the one or more genes in the pathway.

In various embodiments, the cancer is prostate cancer (PC), low grade PC, high grade PC, benign PC, aggressive PC, primary PC, secondary PC, luminal PC, basal PC, metastatic PC, castration-resistant PC (CRPC), recurrent PC, or non-recurrent PC, or a combination thereof.

In various embodiments, the subtype of prostate cancer is PCS1, PCS2, or PCS3 as described herein.

In various embodiments, the one or more pathways comprise one, two, three, four, five, six, or more, or all of the pathways listed in Table 4 (namely, AR inducible pathway, AR-Variant inducible pathway, PTEN-null inducible pathway, ERG-fusion inducible pathway, FOXA1 inducible pathway, SPOP-mutation inducible pathway, EZH2-solo inducible pathway, Polycomb repression pathway, RAS activation pathway, Stemness pathway, Aggressive Variant pathway, Pro-neural pathway, Mesenchymal pathway, and Proliferation pathway). In various embodiments, non-limiting examples of pathway activation profile for PCS1 subtype, pathway activation profile for PCS2 subtype, and pathway activation profile for PCS3 subtype, are shown in FIG. 2. In one embodiment, pathways PTEN, ES, AR-V, PRF, EZH2 and AV are activated in prostate cancer subtype PCS1. In another embodiment, pathways AR, SPOP, FOXA1 and ERG are activated in prostate cancer subtype PCS2. In a further embodiment, pathways RAS, MES, PRC and PN are activated in prostate cancer subtype PCS3. In some embodiments, the sample is a blood sample or a prostate tissue sample.

Non-limiting examples of the gene expression pattern of PCS1 subtype, gene expression pattern of PCS2 subtype, and gene expression pattern of PCS3 subtype are shown in FIG. 5 or Table 1. In some embodiments, the gene expression pattern for the PCS1 subtype comprises increased gene expression in one, two, three, four, five, six, or more, or all of the PCS1 SEGs (SubtypeID=1) listed in FIG. 5 or Table 1 and/or decreased gene expression in one, two, three, four, five, six, or more, or all of the non-PCS1 SEGs (SubtypeID≠1) listed in FIG. 5 or Table 1. In some embodiments, the gene expression pattern for PCS2 subtype comprises increased gene expression in one, two, three, four, five, six, or more, or all of the PCS2 SEGs (SubtypeID=2) listed in FIG. 5 or Table 1 and/or decreased gene expression in one, two, three, four, five, six, or more, or all of the non-PCS2 SEGs (SubtypeID≠2) listed in FIG. 5 or Table 1. In some embodiments, the gene expression pattern for PCS3 subtype comprises increased gene expression in one, two, three, four, five, six, or more, or all of the PCS3 SEGs (SubtypeID=3) listed in FIG. 5 or Table 1 and/or decreased gene expression in one, two, three, four, five, six, or more, or all of the non-PCS3 SEGs (SubtypeID≠3) listed in FIG. 5 or Table 1. In various embodiments, the one or more genes comprise one, two, three, four, five, six, or more, or all of the genes with more than 80%, 85%, 90%, 95%, or 99% consistency listed in Table 1 or FIG. 5. In various embodiments, the one or more genes comprise one, two, three, four, five, six, or more, or all of the genes with about 100% consistency listed in Table 1 or FIG. 5.

TABLE 1

Gene expression patterns in PCS1, PCS2 and PCS3 subtypes.

| | | | | Fold Change | | | |
| --- | --- | --- | --- | --- | --- | --- | --- |
| Order | EntrezID | Symbol | SubtypeID | PCS1 | PCS2 | PCS3 | Consistency |
| 1 | 699 | BUB1 | 1 | 0.732878 | −0.29233 | −0.35893 | 0.6 |
| 2 | 24137 | KIF4A | 1 | 0.796567 | −0.35685 | −0.35413 | 0.5 |
| 3 | 890 | CCNA2 | 1 | 0.704881 | −0.23407 | −0.38855 | 0.9 |
| 4 | 1062 | CENPE | 1 | 0.607498 | −0.25037 | −0.29012 | 0.7 |

TABLE 1-continued

Gene expression patterns in PCS1, PCS2 and PCS3 subtypes.

| | | | | Fold Change | | | |
|---|---|---|---|---|---|---|---|
| Order | EntrezID | Symbol | SubtypeID | PCS1 | PCS2 | PCS3 | Consistency |
| 5 | 1164 | CKS2 | 1 | 1.036744 | −0.25972 | −0.64929 | 0.9 |
| 6 | 9787 | DLGAP5 | 1 | 0.831705 | −0.3142 | −0.42348 | 0.9 |
| 7 | 11004 | KIF2C | 1 | 0.736702 | −0.37172 | −0.28916 | 0.5 |
| 8 | 701 | BUB1B | 1 | 0.742463 | −0.22647 | −0.42774 | 0.7 |
| 9 | 983 | CDK1 | 1 | 0.965364 | −0.30454 | −0.54688 | 0.7 |
| 10 | 990 | CDC6 | 1 | 0.616512 | −0.16806 | −0.37357 | 0.9 |
| 11 | 1058 | CENPA | 1 | 0.70422 | −0.33929 | −0.29117 | 0.4 |
| 12 | 9493 | KIF23 | 1 | 0.609925 | −0.32145 | −0.22679 | 0.9 |
| 13 | 891 | CCNB1 | 1 | 0.79608 | −0.15555 | −0.53894 | 0.9 |
| 14 | 991 | CDC20 | 1 | 0.918191 | −0.45797 | −0.3653 | 0.8 |
| 15 | 1063 | CENPF | 1 | 1.176024 | −0.4504 | −0.59316 | 1 |
| 16 | 3161 | HMMR | 1 | 0.916977 | −0.28956 | −0.51921 | 0.9 |
| 17 | 6241 | RRM2 | 1 | 0.96256 | −0.26336 | −0.58237 | 0.9 |
| 18 | 6790 | AURKA | 1 | 0.789153 | −0.26199 | −0.43506 | 0.6 |
| 19 | 9133 | CCNB2 | 1 | 0.868887 | −0.19926 | −0.5611 | 0.9 |
| 20 | 9232 | PTTG1 | 1 | 1.163149 | −0.54816 | −0.49218 | 0.6 |
| 21 | 9735 | KNTC1 | 1 | 0.610572 | −0.25666 | −0.28696 | 1 |
| 22 | 9928 | KIF14 | 1 | 0.580428 | −0.31983 | −0.20302 | 0.3 |
| 23 | 11130 | ZWINT | 1 | 0.903893 | −0.18787 | −0.60157 | 0.8 |
| 24 | 51203 | NUSAP1 | 1 | 1.088921 | −0.32751 | −0.63161 | 0.9 |
| 25 | 113130 | CDCA5 | 1 | 0.68834 | −0.30251 | −0.31141 | 0.4 |
| 26 | 259266 | ASPM | 1 | 0.912815 | −0.37851 | −0.4338 | 0.7 |
| 27 | 4173 | MCM4 | 1 | 0.661987 | −0.24561 | −0.34118 | 1 |
| 28 | 9768 | KIAA0101 | 1 | 1.067884 | −0.26787 | −0.66846 | 0.8 |
| 29 | 22974 | TPX2 | 1 | 1.099269 | −0.394 | −0.57929 | 0.9 |
| 30 | 29128 | UHRF1 | 1 | 0.748383 | −0.35395 | −0.31552 | 0.3 |
| 31 | 51514 | DTL | 1 | 0.687434 | −0.35548 | −0.26189 | 0.6 |
| 32 | 332 | BIRC5 | 1 | 0.926629 | −0.40355 | −0.4226 | 0.7 |
| 33 | 1894 | ECT2 | 1 | 0.65386 | 0.150249 | −0.69846 | 0.9 |
| 34 | 2171 | FABP5 | 1 | 0.590057 | −0.08456 | −0.42775 | 0.3 |
| 35 | 4001 | LMNB1 | 1 | 0.691259 | −0.25556 | −0.35711 | 0.8 |
| 36 | 7153 | TOP2A | 1 | 1.212938 | −0.33307 | −0.73275 | 0.9 |
| 37 | 7272 | TTK | 1 | 0.785224 | −0.1954 | −0.49297 | 0.9 |
| 38 | 7298 | TYMS | 1 | 0.717222 | −0.33868 | −0.30287 | 0.8 |
| 39 | 8318 | CDC45 | 1 | 0.602291 | −0.24965 | −0.28632 | 0.8 |
| 40 | 9088 | PKMYT1 | 1 | 0.607746 | −0.36834 | −0.18178 | 0.3 |
| 41 | 9833 | MELK | 1 | 1.008142 | −0.3543 | −0.53775 | 0.9 |
| 42 | 10112 | KIF20A | 1 | 0.877737 | −0.37613 | −0.40594 | 0.5 |
| 43 | 11113 | CIT | 1 | 0.58729 | −0.34989 | −0.18123 | 0.6 |
| 44 | 54845 | ESRP1 | 1 | 0.610241 | 0.232201 | −0.7365 | 0.5 |
| 45 | 55355 | HJURP | 1 | 0.656315 | −0.23448 | −0.34656 | 0.7 |
| 46 | 64151 | NCAPG | 1 | 0.872433 | −0.34576 | −0.42933 | 0.8 |
| 47 | 79019 | CENPM | 1 | 0.590031 | −0.30965 | −0.2206 | 0.4 |
| 48 | 81831 | NETO2 | 1 | 0.60986 | 0.161958 | −0.67154 | 0.7 |
| 49 | 55502 | HES6 | 1 | 0.604261 | −0.26576 | −0.27318 | 0.3 |
| 50 | 2146 | EZH2 | 1 | 1.006638 | −0.20229 | −0.67633 | 0.9 |
| 51 | 7366 | UGT2B15 | 1 | 0.609459 | −0.43442 | −0.12244 | 0.4 |
| 52 | 54443 | ANLN | 1 | 0.695782 | −0.32235 | −0.29952 | 0.8 |
| 53 | 54892 | NCAPG2 | 1 | 0.611082 | −0.11711 | −0.4158 | 0.8 |
| 54 | 56992 | KIF15 | 1 | 0.699147 | −0.31196 | −0.31197 | 0.6 |
| 55 | 83540 | NUF2 | 1 | 0.753009 | −0.31231 | −0.35779 | 0.6 |
| 56 | 213 | ALB | 1 | 0.631156 | −0.3166 | −0.24945 | 0.6 |
| 57 | 367 | AR | 1 | 0.739025 | −0.08519 | −0.55479 | 0.4 |
| 58 | 2305 | FOXM1 | 1 | 0.692848 | −0.34179 | −0.27913 | 1 |
| 59 | 3148 | HMGB2 | 1 | 0.594215 | −0.17765 | −0.34565 | 0.9 |
| 60 | 3832 | KIF11 | 1 | 0.602635 | −0.2067 | −0.32613 | 1 |
| 61 | 3925 | STMN1 | 1 | 0.755844 | −0.19839 | −0.46504 | 1 |
| 62 | 4288 | MKI67 | 1 | 0.634432 | −0.17544 | −0.38214 | 1 |
| 63 | 7083 | TK1 | 1 | 0.835438 | −0.48747 | −0.26725 | 0.7 |
| 64 | 9055 | PRC1 | 1 | 0.881146 | −0.29139 | −0.48683 | 0.9 |
| 65 | 9134 | CCNE2 | 1 | 0.600059 | −0.17521 | −0.3529 | 0.9 |
| 66 | 9156 | EXO1 | 1 | 0.604351 | −0.30764 | −0.23472 | 0.5 |
| 67 | 10024 | TROAP | 1 | 0.722668 | −0.39012 | −0.26021 | 0.5 |
| 68 | 10460 | TACC3 | 1 | 0.618949 | −0.37565 | −0.18465 | 0.8 |
| 69 | 11065 | UBE2C | 1 | 1.164182 | −0.46906 | −0.56584 | 0.8 |
| 70 | 29089 | UBE2T | 1 | 0.89392 | −0.3859 | −0.41081 | 0.8 |
| 71 | 29127 | RACGAP1 | 1 | 0.748508 | −0.24041 | −0.4201 | 0.3 |
| 72 | 55143 | CDCA8 | 1 | 0.619341 | −0.26427 | −0.28748 | 0.5 |
| 73 | 55165 | CEP55 | 1 | 0.697617 | −0.28474 | −0.3357 | 0.6 |
| 74 | 55872 | PBK | 1 | 0.895022 | −0.33544 | −0.45818 | 0.5 |
| 75 | 79682 | MLF1IP | 1 | 0.800021 | −0.16748 | −0.53133 | 0.7 |
| 76 | 374393 | FAM111B | 1 | 0.581026 | −0.18703 | −0.32571 | 0.8 |
| 77 | 3223 | HOXC6 | 1 | 0.632505 | 0.210087 | −0.73522 | 0.2 |
| 78 | 1033 | CDKN3 | 1 | 0.868086 | −0.28547 | −0.48109 | 0.9 |

TABLE 1-continued

Gene expression patterns in PCS1, PCS2 and PCS3 subtypes.

| | | | | Fold Change | | | |
|---|---|---|---|---|---|---|---|
| Order | EntrezID | Symbol | SubtypeID | PCS1 | PCS2 | PCS3 | Consistency |
| 79 | 1951 | CELSR3 | 1 | 0.659384 | −0.39411 | −0.20231 | 0.4 |
| 80 | 6472 | SHMT2 | 1 | 0.599045 | −0.03074 | −0.48497 | 0.9 |
| 81 | 6696 | SPP1 | 1 | 0.841317 | −0.36701 | −0.38312 | 0.8 |
| 82 | 8438 | RAD54L | 1 | 0.617831 | −0.32054 | −0.23441 | 0.5 |
| 83 | 10615 | SPAG5 | 1 | 0.785096 | −0.31031 | −0.38713 | 0.7 |
| 84 | 10721 | POLQ | 1 | 0.580921 | −0.2822 | −0.23806 | 0.5 |
| 85 | 29923 | HILPDA | 1 | 0.796377 | −0.30733 | −0.39953 | 0.5 |
| 86 | 51155 | HN1 | 1 | 0.63131 | −0.13259 | −0.41889 | 0.8 |
| 87 | 8611 | PPAP2A | 2 | −0.23329 | 0.729885 | −0.47171 | 0.9 |
| 88 | 10551 | AGR2 | 2 | −0.58473 | 0.974231 | −0.39544 | 0.3 |
| 89 | 4824 | NKX3-1 | 2 | −0.30631 | 0.58501 | −0.27584 | 0.8 |
| 90 | 4072 | EPCAM | 2 | 0.348825 | 0.629971 | −0.87852 | 0.9 |
| 91 | 5865 | RAB3B | 2 | −0.1764 | 0.894862 | −0.67225 | 1 |
| 92 | 6480 | ST6GAL1 | 2 | −0.55638 | 0.691335 | −0.15942 | 0.8 |
| 93 | 23671 | TMEFF2 | 2 | 0.14689 | 0.789374 | −0.85218 | 0.7 |
| 94 | 262 | AMD1 | 2 | −0.32478 | 0.656896 | −0.32617 | 1 |
| 95 | 10040 | TOM1L1 | 2 | −0.0284 | 0.610534 | −0.53744 | 0.4 |
| 96 | 384 | ARG2 | 2 | −0.44676 | 0.625144 | −0.19244 | 0.8 |
| 97 | 776 | CACNA1D | 2 | 0.128888 | 0.628 | −0.68827 | 0.9 |
| 98 | 2982 | GUCY1A3 | 2 | −0.08874 | 0.654917 | −0.52657 | 1 |
| 99 | 6675 | UAP1 | 2 | −0.00443 | 0.68233 | −0.62404 | 1 |
| 100 | 354 | KLK3 | 2 | −0.56351 | 0.737691 | −0.19597 | 0.9 |
| 101 | 2153 | F5 | 2 | 0.264994 | 0.773606 | −0.93886 | 0.3 |
| 102 | 3109 | HLA-DMB | 2 | −0.4297 | 0.833321 | −0.39861 | 0.8 |
| 103 | 3781 | KCNN2 | 2 | −0.01902 | 0.83366 | −0.75078 | 0.7 |
| 104 | 10257 | ABCC4 | 2 | −0.03837 | 0.840833 | −0.74081 | 1 |
| 105 | 27347 | STK39 | 2 | −0.13459 | 0.622779 | −0.45773 | 1 |
| 106 | 57630 | SH3RF1 | 2 | 0.046684 | 0.601567 | −0.59352 | 0.9 |
| 107 | 445347 | TARP | 2 | −0.14311 | 0.940252 | −0.74254 | 0.7 |
| 108 | 1298 | COL9A2 | 2 | −0.19489 | 0.673584 | −0.45281 | 0.3 |
| 109 | 1803 | DPP4 | 2 | −0.86264 | 0.714411 | 0.081739 | 0.8 |
| 110 | 2690 | GHR | 2 | −0.42541 | 0.656978 | −0.24002 | 0.8 |
| 111 | 4646 | MYO6 | 2 | 0.07681 | 0.904504 | −0.89807 | 0.8 |
| 112 | 81035 | COLEC12 | 2 | −0.08649 | 0.589295 | −0.46813 | 0.9 |
| 113 | 55 | ACPP | 2 | −1.23756 | 0.79755 | 0.326462 | 0.8 |
| 114 | 220 | ALDH1A3 | 2 | −0.75251 | 0.874735 | −0.16014 | 1 |
| 115 | 288 | ANK3 | 2 | −0.17705 | 0.584709 | −0.38631 | 1 |
| 116 | 1718 | DHCR24 | 2 | −0.10366 | 0.660574 | −0.519 | 1 |
| 117 | 1824 | DSC2 | 2 | −0.17065 | 0.73219 | −0.5275 | 1 |
| 118 | 2078 | ERG | 2 | −0.47748 | 1.143003 | −0.64262 | 0.8 |
| 119 | 2152 | F3 | 2 | −0.76862 | 0.700003 | 0.014445 | 0.9 |
| 120 | 2181 | ACSL3 | 2 | −0.15867 | 0.77747 | −0.57943 | 1 |
| 121 | 2331 | FMOD | 2 | −0.96767 | 0.847818 | 0.048977 | 0.7 |
| 122 | 2650 | GCNT1 | 2 | −0.09738 | 0.819383 | −0.67051 | 0.8 |
| 123 | 2705 | GJB1 | 2 | −0.16346 | 0.677957 | −0.48376 | 0.9 |
| 124 | 3249 | HPN | 2 | 0.232825 | 0.713752 | −0.85622 | 0.9 |
| 125 | 3817 | KLK2 | 2 | −0.52028 | 0.61895 | −0.12375 | 1 |
| 126 | 3936 | LCP1 | 2 | −0.57643 | 0.625152 | −0.08135 | 0.9 |
| 127 | 4070 | TACSTD2 | 2 | −0.68312 | 0.710865 | −0.06881 | 0.9 |
| 128 | 4477 | MSMB | 2 | −1.6707 | 0.865118 | 0.635396 | 0.4 |
| 129 | 4604 | MYBPC1 | 2 | −0.6832 | 0.713151 | −0.07084 | 0.7 |
| 130 | 5238 | PGM3 | 2 | −0.11715 | 0.676376 | −0.52198 | 1 |
| 131 | 5530 | PPP3CA | 2 | −0.0101 | 0.612551 | −0.55497 | 0.8 |
| 132 | 6652 | SORD | 2 | −0.41587 | 0.643562 | −0.23585 | 0.5 |
| 133 | 6695 | SPOCK1 | 2 | −0.43179 | 0.958522 | −0.51201 | 1 |
| 134 | 7113 | TMPRSS2 | 2 | −0.34717 | 0.625653 | −0.27823 | 0.9 |
| 135 | 7941 | PLA2G7 | 2 | −0.26875 | 1.197653 | −0.87174 | 0.7 |
| 136 | 8671 | SLC4A4 | 2 | −0.37296 | 0.703932 | −0.32816 | 1 |
| 137 | 9073 | CLDN8 | 2 | −0.16713 | 0.825686 | −0.61655 | 0.8 |
| 138 | 10269 | ZMPSTE24 | 2 | −0.04795 | 0.611414 | −0.5215 | 0.9 |
| 139 | 10321 | CRISP3 | 2 | −0.15696 | 1.017958 | −0.80218 | 0.6 |
| 140 | 10611 | PDLIM5 | 2 | 0.136575 | 0.591529 | −0.6613 | 1 |
| 141 | 10788 | IQGAP2 | 2 | −0.31507 | 0.907259 | −0.56485 | 1 |
| 142 | 10954 | PDIA5 | 2 | −0.08748 | 0.581675 | −0.46027 | 1 |
| 143 | 23316 | CUX2 | 2 | −0.43357 | 0.605124 | −0.18532 | 0.5 |
| 144 | 23327 | NEDD4L | 2 | −0.06212 | 0.646069 | −0.54125 | 0.9 |
| 145 | 25800 | SLC39A6 | 2 | −0.06339 | 0.629034 | −0.52448 | 0.9 |
| 146 | 51109 | RDH11 | 2 | −0.38407 | 0.588355 | −0.2123 | 0.9 |
| 147 | 51313 | FAM198B | 2 | −0.16945 | 0.591079 | −0.39869 | 0.7 |
| 148 | 51365 | PLA1A | 2 | −0.12517 | 0.825681 | −0.65249 | 0.5 |
| 149 | 57600 | FNIP2 | 2 | −0.12172 | 0.741522 | −0.57801 | 0.4 |
| 150 | 58511 | DNASE2B | 2 | −0.06995 | 0.682209 | −0.56779 | 0.7 |
| 151 | 59084 | ENPP5 | 2 | −0.27359 | 0.584764 | −0.30365 | 0.9 |
| 152 | 60481 | ELOVL5 | 2 | −0.11911 | 0.62122 | −0.46955 | 0.9 |

TABLE 1-continued

Gene expression patterns in PCS1, PCS2 and PCS3 subtypes.

| | | | | Fold Change | | | |
|---|---|---|---|---|---|---|---|
| Order | EntrezID | Symbol | SubtypeID | PCS1 | PCS2 | PCS3 | Consistency |
| 153 | 79054 | TRPM8 | 2 | −0.51799 | 0.886222 | −0.37164 | 0.9 |
| 154 | 79689 | STEAP4 | 2 | −0.2624 | 0.780323 | −0.49318 | 0.9 |
| 155 | 116285 | ACSM1 | 2 | 0.164289 | 0.722582 | −0.80563 | 0.8 |
| 156 | 130733 | TMEM178A | 2 | −0.68877 | 0.848187 | −0.19032 | 0.3 |
| 157 | 143503 | OR51E1 | 2 | −0.12499 | 0.640844 | −0.48257 | 0.7 |
| 158 | 148327 | CREB3L4 | 2 | −0.18542 | 0.620886 | −0.41244 | 0.9 |
| 159 | 151258 | SLC38A11 | 2 | −0.19184 | 0.589014 | −0.37761 | 0.3 |
| 160 | 9185 | REPS2 | 2 | −0.05421 | 0.646709 | −0.54861 | 1 |
| 161 | 2203 | FBP1 | 2 | −0.36904 | 0.713318 | −0.34016 | 0.7 |
| 162 | 7782 | SLC30A4 | 2 | −0.49281 | 0.677853 | −0.20148 | 0.8 |
| 163 | 10481 | HOXB13 | 2 | −0.03619 | 0.610781 | −0.531 | 0.8 |
| 164 | 11001 | SLC27A2 | 2 | 0.077893 | 0.581359 | −0.60166 | 0.4 |
| 165 | 57535 | KIAA1324 | 2 | −0.59729 | 0.836886 | −0.2583 | 0.8 |
| 166 | 120224 | TMEM45B | 2 | 0.173249 | 0.677234 | −0.77158 | 0.5 |
| 167 | 306 | ANXA3 | 2 | −0.91397 | 0.917548 | −0.0612 | 0.8 |
| 168 | 957 | ENTPD5 | 2 | −0.15434 | 0.696438 | −0.50857 | 0.9 |
| 169 | 2346 | FOLH1 | 2 | 0.029609 | 0.925683 | −0.87712 | 0.9 |
| 170 | 3081 | HGD | 2 | −0.56597 | 0.716772 | −0.17462 | 0.2 |
| 171 | 4744 | NEFH | 2 | −1.37688 | 0.580045 | 0.645966 | 0.3 |
| 172 | 4852 | NPY | 2 | −1.11902 | 1.599439 | −0.51294 | 0.6 |
| 173 | 5320 | PLA2G2A | 2 | −0.88085 | 0.83274 | −0.01154 | 0.7 |
| 174 | 5874 | RAB27B | 2 | −0.39877 | 0.594925 | −0.20575 | 1 |
| 175 | 6296 | ACSM3 | 2 | 0.000189 | 0.65262 | −0.60066 | 0.6 |
| 176 | 6558 | SLC12A2 | 2 | −0.41436 | 0.740473 | −0.32632 | 1 |
| 177 | 6646 | SOAT1 | 2 | −0.12756 | 0.602482 | −0.44507 | 0.9 |
| 178 | 7103 | TSPAN8 | 2 | −0.4271 | 0.629825 | −0.21359 | 0.6 |
| 179 | 9375 | TM9SF2 | 2 | −0.24777 | 0.586955 | −0.32779 | 1 |
| 180 | 9413 | FAM189A2 | 2 | −0.51959 | 0.580311 | −0.08879 | 1 |
| 181 | 10103 | TSPAN1 | 2 | −0.41665 | 0.716401 | −0.30221 | 1 |
| 182 | 11013 | TMSB15A | 2 | −0.035 | 0.850727 | −0.75279 | 0.6 |
| 183 | 23600 | AMACR | 2 | 0.188227 | 1.177096 | −1.24435 | 0.8 |
| 184 | 25874 | MPC2 | 2 | 0.11509 | 0.59419 | −0.64534 | 0.6 |
| 185 | 26503 | SLC17A5 | 2 | −0.08013 | 0.590589 | −0.47476 | 0.9 |
| 186 | 26872 | STEAP1 | 2 | 0.064834 | 0.6005 | −0.60809 | 0.6 |
| 187 | 26996 | GPR160 | 2 | 0.168502 | 0.821046 | −0.89984 | 0.6 |
| 188 | 27249 | MMADHC | 2 | −0.31034 | 0.661875 | −0.34312 | 0.8 |
| 189 | 51084 | CRYL1 | 2 | −0.31716 | 0.619291 | −0.29809 | 0.9 |
| 190 | 51170 | HSD17B11 | 2 | −0.05529 | 0.601338 | −0.50594 | 0.4 |
| 191 | 51280 | GOLM1 | 2 | −0.31212 | 0.913923 | −0.57351 | 1 |
| 192 | 51302 | CYP39A1 | 2 | −0.2926 | 0.623607 | −0.32311 | 0.7 |
| 193 | 51635 | DHRS7 | 2 | −0.37222 | 0.742384 | −0.36418 | 0.9 |
| 194 | 51809 | GALNT7 | 2 | −0.11074 | 0.779964 | −0.62279 | 0.9 |
| 195 | 54431 | DNAJC10 | 2 | −0.13587 | 0.76741 | −0.58971 | 0.9 |
| 196 | 54502 | RBM47 | 2 | −0.20937 | 0.585444 | −0.35931 | 0.9 |
| 197 | 55790 | CSGALNACT1 | 2 | −0.57552 | 0.876535 | −0.31343 | 0.9 |
| 198 | 56165 | TDRD1 | 2 | −0.40284 | 1.093566 | −0.66108 | 0.6 |
| 199 | 64094 | SMOC2 | 2 | −0.49596 | 0.621265 | −0.14672 | 0.8 |
| 200 | 80110 | ZNF614 | 2 | −0.04913 | 0.607409 | −0.5168 | 0.8 |
| 201 | 80157 | CWH43 | 2 | −0.35465 | 0.613516 | −0.26066 | 0.8 |
| 202 | 81285 | OR51E2 | 2 | −0.51407 | 1.196625 | −0.66061 | 0.9 |
| 203 | 84419 | C15orf48 | 2 | −0.4575 | 0.606869 | −0.16642 | 0.4 |
| 204 | 84899 | TMTC4 | 2 | −0.07848 | 0.659873 | −0.53993 | 0.9 |
| 205 | 90701 | SEC11C | 2 | −0.2865 | 0.74191 | −0.43719 | 0.8 |
| 206 | 92292 | GLYATL1 | 2 | −0.06208 | 0.704136 | −0.59471 | 0.8 |
| 207 | 131034 | CPNE4 | 2 | −0.29035 | 0.788477 | −0.47674 | 0.7 |
| 208 | 219595 | FOLH1B | 2 | 0.156082 | 0.635452 | −0.71843 | 0.3 |
| 209 | 284370 | ZNF615 | 2 | −0.08794 | 0.586175 | −0.46401 | 0.7 |
| 210 | 70 | ACTC1 | 3 | −1.02191 | −0.1473 | 1.011081 | 0.8 |
| 211 | 72 | ACTG2 | 3 | −1.76535 | 0.320045 | 1.218031 | 0.8 |
| 212 | 477 | ATP1A2 | 3 | −0.8676 | −0.16949 | 0.899292 | 0.9 |
| 213 | 5919 | RARRES2 | 3 | −0.66338 | −0.29374 | 0.83865 | 0.9 |
| 214 | 2919 | CXCL1 | 3 | −0.45737 | −0.23973 | 0.612444 | 0.7 |
| 215 | 5239 | PGM5 | 3 | −1.25303 | −0.00661 | 1.079647 | 0.9 |
| 216 | 6876 | TAGLN | 3 | −0.94824 | −0.04705 | 0.855727 | 0.8 |
| 217 | 7881 | KCNAB1 | 3 | −0.51165 | −0.16622 | 0.591319 | 0.8 |
| 218 | 10418 | SPON1 | 3 | −0.54973 | −0.20797 | 0.662352 | 0.9 |
| 219 | 284 | ANGPT1 | 3 | −0.69304 | −0.16956 | 0.749792 | 0.7 |
| 220 | 1674 | DES | 3 | −1.31754 | −0.07009 | 1.193337 | 1 |
| 221 | 1805 | DPT | 3 | −0.61865 | −0.27012 | 0.778597 | 0.7 |
| 222 | 2354 | FOSB | 3 | −1.03176 | 0.277239 | 0.628891 | 0.6 |
| 223 | 2568 | GABRP | 3 | −0.3939 | −0.27995 | 0.595074 | 0.8 |
| 224 | 4638 | MYLK | 3 | −1.43663 | 0.279998 | 0.97324 | 0.8 |
| 225 | 4660 | PPP1R12B | 3 | −0.75727 | 0.013151 | 0.636714 | 0.9 |
| 226 | 4681 | NBL1 | 3 | −0.57551 | −0.18859 | 0.666611 | 0.6 |

TABLE 1-continued

Gene expression patterns in PCS1, PCS2 and PCS3 subtypes.

| Order | EntrezID | Symbol | SubtypeID | Fold Change | | | Consistency |
| | | | | PCS1 | PCS2 | PCS3 | |
|---|---|---|---|---|---|---|---|
| 227 | 4921 | DDR2 | 3 | −0.61766 | −0.05683 | 0.581486 | 0.7 |
| 228 | 5918 | RARRES1 | 3 | −0.67217 | −0.1758 | 0.737655 | 0.7 |
| 229 | 5947 | RBP1 | 3 | −0.2789 | −0.37145 | 0.580736 | 0.6 |
| 230 | 7047 | TGM4 | 3 | −0.70809 | −0.12198 | 0.718912 | 0.5 |
| 231 | 7169 | TPM2 | 3 | −1.14192 | −0.14729 | 1.113893 | 0.8 |
| 232 | 9510 | ADAMTS1 | 3 | −0.57365 | −0.17346 | 0.651093 | 0.7 |
| 233 | 10563 | CXCL13 | 3 | −0.217 | −0.51526 | 0.660028 | 0.8 |
| 234 | 3371 | TNC | 3 | −0.57749 | −0.12098 | 0.606099 | 0.8 |
| 235 | 4684 | NCAM1 | 3 | −0.27293 | −0.41903 | 0.619395 | 0.9 |
| 236 | 59 | ACTA2 | 3 | −1.07121 | 0.044251 | 0.877075 | 0.8 |
| 237 | 290 | ANPEP | 3 | −0.86125 | 0.065063 | 0.67803 | 0.4 |
| 238 | 467 | ATF3 | 3 | −0.81384 | 0.106187 | 0.599576 | 0.5 |
| 239 | 1288 | COL4A6 | 3 | −0.67553 | −0.23058 | 0.790939 | 0.8 |
| 240 | 1410 | CRYAB | 3 | −0.72445 | −0.39396 | 0.983195 | 0.5 |
| 241 | 2294 | FOXF1 | 3 | −0.64025 | −0.18804 | 0.721573 | 0.9 |
| 242 | 2316 | FLNA | 3 | −0.80011 | −0.05759 | 0.73851 | 0.8 |
| 243 | 2920 | CXCL2 | 3 | −0.45536 | −0.23965 | 0.610645 | 0.6 |
| 244 | 3678 | ITGA5 | 3 | −0.50666 | −0.28354 | 0.694985 | 0.8 |
| 245 | 3679 | ITGA7 | 3 | −0.57694 | −0.17511 | 0.655426 | 1 |
| 246 | 3872 | KRT17 | 3 | −0.59298 | −0.21969 | 0.710193 | 0.8 |
| 247 | 4118 | MAL | 3 | −0.30253 | −0.40273 | 0.629763 | 0.8 |
| 248 | 4629 | MYH11 | 3 | −1.54975 | 0.135351 | 1.203251 | 0.8 |
| 249 | 5179 | PENK | 3 | −0.41603 | −0.40585 | 0.729874 | 0.8 |
| 250 | 5268 | SERPINB5 | 3 | −0.49718 | −0.18633 | 0.597424 | 0.8 |
| 251 | 5376 | PMP22 | 3 | −0.58417 | −0.22982 | 0.711969 | 0.7 |
| 252 | 5730 | PTGDS | 3 | −1.00841 | −0.02793 | 0.889679 | 1 |
| 253 | 6277 | S100A6 | 3 | −0.63266 | −0.22145 | 0.745817 | 0.7 |
| 254 | 6387 | CXCL12 | 3 | −0.45774 | −0.21218 | 0.587415 | 0.9 |
| 255 | 6525 | SMTN | 3 | −0.73332 | −0.20648 | 0.818281 | 0.9 |
| 256 | 6716 | SRD5A2 | 3 | −1.01803 | 0.009175 | 0.863785 | 0.9 |
| 257 | 7168 | TPM1 | 3 | −0.88168 | 0.135165 | 0.631035 | 0.8 |
| 258 | 7538 | ZFP36 | 3 | −1.11312 | 0.392642 | 0.592412 | 0.6 |
| 259 | 8013 | NR4A3 | 3 | −0.64995 | −0.03142 | 0.585773 | 0.7 |
| 260 | 8406 | SRPX | 3 | −0.57258 | −0.14163 | 0.620886 | 0.8 |
| 261 | 8854 | ALDH1A2 | 3 | −0.78346 | −0.02715 | 0.696231 | 0.9 |
| 262 | 8870 | IER3 | 3 | −0.52628 | −0.236 | 0.668058 | 0.9 |
| 263 | 9021 | SOCS3 | 3 | −0.76567 | −0.01766 | 0.672261 | 1 |
| 264 | 9260 | PDLIM7 | 3 | −0.48836 | −0.24626 | 0.64501 | 0.5 |
| 265 | 9506 | PAGE4 | 3 | −1.38822 | 0.087132 | 1.109223 | 0.8 |
| 266 | 10398 | MYL9 | 3 | −1.13266 | −0.159 | 1.116742 | 0.8 |
| 267 | 10580 | SORBS1 | 3 | −0.98189 | 0.011495 | 0.830685 | 0.8 |
| 268 | 22943 | DKK1 | 3 | −0.37356 | −0.29576 | 0.592195 | 0.7 |
| 269 | 25802 | LMOD1 | 3 | −1.03924 | −0.13072 | 1.010668 | 0.8 |
| 270 | 30008 | EFEMP2 | 3 | −0.36478 | −0.32231 | 0.609104 | 0.8 |
| 271 | 50859 | SPOCK3 | 3 | −0.85638 | −0.06028 | 0.789192 | 0.6 |
| 272 | 53826 | FXYD6 | 3 | −0.54854 | −0.3193 | 0.763775 | 0.6 |
| 273 | 64093 | SMOC1 | 3 | −0.4463 | −0.22438 | 0.588838 | 0.8 |
| 274 | 284119 | PTRF | 3 | −0.79821 | −0.07594 | 0.753768 | 1 |
| 275 | 316 | AOX1 | 3 | −0.74241 | −0.12039 | 0.746853 | 0.9 |
| 276 | 390 | RND3 | 3 | −0.80498 | −0.04926 | 0.735008 | 0.8 |
| 277 | 443 | ASPA | 3 | −0.44733 | −0.25541 | 0.618271 | 0.8 |
| 278 | 493 | ATP2B4 | 3 | −0.55513 | −0.14277 | 0.606989 | 0.8 |
| 279 | 629 | CFB | 3 | −0.63793 | −0.05022 | 0.592778 | 0.5 |
| 280 | 653 | BMP5 | 3 | −0.28977 | −0.36387 | 0.583081 | 0.8 |
| 281 | 710 | SERPING1 | 3 | −0.68451 | −0.17802 | 0.750279 | 0.7 |
| 282 | 716 | C1S | 3 | −0.81499 | −0.02649 | 0.722641 | 0.8 |
| 283 | 857 | CAV1 | 3 | −0.93403 | −0.07806 | 0.872083 | 0.7 |
| 284 | 858 | CAV2 | 3 | −0.52407 | −0.15917 | 0.595466 | 0.8 |
| 285 | 894 | CCND2 | 3 | −0.51119 | −0.15782 | 0.583186 | 0.8 |
| 286 | 1066 | CES1 | 3 | −0.71488 | −0.1904 | 0.787679 | 0.3 |
| 287 | 1191 | CLU | 3 | −0.70499 | −0.31222 | 0.891302 | 0.7 |
| 288 | 1264 | CNN1 | 3 | −1.5399 | 0.018621 | 1.302214 | 0.8 |
| 289 | 1291 | COL6A1 | 3 | −0.40342 | −0.40542 | 0.718682 | 1 |
| 290 | 1292 | COL6A2 | 3 | −0.532 | −0.23995 | 0.676587 | 1 |
| 291 | 1307 | COL16A1 | 3 | −0.50929 | −0.29474 | 0.707551 | 1 |
| 292 | 1346 | COX7A1 | 3 | −0.80342 | −0.23464 | 0.904251 | 0.9 |
| 293 | 1465 | CSRP1 | 3 | −1.10308 | 0.122379 | 0.832492 | 0.8 |
| 294 | 1577 | CYP3A5 | 3 | −0.58063 | −0.23187 | 0.710821 | 0.9 |
| 295 | 1580 | CYP4B1 | 3 | −0.40098 | −0.2692 | 0.591252 | 0.8 |
| 296 | 1593 | CYP27A1 | 3 | −0.56913 | −0.21108 | 0.681836 | 0.9 |
| 297 | 1672 | DEFB1 | 3 | −0.40478 | −0.28843 | 0.6122 | 0.7 |
| 298 | 1675 | CFD | 3 | −0.57905 | −0.30524 | 0.776983 | 1 |
| 299 | 1809 | DPYSL3 | 3 | −0.69632 | −0.07423 | 0.664887 | 0.8 |
| 300 | 2192 | FBLN1 | 3 | −1.12524 | 0.032894 | 0.933816 | 0.8 |

TABLE 1-continued

Gene expression patterns in PCS1, PCS2 and PCS3 subtypes.

| | | | | Fold Change | | | |
|---|---|---|---|---|---|---|---|
| Order | EntrezID | Symbol | SubtypeID | PCS1 | PCS2 | PCS3 | Consistency |
| 301 | 2202 | EFEMP1 | 3 | −0.54151 | −0.19884 | 0.646914 | 0.7 |
| 302 | 2263 | FGFR2 | 3 | −0.66919 | −0.08906 | 0.655293 | 0.9 |
| 303 | 2273 | FHL1 | 3 | −1.11106 | −0.01079 | 0.961858 | 0.9 |
| 304 | 2274 | FHL2 | 3 | −0.83923 | −0.02819 | 0.744972 | 0.8 |
| 305 | 2318 | FLNC | 3 | −0.74745 | −0.29375 | 0.910692 | 0.9 |
| 306 | 2564 | GABRE | 3 | −0.71531 | −0.17765 | 0.776322 | 0.8 |
| 307 | 2619 | GAS1 | 3 | −0.7175 | −0.11019 | 0.716131 | 0.9 |
| 308 | 2934 | GSN | 3 | −0.82124 | −0.02295 | 0.724736 | 0.9 |
| 309 | 2944 | GSTM1 | 3 | −0.56563 | −0.22943 | 0.69573 | 0.6 |
| 310 | 2946 | GSTM2 | 3 | −0.7024 | −0.24541 | 0.827603 | 0.7 |
| 311 | 2949 | GSTM5 | 3 | −0.6071 | −0.20369 | 0.707568 | 0.8 |
| 312 | 2950 | GSTP1 | 3 | −0.81277 | −0.30717 | 0.978992 | 0.9 |
| 313 | 3397 | ID1 | 3 | −0.75067 | −0.14742 | 0.778799 | 0.9 |
| 314 | 3399 | ID3 | 3 | −0.55305 | −0.16072 | 0.621727 | 0.9 |
| 315 | 3489 | IGFBP6 | 3 | −0.75459 | −0.26573 | 0.891019 | 0.9 |
| 316 | 3491 | CYR61 | 3 | −1.00564 | 0.246674 | 0.634637 | 0.8 |
| 317 | 3569 | IL6 | 3 | −0.39204 | −0.33016 | 0.639681 | 0.8 |
| 318 | 3764 | KCNJ8 | 3 | −0.36509 | −0.29554 | 0.584741 | 0.8 |
| 319 | 3779 | KCNMB1 | 3 | −0.94501 | −0.25442 | 1.043763 | 0.8 |
| 320 | 3852 | KRT5 | 3 | −0.9539 | −0.1843 | 0.986855 | 0.6 |
| 321 | 3860 | KRT13 | 3 | −0.61386 | −0.18989 | 0.700659 | 0.8 |
| 322 | 3866 | KRT15 | 3 | −1.10462 | −0.08224 | 1.022088 | 0.8 |
| 323 | 3910 | LAMA4 | 3 | −0.37227 | −0.33086 | 0.623392 | 0.8 |
| 324 | 3914 | LAMB3 | 3 | −0.59153 | −0.23076 | 0.719138 | 0.8 |
| 325 | 3934 | LCN2 | 3 | −0.70583 | −0.19126 | 0.780723 | 0.7 |
| 326 | 3956 | LGALS1 | 3 | −0.6414 | −0.2305 | 0.761625 | 0.6 |
| 327 | 4057 | LTF | 3 | −1.09944 | 0.124029 | 0.82785 | 0.8 |
| 328 | 4129 | MAOB | 3 | −0.94227 | 0.026149 | 0.783253 | 0.9 |
| 329 | 4147 | MATN2 | 3 | −0.73575 | 0.051341 | 0.583135 | 0.7 |
| 330 | 4211 | MEIS1 | 3 | −0.70561 | −0.05064 | 0.651146 | 0.7 |
| 331 | 4212 | MEIS2 | 3 | −0.8253 | −0.02687 | 0.731824 | 0.7 |
| 332 | 4239 | MFAP4 | 3 | −0.70001 | −0.19007 | 0.774641 | 0.8 |
| 333 | 4920 | ROR2 | 3 | −0.49307 | −0.18093 | 0.588929 | 0.8 |
| 334 | 4969 | OGN | 3 | −0.85745 | 0.073606 | 0.666914 | 0.5 |
| 335 | 5099 | PCDH7 | 3 | −0.51994 | −0.16927 | 0.601226 | 0.8 |
| 336 | 5121 | PCP4 | 3 | −1.57069 | 0.231246 | 1.132954 | 0.6 |
| 337 | 5176 | SERPINF1 | 3 | −0.64073 | −0.25706 | 0.785494 | 0.8 |
| 338 | 5348 | FXYD1 | 3 | −0.52854 | −0.32276 | 0.749826 | 0.9 |
| 339 | 5350 | PLN | 3 | −0.85008 | 0.008146 | 0.720831 | 0.6 |
| 340 | 5579 | PRKCB | 3 | −0.39028 | −0.29512 | 0.605936 | 0.9 |
| 341 | 5648 | MASP1 | 3 | −0.44301 | −0.22395 | 0.585617 | 0.8 |
| 342 | 5764 | PTN | 3 | −0.97907 | 0.065302 | 0.778758 | 0.7 |
| 343 | 5837 | PYGM | 3 | −0.52059 | −0.15809 | 0.591494 | 0.7 |
| 344 | 6273 | S100A2 | 3 | −0.54321 | −0.1449 | 0.598741 | 0.3 |
| 345 | 6275 | S100A4 | 3 | −0.42302 | −0.39463 | 0.725548 | 0.4 |
| 346 | 6347 | CCL2 | 3 | −0.78072 | 0.006393 | 0.663023 | 0.6 |
| 347 | 6376 | CX3CL1 | 3 | −0.68342 | −0.21166 | 0.780294 | 1 |
| 348 | 6401 | SELE | 3 | −0.80088 | 0.055729 | 0.634898 | 0.8 |
| 349 | 6442 | SGCA | 3 | −0.40577 | −0.26301 | 0.589654 | 0.8 |
| 350 | 6518 | SLC2A5 | 3 | −0.51265 | −0.21572 | 0.637716 | 0.8 |
| 351 | 6563 | SLC14A1 | 3 | −0.79401 | −0.06416 | 0.739323 | 0.7 |
| 352 | 6604 | SMARCD3 | 3 | −0.35997 | −0.32498 | 0.607441 | 1 |
| 353 | 6769 | STAC | 3 | −0.47465 | −0.20587 | 0.596098 | 0.8 |
| 354 | 6840 | SVIL | 3 | −0.66534 | −0.02733 | 0.595197 | 0.8 |
| 355 | 7041 | TGFB1I1 | 3 | −0.51524 | −0.24502 | 0.666896 | 1 |
| 356 | 7043 | TGFB3 | 3 | −0.56912 | −0.2945 | 0.758593 | 0.8 |
| 357 | 7077 | TIMP2 | 3 | −0.43641 | −0.26146 | 0.614477 | 0.8 |
| 358 | 7123 | CLEC3B | 3 | −0.33826 | −0.3571 | 0.618388 | 0.8 |
| 359 | 7145 | TNS1 | 3 | −0.84771 | −0.08975 | 0.808877 | 0.7 |
| 360 | 7205 | TRIP6 | 3 | −0.46717 | −0.23923 | 0.620383 | 0.9 |
| 361 | 7356 | SCGB1A1 | 3 | −0.45669 | −0.32748 | 0.692607 | 0.8 |
| 362 | 7414 | VCL | 3 | −0.60084 | −0.11342 | 0.619151 | 0.8 |
| 363 | 7732 | RNF112 | 3 | −0.37306 | −0.28463 | 0.581531 | 0.7 |
| 364 | 8309 | ACOX2 | 3 | −0.51335 | −0.20797 | 0.631185 | 0.9 |
| 365 | 8404 | SPARCL1 | 3 | −1.20127 | 0.168951 | 0.87376 | 0.8 |
| 366 | 8425 | LTBP4 | 3 | −0.53436 | −0.15048 | 0.596288 | 1 |
| 367 | 8613 | PPAP2B | 3 | −0.67164 | −0.03941 | 0.611715 | 0.7 |
| 368 | 8626 | TP63 | 3 | −1.07269 | 0.025122 | 0.895937 | 0.8 |
| 369 | 8639 | AOC3 | 3 | −0.71857 | −0.13566 | 0.740477 | 0.7 |
| 370 | 8654 | PDE5A | 3 | −0.87976 | 0.091556 | 0.669517 | 0.6 |
| 371 | 9843 | HEPH | 3 | −0.45318 | −0.27184 | 0.638407 | 1 |
| 372 | 10231 | RCAN2 | 3 | −0.6427 | −0.21565 | 0.74908 | 0.8 |
| 373 | 10278 | EFS | 3 | −0.50046 | −0.22534 | 0.636124 | 0.9 |
| 374 | 10290 | SPEG | 3 | −0.54476 | −0.23684 | 0.684658 | 1 |

TABLE 1-continued

Gene expression patterns in PCS1, PCS2 and PCS3 subtypes.

| | | | | Fold Change | | | |
|---|---|---|---|---|---|---|---|
| Order | EntrezID | Symbol | SubtypeID | PCS1 | PCS2 | PCS3 | Consistency |
| 375 | 10335 | MRVI1 | 3 | −0.6604 | −0.15611 | 0.709458 | 0.8 |
| 376 | 10406 | WFDC2 | 3 | −0.63964 | −0.23007 | 0.759716 | 0.7 |
| 377 | 10562 | OLFM4 | 3 | −1.10279 | 0.132391 | 0.823025 | 0.8 |
| 378 | 10826 | FAXDC2 | 3 | −0.48038 | −0.22945 | 0.622698 | 0.7 |
| 379 | 10974 | ADIRF | 3 | −1.00822 | 0.114667 | 0.758309 | 0.5 |
| 380 | 11030 | RBPMS | 3 | −0.63321 | −0.17213 | 0.700907 | 0.8 |
| 381 | 11117 | EMILIN1 | 3 | −0.41065 | −0.27028 | 0.600521 | 1 |
| 382 | 11155 | LDB3 | 3 | −0.52936 | −0.21976 | 0.655745 | 0.8 |
| 383 | 11170 | FAM107A | 3 | −0.86714 | −0.13489 | 0.867058 | 0.9 |
| 384 | 11259 | FILIP1L | 3 | −0.60332 | −0.18253 | 0.684863 | 0.8 |
| 385 | 11341 | SCRG1 | 3 | −0.48197 | −0.3457 | 0.731025 | 0.8 |
| 386 | 23022 | PALLD | 3 | −0.75108 | −0.03353 | 0.674363 | 0.8 |
| 387 | 23336 | SYNM | 3 | −1.44993 | 0.190874 | 1.066641 | 0.8 |
| 388 | 23584 | VSIG2 | 3 | −0.60002 | −0.13924 | 0.642202 | 0.8 |
| 389 | 23650 | TRIM29 | 3 | −0.8207 | −0.18226 | 0.870858 | 0.8 |
| 390 | 25959 | KANK2 | 3 | −0.55779 | −0.14349 | 0.609928 | 0.7 |
| 391 | 25984 | KRT23 | 3 | −0.75711 | −0.14065 | 0.778091 | 0.7 |
| 392 | 25999 | CLIP3 | 3 | −0.38782 | −0.41018 | 0.709695 | 1 |
| 393 | 26353 | HSPB8 | 3 | −0.91053 | −0.16569 | 0.932582 | 0.9 |
| 394 | 26577 | PCOLCE2 | 3 | −0.73061 | −0.11131 | 0.728395 | 0.8 |
| 395 | 27122 | DKK3 | 3 | −0.70441 | −0.0871 | 0.683669 | 0.7 |
| 396 | 27129 | HSPB7 | 3 | −0.35844 | −0.31661 | 0.598427 | 0.6 |
| 397 | 29951 | PDZRN4 | 3 | −0.8258 | −0.00679 | 0.713775 | 0.8 |
| 398 | 51285 | RASL12 | 3 | −0.56946 | −0.30566 | 0.769151 | 0.9 |
| 399 | 51676 | ASB2 | 3 | −0.56374 | −0.16152 | 0.631615 | 0.7 |
| 400 | 55679 | LIMS2 | 3 | −0.54444 | −0.25681 | 0.702765 | 0.9 |
| 401 | 58189 | WFDC1 | 3 | −0.8631 | −0.27908 | 0.996276 | 0.9 |
| 402 | 59353 | TMEM35 | 3 | −0.73144 | −0.05343 | 0.675843 | 0.5 |
| 403 | 64091 | POPDC2 | 3 | −0.59382 | −0.12841 | 0.626922 | 0.5 |
| 404 | 79625 | NDNF | 3 | −0.48848 | −0.23457 | 0.634352 | 0.4 |
| 405 | 79630 | C1orf54 | 3 | −0.41683 | −0.26077 | 0.59708 | 0.5 |
| 406 | 80206 | FHOD3 | 3 | −0.50454 | −0.22075 | 0.635398 | 0.3 |
| 407 | 83643 | CCDC3 | 3 | −0.344 | −0.31356 | 0.583248 | 0.7 |
| 408 | 83716 | CRISPLD2 | 3 | −0.70159 | −0.02191 | 0.621259 | 0.7 |
| 409 | 84417 | C2orf40 | 3 | −0.69548 | −0.24663 | 0.822807 | 0.5 |
| 410 | 84617 | TUBB6 | 3 | −0.57282 | −0.19141 | 0.666906 | 0.9 |
| 411 | 89927 | C16orf45 | 3 | −0.4606 | −0.22711 | 0.603603 | 0.9 |
| 412 | 91624 | NEXN | 3 | −0.889 | −0.05783 | 0.814888 | 0.7 |
| 413 | 91851 | CHRDL1 | 3 | −0.98756 | −0.05396 | 0.895768 | 0.6 |
| 414 | 93649 | MYOCD | 3 | −0.60736 | −0.13002 | 0.640005 | 0.8 |
| 415 | 94274 | PPP1R14A | 3 | −0.46415 | −0.31571 | 0.68817 | 0.8 |
| 416 | 112464 | PRKCDBP | 3 | −0.4874 | −0.25772 | 0.654727 | 0.3 |
| 417 | 113146 | AHNAK2 | 3 | −0.49377 | −0.31079 | 0.709021 | 0.6 |
| 418 | 116535 | MRGPRF | 3 | −0.63991 | −0.13197 | 0.669687 | 0.3 |
| 419 | 118425 | PCAT4 | 3 | −0.84039 | 0.125967 | 0.604121 | 0.1 |
| 420 | 126393 | HSPB6 | 3 | −0.50742 | −0.29286 | 0.704212 | 0.9 |
| 421 | 140597 | TCEAL2 | 3 | −0.82459 | −0.13391 | 0.829704 | 0.6 |
| 422 | 146713 | RBFOX3 | 3 | −0.60162 | −0.10432 | 0.611441 | 0.2 |
| 423 | 147906 | DACT3 | 3 | −0.51691 | −0.16054 | 0.590597 | 0.8 |
| 424 | 148741 | ANKRD35 | 3 | −0.56905 | −0.2048 | 0.675992 | 0.7 |
| 425 | 171024 | SYNPO2 | 3 | −1.26852 | 0.265743 | 0.84232 | 0.4 |
| 426 | 253827 | MSRB3 | 3 | −0.63971 | −0.0841 | 0.625468 | 0.9 |
| 427 | 387763 | C11orf96 | 3 | −0.47854 | −0.27227 | 0.660526 | 0.4 |
| 428 | 728264 | MIR143HG | 3 | −0.67359 | −0.1042 | 0.672989 | 0.2 |

In various embodiments, the prostate cancer in the subject may be classified into one of PCS1, PCS2 and PCS3 subtypes based on the changes in expression of one or more genes wherein the one or more genes comprise one, two, three, four, five, six, or more, or all of STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45. In various embodiments, the one or more genes comprise STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and/or C16orf45, or a combination thereof.

Non-limiting examples of the gene expression pattern for the PCS1 subtype, the gene expression pattern for the PCS2 subtype, and the gene expression pattern for the PCS3 subtype are shown in FIG. 5 and Table 1. In some embodiments, the gene expression pattern for the PCS1 subtype comprises increased expression levels in one, two, three, four, five, six, or more, or all of STMN1, MCM4, CCNB1, CDC6, CDKN3, EZH2, TPX2, FOXM1, KIF11, HMMR, MKI67, and KNTC1 and/or decreased expression levels in one, two, three, four, five, six, or more, or all of RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45.

In some embodiments, the gene expression pattern for the PCS2 subtype comprises increased expression levels in one, two, three, four, five, six, or more, or all of RAB3B, SLC4A4, ANK3, GJB1, and SLC12A2 and/or decreased expression levels in one, two, three, four, five, six, or more, or all of STMN1, MCM4, CCNB1, CDC6, CDKN3, EZH2, TPX2, FOXM1, KIF11, HMMR, MKI67, KNTC1, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45.

In some embodiments, the gene expression pattern for the PCS3 subtype comprises increased expression levels in one, two, three, four, five, six, or more, or all of CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45; and/or decreased expression levels in one, two, three, four, five, six, or more, or all of STMN1, MCM4, CCNB1, CDC6, CDKN3, EZH2, TPX2, FOXM1, KIF11, HMMR, MKI67, KNTC1, RAB3B, SLC4A4, ANK3, GJB1, and SLC12A2.

In one embodiments, the sample is a blood sample and the cancer (for example, prostate cancer) is classified using the methods described herein based on the gene expression and/or pathway activation profiles in the circulating tumor cells (CTCs). In another embodiment, the sample is a tumor tissue sample, for example, prostate tumor sample.

In various embodiments, the subtype is PCS1, and the subject is prognosed with a poor clinical outcome. In various embodiments, the poor clinical outcome comprises lower metastasis-free survival, higher risk of metastatic progression, higher rate of cancer specific mortality, lower overall survival, or more aggressive form of cancer, or a combination thereof.

In various embodiments, the subtype is PCS1, and the subject is prognosed with resistance to an antiandrogen, an androgen receptor (AR) antagonist, a selective AR modulator, or an androgen synthesis inhibitor. In various embodiments, the antiandrogen is flutamide, nilutamide, bicalutamide, enzalutamide, or apalutamide. In some embodiments, the subtype is PCS1, and the subject is prognosed with resistance to enzalutamide.

In various embodiments, the subtype is PCS1, and the subject is prognosed with resistance to a Src signaling inhibitor, a Src family tyrosine kinase inhibitor, or a Bcr-Abl tyrosine kinase inhibitor. In various embodiments, the Src signaling inhibitor is imatinib, bafetinib, nilotinib, dasatinib, bosutinib, or ponatinib. In some embodiments, the subtype is PCS1, and the subject is prognosed with resistance to dasatinib.

In various embodiments, the subtype is PCS1, and the subject is prognosed with resistance to a mitotic inhibitor. In various embodiments, the mitotic inhibitor is taxane, paclitaxel, docetaxel, or cabazitaxel. In some embodiments, the subtype is PCS1, and the subject is prognosed with resistance to docetaxel or taxane.

Various embodiments of the invention provide methods for personalizing therapies in a subject having or suspected of having prostate cancer, comprising: classifying the cancer by the methods described herein and administering therapies based on the cancer subtypes. In one embodiment, the subtype is PCS1 and the subject is not administered antiandrogen agents. In one embodiment, the subtype is PCS1 and the subject is not administered enzalutamide.

Treatment Methods

Various embodiments of the present invention provide a method for treating, inhibiting, preventing metastases of, reducing the severity of and/or slowing the progression of a cancer in a subject. In one embodiment, the cancer is prostate cancer. The methods include classifying the cancer by the methods described herein and administering an effective amount of a therapeutic agent so as to treat, inhibit, prevent metastases of and/or slow progression of the cancer in the subject.

In one embodiment, the methods for treating, inhibiting, preventing metastases of, reducing the severity of and/or slowing the progression of a cancer in a subject comprise: obtaining a sample from the subject; assaying the sample to detect changes in gene expression in one or more pathways relative to reference samples or values; computing activity scores (as described herein) of the one or more pathways based on the detected changes in the gene expression; determining, in the sample, the pathway activation profile of the one or more pathways associated with the subtype of the cancer based on the computed activity scores of the one or more pathways; classifying the cancer into the subtype in the subject if the pathway activation profile associated with the subtype is detected in the sample; and administering a therapeutically effective amount of a therapeutic agent to the subject, thereby treating, reducing the likelihood of having, reducing the severity of and/or slowing the progression of the cancer.

In various embodiments, the one or more pathways comprise one, two, three, four, five, six, or more, or all of the pathways listed in Table 4 (namely, AR inducible pathway, AR-Variant inducible pathway, PTEN-null inducible pathway, ERG-fusion inducible pathway, FOXA1 inducible pathway, SPOP-mutation inducible pathway, EZH2-solo inducible pathway, Polycomb repression pathway, RAS activation pathway, Stemness pathway, Aggressive Variant pathway, Pro-neural pathway, Mesenchymal pathway, and Proliferation pathway). In various embodiments, non-limiting examples of PCS1's pathway activation profile, PCS2's pathway activation profile, and PCS3's pathway activation profile are shown in FIG. 2.

In another embodiment, the methods for treating, inhibiting, preventing metastases of, reducing the severity of and/or slowing the progression of a cancer in a subject comprise obtaining a sample from the subject; assaying the sample to detect changes in gene expression of one or more genes relative to reference samples or values; determining the presence of gene expression pattern of the one or more genes associated with the subtype in the sample based on the detected changes; classifying the cancer in the subject into the subtype if the gene expression pattern of the one or more genes associated with the subtype is detected in the sample; and administering a therapeutically effective amount of a therapeutic agent to the subject, thereby treating, reducing the likelihood of having, reducing the severity of and/or slowing the progression of the cancer.

In various embodiments, the one or more genes comprise one or more subtype enriched genes (SEGs), for examples, those genes listed in Table 1 or FIG. 5. In various embodiments, the one or more genes comprise one, two, three, four, five, six, or more, or all of the genes listed in Table 1 or FIG. 5. In various embodiments, the one or more genes comprise one, two, three, four, five, six, or more, or all of the genes with more than 80%, 85%, 90%, 95%, or 99% consistency listed in Table 1 or FIG. 5. In various embodiments, the one or more genes comprise one, two, three, four, five, six, or more, or all of the genes with about 100% consistency listed in Table 1 or FIG. 5. In various embodiments, the one or more genes comprise one, two, three, four, five, six, or more, or all of the PCS1 SEGs (SubtypeID=1) listed in Table 1 or FIG. 5. In various embodiments, the one or more genes comprise one, two, three, four, five, six, or more, or all of the PCS2 SEGs (SubtypeID=2) listed in Table 1 or FIG. 5. In various embodiments, the one or more genes comprise one, two, three, four, five, six, or more, or all of the PCS3 SEGs (SubtypeID=3) listed in Table 1 or FIG. 5. In various embodiments, non-limiting examples of PCS1's expression pattern, PCS2's expression pattern, and PCS3's expression pattern are shown in Table 1 or FIG. 5.

In various embodiments, the one or more genes comprise one, two, three, four, five, six, or more, or all of STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45. In various embodiments, the one or more genes comprise STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and/or C16orf45, or a combination thereof. In various embodiments, non-limiting examples of PCS1's expression pattern, PCS2's expression pattern, and PCS3's expression pattern are shown in FIG. 5 or Table 1.

Various embodiments of the present invention provide a method for treating, preventing, reducing the likelihood of having, reducing the severity of and/or slowing the progression of a cancer in a subject. The method comprises: obtaining a sample from the subject; assaying the sample to detect a marker for a subtype of the cancer; detecting the marker for the subtype in the sample; and administering a therapeutically effective amount of a therapeutic agent to the subject, thereby treating, preventing, reducing the likelihood of having, reducing the severity of and/or slowing the progression of the cancer.

In various embodiments, the marker comprises one or more subtype enriched genes (SEGs), for examples, those genes listed in Table 1 or FIG. 5. In various embodiments, the marker comprises one, two, three, four, five, six, or more, or all of the genes listed in Table 1 or FIG. 5. In various embodiments, the marker comprises one, two, three, four, five, six, or more, or all of the genes with more than 80%, 85%, 90%, 95%, or 99% consistency listed in Table 1 or FIG. 5. In various embodiments, the marker comprises one, two, three, four, five, six, or more, or all of the genes with about 100% consistency listed in Table 1 or FIG. 5. In various embodiments, the marker comprises one, two, three, four, five, six, or more, or all of the PCS1 SEGs (SubtypeID=1) listed in Table 1 or FIG. 5. In various embodiments, the marker comprises one, two, three, four, five, six, or more, or all of the PCS2 SEGs (SubtypeID=2) listed in Table 1 or FIG. 5. In various embodiments, the marker comprises one, two, three, four, five, six, or more, or all of the PCS3 SEGs (SubtypeID=3) listed in Table 1 or FIG. 5.

In various embodiments, the marker comprises one, two, three, four, five, six, or more, or all of STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45. In various embodiments, the marker comprises STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and/or C16orf45, or a combination thereof.

In various embodiments, non-limiting examples of PCS1's marker expression changes, PCS2's marker expression changes, and PCS3's marker expression changes are shown in FIG. 5 or Table 1.

In various embodiments, the marker for the subtype comprises an increased expression level in one, two, three, four, five, six, or more, or all of the PCS1 SEGs (SubtypeID=1) listed in Table 1 or FIG. 5, and/or a decreased or insignificantly changed expression level in one, two, three, four, five, six, or more, or all of the non-PCS1 SEGs (SubtypeID≠1) listed in Table 1 or FIG. 5.

In various embodiments, the marker for the subtype comprises an increased expression level in one, two, three, four, five, six, or more, or all of STMN1, MCM4, CCNB1, CDC6, CDKN3, EZH2, TPX2, FOXM1, KIF11, HMMR, MKI67, and KNTC1; and/or a decreased or insignificantly changed expression level in one, two, three, four, five, six, or more, or all of RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45.

In various embodiments, the marker for the subtype comprises an increased expression level in one, two, three, four, five, six, or more, or all of the PCS2 SEGs (SubtypeID=2) listed in Table 1 or FIG. 5, and/or a decreased or insignificantly changed expression level in one, two, three, four, five, six, or more, or all of the non-PCS2 SEGs (SubtypeID≠2) listed in Table 1 or FIG. 5.

In various embodiments, the marker for the subtype comprises an increased expression level in one, two, three, four, five, six, or more, or all of RAB3B, SLC4A4, ANK3, GJB1, and SLC12A2; and/or a decreased or insignificantly changed expression level in one, two, three, four, five, six, or more, or all of STMN1, MCM4, CCNB1, CDC6, CDKN3, EZH2, TPX2, FOXM1, KIF11, HMMR, MKI67, KNTC1, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45.

In various embodiments, the marker for the subtype comprises an increased expression level in one, two, three, four, five, six, or more, or all of the PCS3 SEGs (SubtypeID=3) listed in Table 1 or FIG. 5, and/or a decreased or insignificantly changed expression level in one, two, three, four, five, six, or more, or all of the non-PCS3 SEGs (SubtypeID≠3) listed in Table 1 or FIG. 5.

In various embodiments, the marker for the subtype comprises an increased expression level in one, two, three, four, five, six, or more, or all of CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45; and/or a decreased or insignificantly changed expression level in one, two, three, four, five, six, or more, or all of STMN1, MCM4, CCNB1, CDC6, CDKN3, EZH2, TPX2, FOXM1, KIF11, HMMR, MKI67, KNTC1, RAB3B, SLC4A4, ANK3, GJB1, and SLC12A2.

In various embodiments, the cancer is prostate cancer (PC), low grade PC, high grade PC, benign PC, aggressive PC, primary PC, secondary PC, luminal PC, basal PC, metastatic PC, castration-resistant PC (CRPC), recurrent PC, or non-recurrent PC, or a combination thereof.

In various embodiments, the therapeutic agent is a nucleic acid, DNA, RNA, peptide, protein, antibody, aptamer, or small molecule, or a combination thereof. In various embodiments, the therapeutic agent is an antiandrogen, an androgen receptor (AR) antagonist, a selective AR modulator, or an androgen synthesis inhibitor, or a combination thereof. In various embodiments, the antiandrogen is flutamide, nilutamide, bicalutamide, enzalutamide, or apalutamide, or any of their functional equivalents, analogs, derivatives or salts. In various embodiments, the therapeutic agent is a Src signaling inhibitor, a Src family tyrosine kinase inhibitor, or a Bcr-Abl tyrosine kinase inhibitor, or a combination thereof. In various embodiments, the Src signaling inhibitor is imatinib, bafetinib, nilotinib, dasatinib, bosutinib, or ponatinib, or any of their functional equivalents, analogs, derivatives or salts. In various embodiments, the therapeutic agent is a mitotic inhibitor. In various embodiments, the mitotic inhibitor is taxane, paclitaxel, docetaxel, or cabazitaxel, or any of their functional equivalents, analogs, derivatives or salts.

In various embodiments, the subtype is PCS1, PCS2, or PCS3.

In various embodiments, the subtype is PCS1, and the administered therapeutic agent is an antiandrogen, an androgen receptor (AR) antagonist, a selective AR modulator, or an androgen synthesis inhibitor, or a combination thereof. In some embodiments, the subtype is PCS1, and the administered therapeutic agent is a mitotic inhibitor. In some embodiments, the subtype is PCS1, and the administered therapeutic agent is docetaxel, or a functional equivalent, analog, derivative or salt of docetaxel, or a combination thereof.

In one embodiment the subtype is PCS1 and the subject is administered DNA damaging agents including but not limited to cisplatin and poly ADP ribose polymerase (PARP) inhibitors.

In one embodiment, the subtype is PCS1 and the subject is not administered an antiandrogen agent. In one embodiment, the subtype is PCS1 and the subject is not administered enzalutamide.

In further embodiments, the subtype is PCS1, and the method comprises instructing, directing, or informing the subject not to receive or preventing the subject from receiving a Src signaling inhibitor, a Src family tyrosine kinase inhibitor, or a Bcr-Abl tyrosine kinase inhibitor. In some embodiments, the subtype is PCS1, and the method comprises instructing, directing, or informing the subject not to receive or preventing the subject from receiving dasatinib, or a functional equivalent, analog, derivative or salt of dasatinib.

In further embodiments, the subtype is PCS1, and the method comprises instructing, directing, or informing the subject not to receive or preventing the subject from receiving a mitotic inhibitor. In some embodiments, the subtype is PCS1, and the method comprises instructing, directing, or informing the subject not to receive or preventing the subject from receiving docetaxel, or a functional equivalent, analog, derivative or salt of docetaxel.

In various embodiments, the subtype is PCS2, and the administered therapeutic agent is an antiandrogen, an androgen receptor (AR) antagonist, a selective AR modulator, or an androgen synthesis inhibitor, or a combination thereof. In some embodiments, the subtype is PCS2, and the administered therapeutic agent is enzalutamide, or a functional equivalent, analog, derivative or salt of enzalutamide, or a combination thereof.

In further embodiments, the subtype is PCS2, and the method comprises instructing, directing, or informing the subject not to receive or preventing the subject from receiving a Src signaling inhibitor, a Src family tyrosine kinase inhibitor, or a Bcr-Abl tyrosine kinase inhibitor. In some embodiments, the subtype is PCS2, and the method comprises instructing, directing, or informing the subject not to receive or preventing the subject from receiving dasatinib, or a functional equivalent, analog, derivative or salt of dasatinib.

In various embodiments, the subtype is PCS2, and the administered therapeutic agent is a mitotic inhibitor. In some embodiments, the subtype is PCS2, and the administered therapeutic agent is docetaxel, or a functional equivalent, analog, derivative or salt of docetaxel, or a combination thereof.

In further embodiments, the subtype is PCS3, and the method comprises instructing, directing, or informing the subject not to receive or preventing the subject from receiving an antiandrogen, an androgen receptor (AR) antagonist, a selective AR modulator, or an androgen synthesis inhibitor. In some embodiments, the subtype is PCS3, and the method comprises instructing, directing, or informing the subject not to receive or preventing the subject from receiving enzalutamide, or a functional equivalent, analog, derivative or salt of enzalutamide.

In various embodiments, the subtype is PCS3, and the administered therapeutic agent is a Src signaling inhibitor, a Src family tyrosine kinase inhibitor, c-Kit receptor inhibitors, ephrin receptor inhibitors or a Bcr-Abl tyrosine kinase inhibitor, or a combination thereof. In some embodiments, the subtype is PCS3, and the administered therapeutic agent is dasatinib, or a functional equivalent, analog, derivative or salt of dasatinib, or a combination thereof.

In further embodiments, the subtype is PCS3, and the method comprises instructing, directing, or informing the subject not to receive or preventing the subject from receiving a mitotic inhibitor. In some embodiments, the subtype is PCS3, and the method comprises instructing, directing, or informing the subject not to receive or preventing the subject from receiving docetaxel, or a functional equivalent, analog, derivative or salt of docetaxel.

In various embodiments, the present invention provides a method for treating PCS1 in a subject. The method comprises: providing a therapeutic agent; and administering a therapeutically effective amount of the therapeutic agent to the subject, thereby treating PCS1 in the subject. In some embodiments, the therapeutic agent is an antiandrogen, an androgen receptor (AR) antagonist, a selective AR modulator, or an androgen synthesis inhibitor, or a combination thereof. In some embodiments, the therapeutic agent is a mitotic inhibitor.

In various embodiments, the present invention provides a method for treating PCS2 in a subject. The method comprises: providing a therapeutic agent; and administering a therapeutically effective amount of the therapeutic agent to the subject, thereby treating PCS2 in the subject. In some embodiments, the therapeutic agent is an antiandrogen, an androgen receptor (AR) antagonist, a selective AR modulator, or an androgen synthesis inhibitor, or a combination thereof. In some embodiments, the therapeutic agent is a mitotic inhibitor.

In various embodiments, the present invention provides a method for treating PCS3 in a subject. The method comprises: providing a therapeutic agent; and administering a therapeutically effective amount of the therapeutic agent to the subject, thereby treating PCS3 in the subject. In some embodiments, the therapeutic agent is a Src signaling inhibitor, a Src family tyrosine kinase inhibitor, or a Bcr-Abl tyrosine kinase inhibitor, or a combination thereof.

In various embodiments, the present invention provides a method for treating a cancer subtype in a subject. The method comprises: ordering a diagnostic test to determine if the subject has a cancer subtype; and administering a therapeutically effective amount of a therapeutic agent to the subject who has been diagnosed with the cancer subtype, thereby treating the cancer subtype in the subject. In various embodiments, the cancer subtype is PCS1, PCS2, or PCS3. In some embodiments, the diagnostic test is performed via methods as described in the present invention. In various embodiments, the method may further comprise providing the therapeutic agent.

In various embodiments, the present invention provides a method for treating PCS1 in a subject. The method comprises ordering: a diagnostic test to determine if the subject has PCS1; and administering a therapeutically effective amount of a therapeutic agent to the subject who has been diagnosed with PCS1, thereby treating PCS1 in the subject. In some embodiments, the diagnostic test is performed via methods as described in the present invention. In various embodiments, the method may further comprise providing the therapeutic agent. In some embodiments, the therapeutic agent is an antiandrogen, an androgen receptor (AR) antagonist, a selective AR modulator, or an androgen synthesis inhibitor, or a combination thereof. In some embodiments, the therapeutic agent is a mitotic inhibitor.

In various embodiments, the present invention provides a method for treating PCS2 in a subject. The method comprises ordering: a diagnostic test to determine if the subject has PCS2; and administering a therapeutically effective amount of a therapeutic agent to the subject who has been diagnosed with PCS2, thereby treating PCS2 in the subject. In some embodiments, the diagnostic test is performed via methods as described in the present invention. In various embodiments, the method may further comprise providing the therapeutic agent. In some embodiments, the therapeutic agent is an antiandrogen, an androgen receptor (AR) antagonist, a selective AR modulator, or an androgen synthesis inhibitor, or a combination thereof. In some embodiments, the therapeutic agent is a mitotic inhibitor.

In various embodiments, the present invention provides a method for treating PCS3 in a subject. The method comprises ordering: a diagnostic test to determine if the subject has PCS3; and administering a therapeutically effective amount of a therapeutic agent to the subject who has been diagnosed with PCS3, thereby treating PCS3 in the subject. In some embodiments, the diagnostic test is performed via methods as described in the present invention. In various embodiments, the method may further comprise providing the therapeutic agent. In some embodiments, the therapeutic agent is a Src signaling inhibitor, a Src family tyrosine kinase inhibitor, or a Bcr-Abl tyrosine kinase inhibitor, or a combination thereof.

Various embodiments of the present invention provide a method of selecting and/or excluding a therapeutic agent for a subject with a cancer. The method comprises: providing a subject with a cancer classified into a subtype utilizing a classification method disclosed herein; and selecting for the subject a therapeutic agent that specifically benefits the subtype and/or excluding for the subject a therapeutic agent that does not benefit the subtype. In accordance with the present invention, "selecting" a therapy may be used interchangeably with "choosing", "ordering", or "prescribing" a therapy.

Various embodiments of the present invention provide a method of selecting a therapeutic agent for a subject with a cancer. The method comprises: providing a subject with a cancer classified into a subtype utilizing a classification method disclosed herein; and selecting for the subject a therapeutic agent that specifically benefits the subtype.

Various embodiments of the present invention provide a method of excluding a therapeutic agent for a subject with a cancer. The method comprises: providing a subject with a cancer classified into a subtype utilizing a classification method disclosed herein; and excluding for the subject a therapeutic agent that does not benefit the subtype.

In various embodiments, the subtype is PCS1, and the selected therapeutic agent is an antiandrogen, an androgen receptor (AR) antagonist, a selective AR modulator, or an androgen synthesis inhibitor, or a combination thereof. In various embodiments, the subtype is PCS1, and the selected therapeutic agent is a mitotic inhibitor. In various embodiments, the subtype is PCS2, and the selected therapeutic agent is an antiandrogen, an androgen receptor (AR) antagonist, a selective AR modulator, or an androgen synthesis inhibitor, or a combination thereof. In various embodiments, the subtype is PCS2, and the selected therapeutic agent is a mitotic inhibitor. In various embodiments, the subtype is PCS3, and the selected therapeutic agent a Src signaling inhibitor, a Src family tyrosine kinase inhibitor, or a Bcr-Abl tyrosine kinase inhibitor, or a combination thereof. In some embodiments, the method further comprises instructing, directing, or informing the subject to receive the selected therapeutic agent. In some embodiments, the method further comprises administering the selected therapeutic agent to the subject.

In various embodiments, the subtype is PCS1, and the excluded therapeutic agent is a Src signaling inhibitor, a Src family tyrosine kinase inhibitor, or a Bcr-Abl tyrosine kinase inhibitor, or a combination thereof. In various embodiments, the subtype is PCS1, and the excluded therapeutic agent is a mitotic inhibitor. In various embodiments, the subtype is PCS2, and the excluded therapeutic agent is a Src signaling inhibitor, a Src family tyrosine kinase inhibitor, or a Bcr-Abl tyrosine kinase inhibitor, or a combination thereof. In various embodiments, the subtype is PCS3, and the excluded therapeutic agent is an antiandrogen, an androgen receptor (AR) antagonist, a selective AR modulator, or an androgen synthesis inhibitor, or a combination thereof. In various embodiments, the subtype is PCS3, and the excluded therapeutic agent is a mitotic inhibitor. In some embodiments, the method further comprises instructing, directing, or informing the subject not to receive the excluded therapeutic agent. In some embodiments, the method further comprises preventing the subject from receiving the excluded therapeutic agent.

In various embodiments, the antiandrogen is flutamide, nilutamide, bicalutamide, enzalutamide, or apalutamide, or any of their functional equivalents, analogs, derivatives or salts. In some embodiments, the antiandrogen is enzalutamide, a functional equivalent, analog, derivative or salt of enzalutamide, or a combination thereof. In various embodiments, the Src signaling inhibitor is imatinib, bafetinib, nilotinib, dasatinib, bosutinib, or ponatinib, or any of their functional equivalents, analogs, derivatives or salts. In some embodiments, the Src signaling inhibitor is dasatinib, a functional equivalent, analog, derivative or salt of dasatinib, or a combination thereof. In various embodiments, the mitotic inhibitor is taxane, paclitaxel, docetaxel, or cabazitaxel, or any of their functional equivalents, analogs, derivatives or salts. In some embodiments, the mitotic inhibitor is docetaxel, a functional equivalent, analog, derivative or salt of docetaxel, or a combination thereof.

Typical dosages of a therapeutically effective amount of a therapeutic agent disclosed herein can be in the ranges recommended by the manufacturer where known therapeutic molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the therapeutic agent may be administered once a day (SID/QD), twice a day (BID), three times a day (TID), four times a day (QID), or more, so as to administer an effective amount of the therapeutic agent to the subject, where the effective amount is any one or more of the doses described herein.

In various embodiments, the therapeutic agent is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$, or a combination thereof. In various embodiments, the therapeutic agent is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In various embodiments, the therapeutic agent is administered once, twice, three or more times. In various embodiments, the therapeutic agent is administered about 1-3 times per day, 1-7 times per week, 1-9 times per month, or 1-12 times per year. In various embodiments, the therapeutic agent is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mg/kg" refers to mg per kg body weight of the subject, and "mg/m2" refers to mg per m$^2$ body surface area of the subject. In certain embodiments, the therapeutic agent is administered to a human.

In various embodiments, the effective amount of the therapeutic agent is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg/day, or a combination thereof. In various embodiments, the effective amount of the therapeutic agent is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/m$^2$/day, or a combination thereof. In various embodiments, the effective amount of the therapeutic agent is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg/day, or a combination thereof. In various embodiments, the effective amount of the therapeutic agent is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$/day, or a combination thereof. Here, "µg/kg/day" or "mg/kg/day" refers to µg or mg per kg body weight of the subject per day, and "µg/m2/day" or "mg/m2/day" refers to µg or mg per m2 body surface area of the subject per day.

In some embodiments, the therapeutic agent may be administered at the prevention stage of a condition (i.e., when the subject has not developed the condition but is likely to or in the process to develop the condition). In other embodiments, the therapeutic agent may be administered at the treatment stage of a condition (i.e., when the subject has already developed the condition). As a non-limiting example, the target condition is prostate cancer (PC), PCS1, PCS2, or PCS3. In this exemplar situation, the patient may be treated with the methods described herein when the patient has not yet developed PCS1, PCS2, or PCS3, or is likely to develop PCS1, PCS2, or PCS3, or is in the process of developing PCS1, PCS2, or PCS3, or has already developed PCS1, PCS2, or PCS3.

In accordance with the invention, the therapeutic agent may be administered using the appropriate modes of administration, for instance, the modes of administration recommended by the manufacturer for each of the therapeutic agent. In accordance with the invention, various routes may be utilized to administer the therapeutic agent of the claimed methods, including but not limited to intravascular, intravenous, intraarterial, intratumoral, intramuscular, subcutaneous, intraperitoneal, intranasal, or oral.

In various embodiments, the subject is a human. In various embodiments, the subject is a mammalian subject including but not limited to human, monkey, ape, dog, cat, cow, horse, goat, pig, rabbit, mouse and rat.

In various embodiments, the sample or biological sample is a cancer or tumor sample. In various embodiments, the sample or biological sample comprises a tumor cell or a tumor tissue. In various embodiments, the sample or biological sample comprises a tumor biopsy or a tumor sample.

In various embodiments, the reference sample is a non-neoplastic sample. In some embodiments, the non-neoplastic sample is obtained from the subject itself. In other embodiments, the non-neoplastic sample is obtained from another individual. In various embodiments, the individual does not have prostate cancer or prostate diseases. In various embodiments, the individual and the subject belong to the same species, for example, human. In various embodiments, the reference value is obtained from one or more non-neoplastic samples.

In various embodiments, changes (e.g., increases and/or decreases) in gene expression levels relative to reference samples or values are detected by: contacting the sample with detection agents that specifically bind to target genes' mRNAs and/or proteins; and detecting the binding levels between the detection agents and the target genes' mRNAs and/or proteins. In various embodiments, the sample is assayed to detect changes in mRNA expression levels relative to reference samples or values. In various embodiments, the sample is assayed to detect changes in protein expression levels relative to reference samples or values. Proteins can be detected by various techniques such as IHC, Western blots and protein arrays; and genes and mRNA can be detected by genotyping assays, PCR, Reverse transcription PCR, real-time PCR, microarray, DNA sequencing, and RNA sequencing techniques.

In various embodiments, the detection agents are oligonucleotide probes, nucleic acids, DNAs, RNAs, aptamers, peptides, proteins, antibodies, avimers, or small molecules, or a combination thereof. In various embodiments, changes (e.g., increases and/or decreases) in gene expression levels relative to reference samples or values are detected by using a microarray. In some embodiments, the microarray is an oligonucleotide microarray, DNA microarray, cDNA microarrays, RNA microarray, peptide microarray, protein microarray, or antibody microarray, or a combination thereof.

Various embodiments of the present invention also provide a composition for classifying, and/or diagnosing, and/or prognosing, and/or treating cancers and cancer subtypes. In various embodiments, the cancer is prostate cancer (PC), low grade PC, high grade PC, benign PC, aggressive PC, primary PC, secondary PC, luminal PC, basal PC, metastatic PC, castration-resistant PC (CRPC), recurrent PC, or non-recurrent PC, or a combination thereof. In various embodiments, the subtype is PCS1, PCS2, or PCS3. In various embodiments, the composition comprises one or more detection agents that specifically bind to one or more SEGs' mRNAs and/or proteins. In various embodiments, the composition further comprises a biological sample from a subject. In various embodiments, the subject desires a diagnosis on whether he/she has a cancer or a cancer subtype, or desires a classification of his/her cancer in to a cancer subtype, or desires a prognosis of the clinical outcome of his/her cancer, or desires a prognosis of the drug resistance or response of his/her cancer.

Expression Pattern Assay—RNA

In various embodiments, determining an expression pattern of SEGs in the biological sample comprises assaying mRNA levels. In various embodiments, assaying mRNA levels comprises using RNA sequencing, northern blot, in situ hybridization, hybridization array, serial analysis of gene expression (SAGE), reverse transcription PCR, real-time PCR, real-time reverse transcription PCR, quantitative PCR, or microarray, or a combination thereof.

In various embodiments, assaying mRNA levels comprises contacting the biological sample with polynucleotide probes capable of specifically hybridizing to mRNA of one or more SEGs and thereby forming probe-target hybridization complexes.

Hybridization-based RNA assays include, but are not limited to, traditional "direct probe" methods such as, northern blot or in situ hybridization (e.g., Angerer (1987) Meth. Enzymol 152: 649). The methods can be used in a wide variety of formats including, but not limited to, substrate (e.g. membrane or glass) bound methods or array-based approaches. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases. Hybridization protocols suitable for use with the methods of the invention are described, e.g., in Albertson (1984) EMBO J. 3: 1227-1234; Pinkel (1988) Proc. Natl. Acad. Sci. USA 85: 9138-9142; EPO Pub. No. 430,402; Methods in Molecular Biology, Vol. 33: In situ Hybridization Protocols, Choo, ed., Humana Press, Totowa, N.J. (1994), Pinkel, et al. (1998) Nature Genetics 20: 207-211, and/or Kallioniemi (1992) Proc. Natl Acad Sci USA 89:5321-5325 (1992). In some applications, it is necessary to block the hybridization capacity of repetitive sequences. Thus, in some embodiments, tRNA, human genomic DNA, or Cot-I DNA is used to block non-specific hybridization.

In various embodiments, assaying mRNA levels comprises contacting the biological sample with polynucleotide primers capable of specifically hybridizing to mRNAs of SEGs listed in Table 1, forming primer-template hybridization complexes, and performing a PCR reaction. In some embodiments, the polynucleotide primers comprises about 15-45, 20-40, or 25-35 bp sequences that are identical (for forward primers) or complementary (for reverse primers) to sequences of SEGs listed in Table 1. As a non-liming example, the polynucleotide primers for STMN1 (e.g., NM_203401, *Homo sapiens* stathmin 1 (STMN1), transcript variant 1, mRNA, 1730 bp) can comprise sequences that are identical (for forward primers) or complementary (for reverse primers) to STMN1's bp 1-20, 5-25, 10-30, 15-35, 20-40, 25-45, 30-50, so on and so forth, until the end of STMN, bp 1690-1710, 1695-1715, 1700-1720, 1705-1725, 1710-1730. While not listed here exhaustively because of the space, all these polynucleotide primers for STMN1 and other SEGs listed in Table 1 can be used in the present invention. In various embodiments, the polynucleotide primers are labeled with radioisotopes or fluorescent molecules. As the labeled primers emit radio or fluorescent signals, the PCR products containing the labeled primers can be detected and analyzed with a variety of imaging equipment.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, A Guide to Methods and Applications, Academic Press, Inc. N.Y.). Measurement of DNA copy number at microsatellite loci using quantitative PCR anlaysis is described in Ginzonger, et al. (2000) Cancer Research 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green. Other suitable amplification methods include, but are not limited to, ligase chain reaction (LCR) (see Wu and Wallace (1989) Genomics 4: 560, Landegren, et al. (1988) Science 241: 1077, and Barringer et al. (1990) Gene 89: 117), transcription amplification (Kwoh, et al. (1989) Proc. Natl. Acad. Sci. USA 86: 1173), self-sustained sequence replication (Guatelli, et al. (1990) Proc. Nat. Acad. Sci. USA 87: 1874), dot PCR, and linker adapter PCR, etc.

Expression Level Assay—Protein

In various embodiments, determining an expression pattern of SEGs in a biological sample comprises assaying protein levels. In various embodiments, assaying a protein level comprises using western blot, enzyme-linked immunosorbent assay (ELISA), radioimmunoassay, or mass spectrometry, or a combination thereof.

In various embodiments, assaying protein levels comprises contacting the biological sample with antibodies capable of specifically binding to proteins encoded by SEGs listed in Table 1 and thereby forming antigen-antibody complexes. In the methods and assays of the invention, the expression levels of proteins encoded by SEGs listed in Table 1, or fragments or variants thereof can be determined using antibodies specific for those individual proteins or fragments or variants thereof and detecting immunospecific binding of each antibody to its respective cognate biomarker protein.

Antibodies, both polyclonal and monoclonal, can be produced by a skilled artisan either by themselves using well known methods or they can be manufactured by service providers who specialize making antibodies based on known protein sequences. In the present invention, the protein sequences of SEGs listed in Table 1 are known and thus production of antibodies against them is a matter of routine.

For example, production of monoclonal antibodies can be performed using the traditional hybridoma method by first immunizing mice with an antigen which may be an isolated protein of choice or fragment thereof (for example, a protein encode by a SEG listed in Table 1, or a fragment thereof or a variant thereof) and making hybridoma cell lines that each produce a specific monoclonal antibody. The antibodies secreted by the different clones are then assayed for their ability to bind to the antigen using, e.g., ELISA or Antigen Microarray Assay, or immuno-dot blot techniques. The antibodies that are most specific for the detection of the protein of interest can be selected using routine methods and using the antigen used for immunization and other antigens as controls. The antibody that most specifically detects the desired antigen and protein and no other antigens or proteins are selected for the processes, assays and methods described herein. The best clones can then be grown indefinitely in a suitable cell culture medium. They can also be injected into mice (in the peritoneal cavity, surrounding the gut) where they produce an antibody-rich ascites fluid from which the antibodies can be isolated and purified. The antibodies can be purified using techniques that are well known to one of ordinary skill in the art.

Any suitable immunoassay method may be utilized, including those which are commercially available, to determine the expression level of a SEG protein or a variant thereof assayed according to the invention. Extensive discussion of the known immunoassay techniques is not required here since these are known to those of skill in the art. Typical suitable immunoassay techniques include sandwich enzyme-linked immunoassays (ELISA), radioimmunoassays (RIA), competitive binding assays, homogeneous assays, heterogeneous assays, etc.

For example, in the assays of the invention, "sandwich-type" assay formats can be used. An alternative technique is the "competitive-type" assay. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule.

The antibodies can be labeled. In some embodiments, the detection antibody is labeled by covalently linking to an enzyme, label with a fluorescent compound or metal, label with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease.

The antibody can be attached to a surface. Examples of useful surfaces on which the antibody can be attached for the purposes of detecting the desired antigen include nitrocellulose, PVDF, polystyrene, and nylon.

In some embodiments of the processes, assays and methods described herein, detecting the level of antibodies reactive to a SEG protein or a variant thereof includes contacting the sample from the cancer patient with an antibody or a fragment thereof that specifically binds a SEG protein or a variant thereof, forming an antibody-protein complex between the antibody and the SEG protein or the variant thereof present in the sample, washing the sample to remove the unbound antibody, adding a detection antibody that is labeled and is reactive to the antibody bound to the SEG protein or a variant thereof in the sample, washing to remove the unbound labeled detection antibody and converting the label to a detectable signal, wherein the detectable signal is indicative of the level of SEG protein or a variant thereof in the sample from the patient. In some embodiments, the effector component is a detectable moiety selected from the group consisting of a fluorescent label, a radioactive compound, an enzyme, a substrate, an epitope tag, electron-dense reagent, biotin, digonigenin, hapten and a combination thereof. In some embodiments, the detection antibody is labeled by covalently linking to an enzyme, labeled with a fluorescent compound or metal, labeled with a chemiluminescent compound. The level of the SEG protein may be obtained by assaying a light scattering intensity resulting from the formation of an antibody-protein complex formed by a reaction of the SEG protein in the sample with the antibody, wherein the light scattering intensity of at least 10% above a control light scattering intensity indicates the likelihood of chemotherapy resistance.

Reference Value of Expression Level

Various methods described herein may compare a SEG's expression level in a subject's biological sample to a predetermined reference value of the SEG. In various embodiments, a SEG's reference value of expression level is the SEG's median or mean expression level from all tumor samples in the discovery dataset. In various embodiments, a SEG's reference value of expression level is the SEG's median or mean expression level from all PC samples in the discovery dataset. In various embodiments, a SEG's reference value of expression level is the SEG's median or mean expression level from all tumor samples in the validation dataset. In various embodiments, a SEG's reference value of expression level is the SEG's median or mean expression level from all PC samples in the validation dataset. In various embodiments, a SEG's reference value of expression level is the SEG's median or mean expression level from non-cancerous, non-tumorous, or non-neoplastic cells or tissues. In accordance with the present invention, SEGs include but are not limited to those listed in Table 1.

Reference values may be obtained by various methods known in the field. For example, one or more biopsies from one cancer patient' tumor (hereinafter "Tumor-1") may be collected, processed and analyzed to obtain the expression level of one SEG (hereinafter "Gene-1") in this tumor (hereinafter "Expression-Tumor-1-Gene-1"). The same step is used to obtain Gene-1's expression levels in another 10, 100, 200, 300, 400, 500, 600, 700, 800, 900, 1000 or more cancer patients' tumors (hereinafter "Tumor-N"), that is, "Expression-Tumor-N-Gene-1" (N is 1, 2, 3, 4, 5, 6, 7, ... ). Then, Gene-1's median or mean expression level from all tumors may be used as the reference value of Gene-1 (hereinafter "REF-Gene-1"), to which Gene-1's expression in a subject's biological sample is compared to so as to determine if Gene-1's expression is increased (high) or decreased (low) in the subject's biological sample. In other words, REF-Gene-1 is the median or mean of Expression-Tumor-N-Gene-1. Similar steps may be used to obtain another 5, 10, 15, 20, 25, 30, 35, 40, 45, 50, 55, 60, 65, 70, 75, 80, 85, 90, 95, 100, or more SEGs' reference values, that is, "REF-Gene-M" (M=1, 2, 3, 4, 5, 6, 7, ... ). In various embodiments, SEGs (i.e., Gene-M) are listed in Table 1. To determine the expression pattern of SEGs in a subject's biological sample, one may compare one, two, three, four, five, or more SEGs' expression levels to their respective reference values.

As used herein, "expression pattern", "expression profile" and "expression signature" are exchangeable terms referring to the specific combination or setting of one or more genes' high (increased) expressions and/or low (decreased) expressions relative to reference values. In various embodiments, the expression patterns of prostate cancer subtypes are the specific combinations of SEGs' high and low expressions. For non-limiting example, Table 1, FIG. 4 or FIG. 5 shows the expression patterns of PCS1, PCS2, and PCS3. Among the 37 SEGs shown in FIG. 5, those having high expressions relative to reference values are shown as dark gray, and those having low expressions relative to reference values are shown as light gray to white.

Various statistical methods, for example, a two-tailed student t-test with unequal variation, may be used to measure the differences in expression levels of a SEG between the subject's sample and a reference value of expression level generate by computer algorithm pooling many tumor samples, as described herein, for example, all the PC samples in the discovery dataset and/or validation dataset. Various statistical methods, for example, a two-tailed student t-test with unequal variation, may be used to measure the differences in expression levels of a SEG between the subject's sample and a control sample from a normal/healthy individual. Various statistical methods, for example, a two-tailed student t-test with unequal variation, may be used to measure the differences in expression levels of a SEG between the subject's sample and a reference value of expression level generate by computer algorithm pooling many control samples, as described herein. A significant difference may be achieved where the p value is equal to or less than 0.05.

In various embodiments, the expression level of a SEG or a variant thereof in the subject as compared to the reference value is higher by at least or about 5, 10, 15, 20, 25, 30, 35, 40, 45, 50, 55, 60, 65, 70, 75, 80, 85, 90, 95, or 100%. In various embodiments, the expression level of a SEG or a variant thereof in the subject as compared to the reference value is lower by at least or about 5, 10, 15, 20, 25, 30, 35, 40, 45, 50, 55, 60, 65, 70, 75, 80, 85, 90, 95, or 100%. In various embodiments, the expression level ratio between a SEG or a variant thereof in the subject and the reference value is at least or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 4:1, 5:1, 6:1, 7:1, 8:1, 9:1 or 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1. In various embodiments, the expression level ratio between the reference value and a SEG or a variant thereof in the subject is at least or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 4:1, 5:1, 6:1, 7:1, 8:1, 9:1 or 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

To provide aspects of the present disclosure, embodiments may employ any number of programmable processing devices that execute software or stored instructions. Physical processors and/or machines employed by embodiments of the present disclosure for any processing or evaluation may include one or more networked (Internet, cloud, WAN, LAN, satellite, wired or wireless (RF, cellular, WiFi, Bluetooth, etc.)) or non-networked general purpose computer systems, microprocessors, filed programmable gate arrays (FPGAs), digital signal processors (DSPs), micro-controllers, smart devices (e.g., smart phones), computer tablets, handheld computers, and the like, programmed according to the teachings of the exemplary embodiments. In addition, the devices and subsystems of the exemplary embodiments can be implemented by the preparation of application-specific integrated circuits (ASICs) or by interconnecting an appropriate network of conventional component circuits. Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, database management software, and the like. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, processing capabilities may be distributed across multiple processors for better performance, reliability, cost, or other benefits.

Common forms of computer-readable media may include, for example, a floppy disk, a flexible disk, a hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read. Such storage media can also be employed to store other types of data, e.g., data organized in a database, for access, processing, and communication by the processing devices.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Experimental Methods

Merging Transcriptome Datasets and Quality Control

To assemble a merged dataset from diverse microarray and high-throughput sequencing platforms, we applied a median-centering method followed by quantile scaling (MCQ; (You S, Cho C S, Lee I, Hood L, Hwang D, Kim W U. A systems approach to rheumatoid arthritis. PLoS One 2012; 7:e51508). Briefly, each dataset was normalized using the quantile method (Bolstad B M, Irizarry R A, Astrand M, Speed T P. A comparison of normalization methods for high density oligonucleotide array data based on variance and bias. Bioinformatics 2003; 19:185-93). Probes or transcripts were assigned to unique genes by mapping NCBI entrez gene IDs. Redundant replications for each probe and transcript were removed by selecting the one with the highest mean expression. Log 2 intensities for each gene were centered by the median of all samples in the dataset. Each of the matrices was then transformed into a single vector. The vectors for the matrices were scaled by the quantile method to avoid a bias toward certain datasets or batches with large variations from the median values. These scaled vectors were transformed back into the matrices. Finally, the matrices were combined by matching the gene IDs in the individual matrices, resulting in a merged dataset of 2,115 samples by 18,390 human genes. To evaluate the MCQ-based normalization strategy, we applied the XPN (cross platform normalization; Shabalin A A, Tjelmeland H, Fan C, Perou C M, Nobel A B. Merging two gene-expression studies via cross-platform normalization. Bioinformatics 2008; 24:1154-60) method to the same datasets and compared it with the merged data from MCQ. Multidimensional scaling (MDS) between samples was performed to assess batch effects. The same MCQ approach with the quantile method, or the single channel array normalization (SCAN) method (Piccolo S R, Sun Y, Campbell J D, Lenburg M E, Bild A H, Johnson W E. A single-sample microarray normalization method to facilitate personalized-medicine workflows. Genomics 2012; 100:337-44), was also applied for normalization and batch correction of data from the independent cohorts.

Computing Pathway Activation Score

We used the Z-score method to quantify pathway activation (Levine D M, Haynor D R, Castle J C, Stepaniants S B, Pellegrini M, Mao M, et al. Pathway and gene-set activation measurement from mRNA expression data: the tissue distribution of human pathways. Genome Biol 2006; 7:R93). Briefly, the Z-score was defined by the difference between the error-weighted mean of the expression values of the genes in a gene signature and the error-weighted mean of all genes in a sample after normalization. Z-scores were computed using each signature in the signature collection for each of the samples, resulting in a matrix of pathway activation scores.

Determination of the Optimal Number of Clusters

Non-negative matrix factorization (NMF) clustering with a consensus approach is useful to elucidate biologically meaningful classes (Carrasco D R, Tonon G, Huang Y, Zhang Y, Sinha R, Feng B, et al. High-resolution genomic profiles define distinct clinicopathogenetic subgroups of multiple myeloma patients. Cancer Cell 2006; 9:313-25). Thus, we applied the consensus NMF clustering method (Brunet J P, Tamayo P, Golub T R, Mesirov J P. Metagenes and molecular pattern discovery using matrix factorization. Proc Natl Acad Sci USA 2004; 101:4164-9) to identify the optimal number of clusters. NMF was computed 100 times for each rank k from 2 to 6, where k was a presumed number of subtypes in the dataset. For each k, 100 matrix factorizations were used to classify each sample 100 times. The consensus matrix with samples was used to assess how consistently sample-pairs cluster together. We then computed the cophenetic coefficients and silhouette scores for each k, to quantitatively assess global clustering robustness across the consensus matrix. The maximum peak of the cophenetic coefficient and silhouette score plots determined the optimal number of clusters.

Classification Using a 14-Pathway Classifier

We constructed a classifier, where a set of predictors consists of 14 pathways, using a naïve Bayes machine learning algorithm. For training the classifier, we used the pathway activation scores and subtype labels of the result of the NMF clustering process. We then computed the misclassification rate using stratified 10-fold cross validation. To assess performance, we adopted a 3-class classification as a 2-class classification (e.g., PCS1 vs. others) and computed the average area under the receiver operating characteristic (ROC) curves from all 3 of 2-class classifications. Finally, we applied the 14-pathway classifier to assign subtypes to the specimens.

Identifying Subtype-Enriched Genes

Wilcoxon rank-sum test and subsequent false discovery rate (FDR) correction with Storey's method (Storey J D. A direct approach to false discovery rates. J Roy Stat Soc B 2002; 64:479-98) were employed to identify differentially expressed genes between the subtypes. Genes were selected with FDR<0.001 and fold change>1.5, resulting in 428 subtype-enriched genes (SEG).

Development of a 37-Gene Diagnostic Panel

A random forest machine learning algorithm was employed to develop a diagnostic gene panel. For parameter estimation and training the model, we used the merged dataset. Initially, the model comprised of the 428 SEGs as a set of predictors and subtype label of the merged dataset was used as a response variable for model training. To verify the optimal leaf size, we compared the mean squared errors (MSE) obtained by classification of leaf sizes of 1 to 50 with 100 trees, resulting in an optimal leaf size of 1 for model training. We then permuted the values for each gene across every sample and measured how much worse MSE became after the permutation. Imposing a cutoff of importance score at 0.5, we selected the 37 genes for subtyping. From the computation of MSE growing 100 trees on 37 genes and on the 428 SEGs, the 37 genes we chose gave the same MSE as the full set of 428 genes. ROC curve analyses and 10-fold cross-validation were also conducted to assess the performance of a classification ensemble.

Statistical Analysis

We performed principal component analysis (PCA) and MDS for visualizing the samples to assess their distribution using pathway activation profiles. Wilcoxon rank-sum statistics were used to test for significant differences in pathway activation scores between the subtypes. Kaplan-Meier analysis, Cox proportional hazard regression, and the $\chi^2$ test were performed to examine the relationship(s) between clinical variables and subtype assignment. The OR test using dichotomized variables was conducted to investigate relationships between different subtyping schemes. The MATLAB package (Mathworks) and the R package (v.3.1 http://www.r-projectorg/) were used for all statistical tests.

A Prostate Cancer Gene Expression Atlas

To achieve adequate power for a robust molecular classification of prostate cancer, we initially collected 50 prostate cancer datasets from three public databases: Gene Expression Omnibus (GEO; http://www.ncbi.nlm.nih.gov/geo), ArrayExpress (http://www.ebi.ac.uk/arrayexpress), and the UCSC Cancer Genomics Browser (https://genome-cancer.ucsc.edu) and selected 38 data-sets (Table 2), in which the numbers of samples are larger than 10 and where over 10,000 genes were measured (FIG. 1A).

TABLE 2

List of gene expression datasets included in the analysis of the DISC cohort

| Data Source ID. | Total # of Genes in Array | Total # of Samples | # of Benign | # of Primary | # of CRPC/Met |
|---|---|---|---|---|---|
| GSE6099 | 10137 | 104 | 52 | 32 | 20 |
| GSE6752 | 12418 | 31 | 0 | 10 | 21 |
| GSE6956 | 13020 | 89 | 20 | 69 | 0 |
| GSE8218 | 13020 | 148 | 71 | 78 | 0 |
| GSE32269 | 13020 | 51 | 0 | 22 | 29 |
| GSE2443 | 13020 | 20 | 0 | 20 | 0 |
| GSE25136 | 13020 | 79 | 0 | 79 | 0 |
| GSE7055 | 13020 | 57 | 0 | 57 | 0 |
| E-SMDB-2486 | 13888 | 112 | 41 | 62 | 9 |
| GSE3933 | 15468 | 112 | 41 | 62 | 9 |
| GSE15484 | 16110 | 65 | 13 | 52 | 0 |
| GSE6919 | 16386 | 160 | 72 | 63 | 25 |
| GSE14206 | 16548 | 67 | 14 | 53 | 0 |
| GSE6811 | 16625 | 35 | 0 | 24 | 11 |
| E-MTAB-154 | 16709 | 48 | 0 | 48 | 0 |
| GSE12378 | 17406 | 39 | 3 | 36 | 0 |
| GSE29079 | 17406 | 95 | 48 | 47 | 0 |
| GSE41408 | 17406 | 48 | 0 | 48 | 0 |
| GSE30521 | 17839 | 23 | 5 | 18 | 0 |
| E-TABM-26 | 18804 | 57 | 13 | 44 | 0 |
| GSE8511 | 18848 | 41 | 16 | 12 | 13 |
| GSE11682 | 19075 | 34 | 17 | 17 | 0 |
| GSE41619 | 19497 | 14 | 0 | 0 | 14 |
| GSE35988 | 19596 | 119 | 28 | 59 | 32 |
| GSE27616 | 19751 | 13 | 4 | 5 | 4 |
| GSE38241 | 19751 | 39 | 21 | 0 | 18 |
| TCGA (2013 Apr. 24) | 20437 | 220 | 44 | 176 | 0 |
| GSE3325 | 20678 | 19 | 6 | 7 | 6 |
| GSE26910 | 20678 | 12 | 6 | 6 | 0 |
| GSE17951 | 20678 | 154 | 81 | 73 | 0 |
| GSE32448 | 20678 | 80 | 40 | 40 | 0 |
| GSE2109 | 20678 | 56 | 0 | 56 | 0 |
| GSE16120 | 22153 | 65 | 14 | 51 | 0 |
| GSE21034 | 22261 | 179 | 29 | 131 | 19 |

TABLE 2-continued

List of gene expression datasets included in the analysis of the DISC cohort

| Data Source ID. | Total # of Genes in Array | Total # of Samples | # of Benign | # of Primary | # of CRPC/Met |
|---|---|---|---|---|---|
| GSE40272 | 24013 | 153 | 52 | 101 | 0 |
| GSE32571 | 24319 | 98 | 39 | 59 | 0 |
| GSE29650 | 24384 | 30 | 0 | 0 | 30 |
| GSE28680 | 27317 | 24 | 4 | 20 | 0 |

Figure 1C:
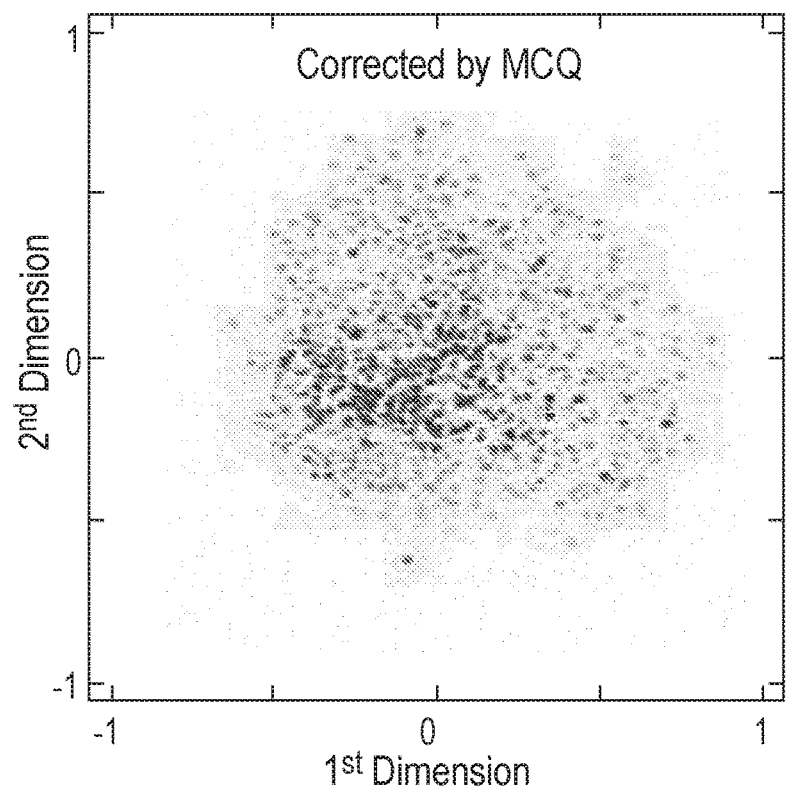
Figure 1C:
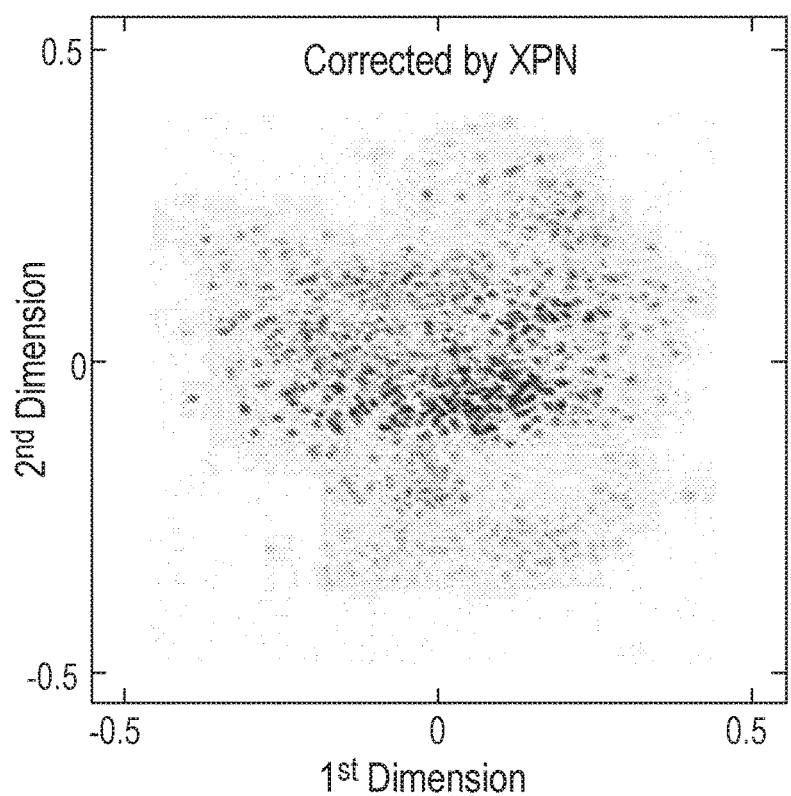
Figure 1D:
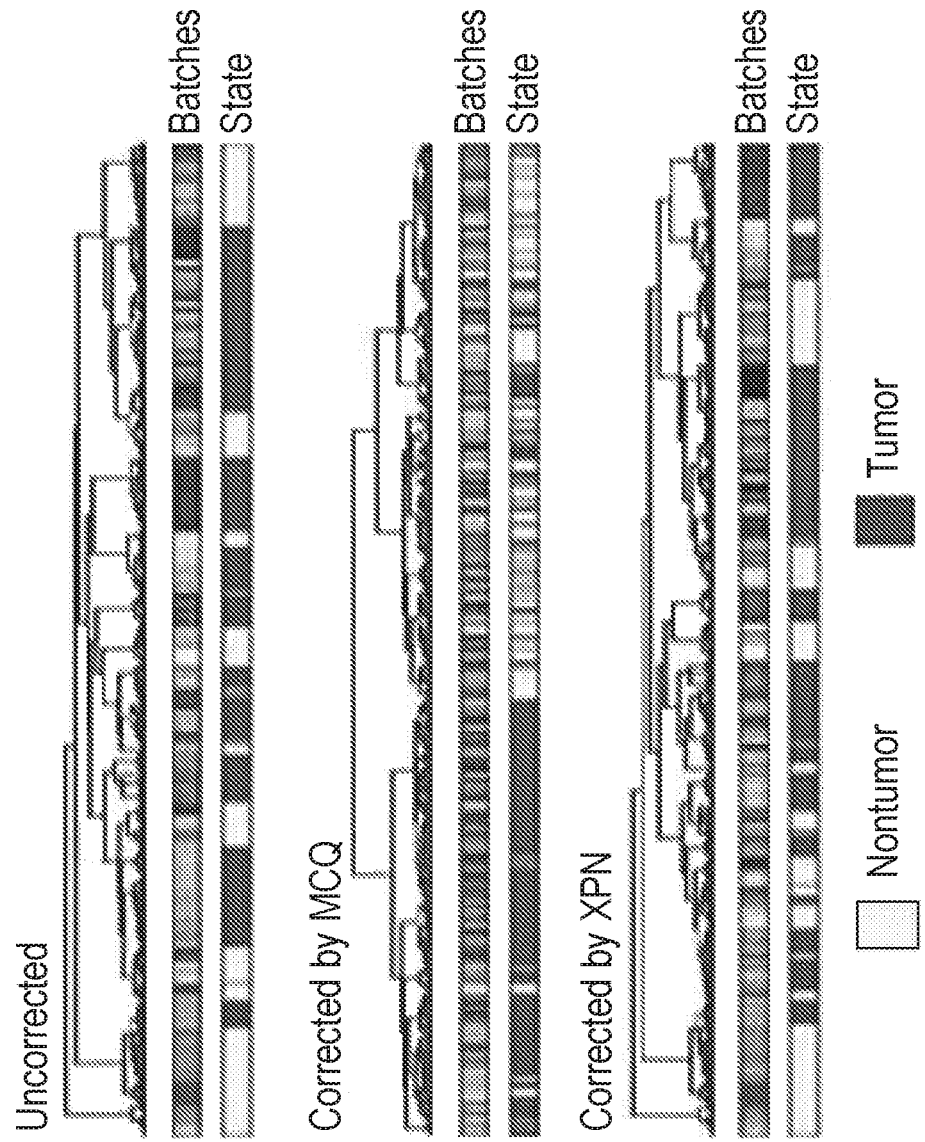

This collection contains datasets consisting of 2,790 expression profiles of benign prostate tissue, primary tumors, and metastatic or CRPC (CRPC/Met; FIG. 1B). We then removed a subset of samples with ambiguous clinical information and generated a single merged dataset by cross study normalization, based on median-centering and the quantile normalization method (MCQ; You S, Cho C S, Lee I, Hood L, Hwang D, Kim W U. A systems approach to rheumatoid arthritis. PLoS One 2012; 7:e51508. The merged dataset consists of 1,321 tumor specimens that we named the Discovery (DISC) cohort. The merged gene expression profiles showed a significant reduction of systematic, dataset-specific bias in comparison with the same dataset corrected by the XPN method, which is also used for merging data from different platforms (Shabalin A A, Tjelmeland H, Fan C, Perou C M, Nobel A B. Merging two gene-expression studies via cross-platform normalization. Bioinformatics 2008; 24:1154-60) (FIG. 1C). Biological differences between tumors and benign tissues were also maintained while minimizing batch effects (FIG. 1D).

As validation datasets, we assembled another collection of 12 independent cohorts consisting of 2,728 tumors from primary and CRPC/Met samples (Table 3). From this collection, 3 datasets, the Swedish watchful waiting cohort (SWD), the Emory cohort (EMORY), and the Health Study Prostate Tumor cohort (HSPT), were obtained from GEO. The gene expression profiles and clinical annotations of The Cancer Gnome Atlas (TCGA) cohort of 333 prostate cancer and SU2C/PCF Dream Team cohort (SU2C) of 118 CRPC/Mets were obtained from cBioPortal (http://www.cbioportal.org/). Seven additional cohorts were obtained from the Decipher GRID database (GRID). The expression datasets from the GRID were generated using a single platform, the Affymetrix Human Exon 1.0 ST Array, using primary tumors for the purpose of developing outcomes and treatment response signatures. We used these 7 cohorts to investigate associations of clinical outcomes with subtype assignment in this study.

TABLE 3

List of independent cohorts for validation of the subtypes.

| Cohort name | Number of samples | Disease status | Available clinical outcomes | Data from GRID | Abbreviation | PubMed ID |
|---|---|---|---|---|---|---|
| Swedish Watchful-Wainting Cohort | 281 | Localized | OS | No | SWD | 20233430 |
| The Cancer Genome Anatomy | 333 | Localized | N.A. | No | TCGA | 26000489 |
| Emory University | 106 | Localized | N.A. | No | EMORY | 24713434 |
| Health Professionals Follow-up Study and Physicians' Health Study Prostate Tumor Cohort | 264 | Localized | N.A. | No | HSPT | 25371445 |
| Stand Up To Cancer/Prostate Cancer Foundation Dream Team Cohort | 118 | CRPC/Met | N.A. | No | SU2C | 26000489 |
| Mayo Clinic Cohort 1 | 545 | Localized | PMS, TMP, PCSM | Yes | MAYO1 | 23826159 |
| Mayo Clinic Cohort 2 | 235 | Localized | PMS, TMP, PCSM | Yes | MAYO2 | 23770138 |
| Thomas Jefferson University cohort | 130 | Localized | PMS, TMP, PCSM | Yes | TJU | 25035207 |
| Cleveland Clinic Foundation Cohort | 182 | Localized | PMS, TMP, PCSM | Yes | CCF | 25466945 |
| Memorial Sloan Kettering Cancer Center cohort | 131 | Localized | PMS, PCSM | Yes | MSKCC | 20579941 |
| Erasmus Medical Centre Cohort | 48 | Localized | PMS, PCSM | Yes | EMC | 23319146 |
| Johns Hopkins Medicine Cohort | 355 | Localized | PMS, TMP, PCSM | Yes | JHM | 25466945 |

Abbreviations: N.A., not available; OS, overall survival; PMS, progression to metastatic state; PCSM, PC-specific mortality; TMP, time-to-metastatic progression.

Pathway Activations Describing Prostate Cancer Biology

Figure 1E:
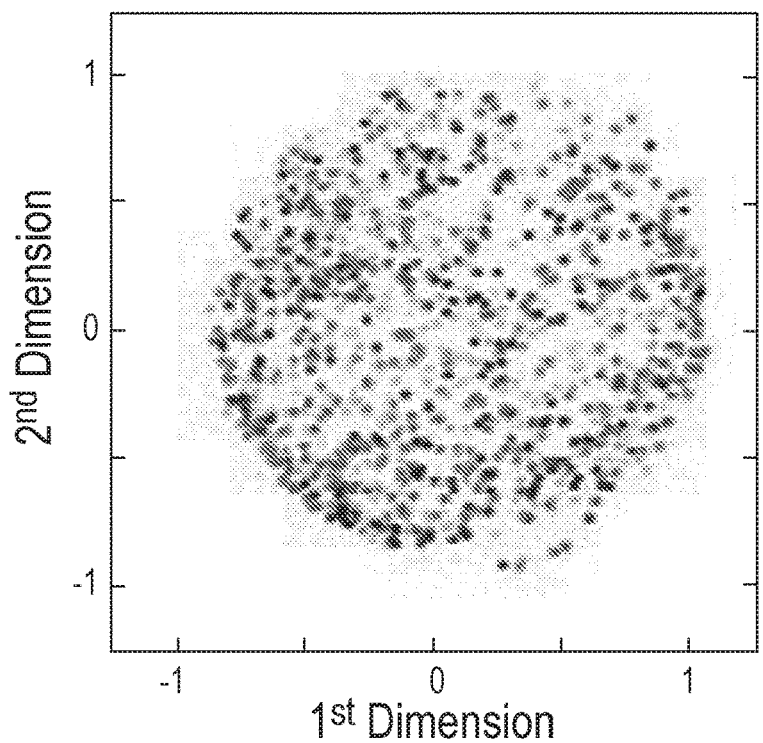
Figure 1E:
Figure 1E:
Figure 1E:
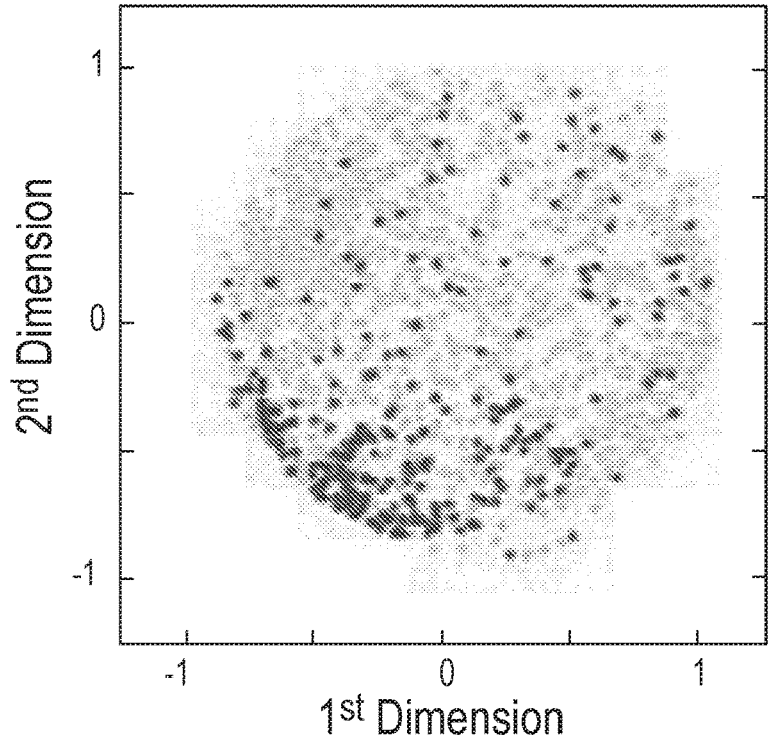

Recent studies have demonstrated the advantage of pathway-based analysis in clinical stratification for prostate and other cancer types (Markert E K, Mizuno H, Vazquez A, Levine A J. Molecular classification of prostate cancer using curated expression signatures. Proc Natl Acad Sci USA 2011; 108:21276-81; Gatza M L, Silva G O, Parker J S, Fan C, Perou C M. An integrated genomics approach identifies drivers of proliferation in luminal-subtype human breast cancer. Nat Genet 2014; 46:1051-9; Drier Y, Sheffer M, Domany E. Pathway-based personalized analysis of cancer. Proc Natl Acad Sci USA 2013; 110:6388-93), However, to date, there has been no study of prostate cancer using pathway activation profiles in which thousands of patient specimens were used. In addition, the utility of recently characterized molecular lesions such as AR amplification/overexpression, AR-V expression, transcriptional activation of EZH2 and forkhead box A1 (FOXA1), and SPOP mutation have not been fully exploited for classification. Therefore, we employed 22 pathway activation gene expression signatures encompassing prostate cancer-relevant signaling and genomic alterations (Tables 4 and 5) in the DISC cohort (n=1,321). These were ultimately collapsed into 14 pathway signatures that were grouped into 3 categories: (i) prostate cancer-relevant signaling pathways, including activation of AR, AR-V, EZH2, FOXA1, and rat sarcoma viral oncogene homolog (RAS) and inactivation by polycomb repression complex 2 (PRC); (ii) genetic and genomic alterations, including mutation of SPOP, TMPRSS2-ERG fusion (ERG), and deletion of PTEN; and (iii) biological features related to aggressive prostate cancer progression, including stemness (ES), cell proliferation (PRF), epithelial-mesenchy-mal transition (MES), proneural (PN), and aggressive prostate cancer with neuroendocrine differentiation (AV). Pathway activation scores were computed in each specimen in the DISC cohort using the Z-score method (Levine D M, Haynor D R, Castle J C, Stepaniants S B, Pellegrini M, Mao M, et al. Pathway and gene-set activation measurement from mRNA expression data: the tissue distribution of human pathways. Genome Biol 2006; 7:R93). The conversion of gene expression to pathway activation showed a further reduction of batch effects, while preserving biological differences that are particularly evident in the clustering of metastatic and non-metastatic samples (FIG. 1E).

TABLE 4

Publications from which the pathway activation gene sets were obtained

| Pathway Name | Description | # of genes | PubMed ID. |
|---|---|---|---|
| Androgen receptor (AR) | Three sets of up-regulated genes by AR in human patient tissues and prostate cancer cells | 1367<br>253<br>100 | 23260764<br>9289629<br>12185249 |
| AR-Variant (AR-V) | Two sets of up-regulated genes by presence or high expression of AR-variant in bone metastasis tissues or prostate cancer cells. | 114<br>24 | 21552559<br>22710436 |
| Deletion of phosphatase and tensin homolog (PTEN) | Genes up-regulated by loss of PTEN. | 113 | 17452630 |
| TMPRSS2-ERG fusion (ERG) | Gene expression signature up-regulated by TMPRSS-ERG fusion. | 140 | 18283340,<br>18505969,<br>17079440 |
| Forkhead box A1 (FOXA1) | Two gene sets up-regulated by FOXA1 with chromatin binding of FOXA1 in their regulatory regions of DNA. | 447<br>175 | 23539448<br>24292680 |
| Mutation of speckle-type POZ protein (SPOP) | Genes significantly up-regulated in all LNCaP-abl cell with three different SPOP mutations and down-regulated in cells with wildtype SPOP compared to cells with control vector treatment (FDR<0.05). | 35 | 25274033 |
| Enhancer of zeste 2 (EZH2) | EZH2-stimulated genes bound by EZH2 solo peaks | 84 | 23239736 |
| Inactivation by polycomb repression complex 2 (PRC) | Two sets of genes repressed by polycomb repression complex from human embryonic stem cell study and prostate cancer patients. | 654<br>87 | 16630818<br>18006806 |
| Rat sarcoma viral oncogene homolog (RAS) | Genes up-regulated by oncogenic RAS activation. | 179 | 16273092 |
| Stemness (ES) | Genes highly expressed in human embryonic stem cells according to 5 or more out of 20 profiling studies | 380 | 17204602 |
| Aggressive PC with neuroendocrine differentiation (AV) | Genes up-regulated in metastatic neuroendocrine (NE) prostate cancer compared to primary prostate cancer without NE phenotype. | 464 | 22389870 |
| Pro-neural (PN) | Genes reflecting neuronal differentiation (Pro-neural) activity. | 242 | 16530701 |
| Epithelial-mesenchymal transition (MES) | Genes represent activation of mesenchymal transition. | 141 | 16530701 |
| Poliferation (PRF) | Genes represent active proliferation. | 183 | 16530701 |

TABLE 5

| | The genes in the collection of pathway signatures used in this study | |
|---|---|---|
| Pathway | Reference | Genes (Entrez Gene ID) |
| AR | Sharma et al., Cancer Cell (2013) | 152940, 151258, 399948, 126432, 153129, 442117, 57600, 80820, 79143, 126075, 130355, 152485, 162073, 253012, 285636, 389072, 400451, 401152, 402117, 493869, 646603, 162333, 10162, 2122, 389336, 169166, 4803, 78815, 57185, 9182, 5122, 5128, 5218, 55331, 5339, 54704, 5828, 9743, 51246, 6434, 84900, 121601, 100124539, 780776, 728416, 677841, 677823, 677802, 654463, 646962, 643836, 619279, 613212, 504189, 494551, 445815, 445347, 404220, 404093, 403274, 403273, 401546, 401138, 390437, 390174, 389941, 389337, 388697, 387104, 376940, 375449, 375056, 374882, 373156, 344901, 344838, 344758, 343035, 341032, 340359, 340252, 339512, 339403, 337974, 337968, 286676, 286183, 286151, 286122, 286053, 285704, 285590, 285527, 285386, 284756, 284618, 284613, 284612, 284266, 284186, 284185, 284083, 284076, 284001, 283991, 283554, 283450, 283349, 280636, 261729, 259286, 257313, 257068, 257019, 256987, 256435, 256364, 256281, 255631, 254827, 254158, 254048, 252969, 245972, 222962, 222389, 222255, 222194, 222183, 222166, 221981, 221937, 221935, 221895, 221527, 221481, 221294, 221178, 221143, 221037, 221035, 220965, 219988, 219902, 219899, 219621, 206358, 203286, 203260, 203228, 203197, 203068, 202915, 202151, 201625, 201266, 200162, 200150, 199920, 197370, 197358, 192134, 191585, 170850, 170690, 170506, 168667, 166979, 164045, 163882, 163702, 163486, 162282, 159195, 157680, 155435, 155368, 154810, 154091, 153443, 153241, 153201, 152330, 152006, 150864, 150684, 148641, 147912, 147798, 147463, 146862, 146691, 145482, 145376, 145282, 145226, 143458, 143162, 140460, 138046, 137682, 136227, 135932, 134957, 133686, 132660, 131616, 131566, 131405, 130733, 130617, 130162, 129642, 129531, 129285, 128178, 127670, 127018, 127002, 126868, 126364, 124817, 124540, 124152, 123041, 121504, 120534, 119504, 118426, 117531, 116512, 116285, 116225, 116154, 116113, 115825, 114907, 114899, 114884, 114876, 114825, 114804, 114784, 113829, 113174, 112936, 112858, 112616, 96459, 94241, 94240, 94234, 93129, 92714, 92565, 92400, 92399, 92105, 91869, 91748, 91584, 91526, 91120, 90993, 90576, 90529, 90268, 90102, 89796, 89778, 87178, 85865, 85479, 85476, 85462, 85457, 85444, 85439, 85415, 85377, 85026, 84976, 84955, 84952, 84923, 84919, 84918, 84904, 84902, 84869, 84830, 84679, 84668, 84645, 84623, 84614, 84569, 84532, 84524, 84293, 84263, 84262, 84191, 84135, 84074, 84072, 84068, 84002, 83998, 83988, 83940, 83939, 83938, 83930, 83786, 83648, 83641, 83593, 83544, 83538, 83451, 83449, 81839, 81796, 81789, 81788, 81693, 81671, 81627, 81617, 81606, 81567, 81563, 81553, 81545, 81537, 81037, 81031, 80829, 80824, 80745, 80736, 80727, 80723, 80279, 80176, 80153, 80149, 80036, 80017, 79977, 79974, 79949, 79944, 79915, 79906, 79905, 79875, 79867, 79846, 79840, 79838, 79831, 79813, 79809, 79794, 79789, 79783, 79772, 79740, 79736, 79712, 79705, 79698, 79695, 79689, 79674, 79668, 79658, 79642, 79582, 79411, 79363, 79170, 79165, 79158, 79135, 79098, 79065, 79038, 79031, 65979, 65266, 65083, 65008, 64921, 64919, 64852, 64849, 64816, 64778, 64769, 64756, 64754, 64748, 64743, 64710, 64420, 64374, 64328, 64207, 64167, 64087, 64084, 64083, 64072, 64067, 64061, 63892, 60678, 60676, 60468, 59352, 59351, 59084, 58517, 58511, 58490, 58480, 57862, 57822, 57763, 57713, 57709, 57706, 57704, 57685, 57664, 57657, 57630, 57623, 57597, 57580, 57560, 57552, 57544, 57533, 57528, 57509, 57507, 57496, 57463, 57458, 57452, 57415, 57337, 57223, 57221, 57188, 57181, 57122, 57118, 57117, 57107, 57097, 57018, 56992, 56980, 56975, 56950, 56943, 56934, 56925, 56922, 56914, 56892, 56302, 56288, 56262, 56243, 56204, 56172, 56164, 55970, 55966, 55917, 55869, 55824, 55812, 55803, 55799, 55785, 55766, 55760, 55700, 55698, 55691, 55689, 55672, 55667, 55650, 55638, 55610, 55554, 55553, 55512, 55503, 55502, 55432, 55422, 55366, 55297, 55291, 55226, 55223, 55220, 55214, 55209, 55204, 55198, 55190, 55187, 55186, 55180, 55164, 55163, 55157, 55156, 55139, 55093, 55062, 55061, 55041, 55039, 55017, 54954, 54948, 54897, 54892, 54882, 54879, 54858, 54848, 54828, 54823, 54820, 54815, 54806, 54805, 54788, 54752, 54742, 54677, 54663, 54622, 54620, 54566, 54545, 54541, 54539, 54532, 54514, 54499, 54491, 54475, 54464, 54463, 54455, 54437, 54328, 54187, 53371, 53343, 51752, 51741, 51735, 51729, 51727, 51704, 51703, 51666, 51633, 51631, 51608, 51601, 51585, 51559, 51555, 51454, 51441, 51426, 51385, 51366, 51350, 51263, 51204, 51199, 51196, 51187, 51174, 51171, 51138, 51130, 51112, 51109, 51092, 51075, 51029, 51019, 50939, 50807, 50640, 50512, 50484, 43847, 29998, 29995, 29927, 29843, 29842, 29087, 29028, 28999, 28998, 28958, 28957, 28951, 27347, 27339, 27314, 27303, 27293, 27250, 27241, 27240, 27230, 27185, 27156, 27151, 27132, 27109, 27086, 27085, 27075, 27074, 27042, 26959, 26747, 26526, 26524, 26468, 26298, 26272, 26240, 26235, 26229, 26227, 26166, 26137, 26130, 26098, 26090, 26085, 26084, 26074, 26053, 26047, 26038, 26018, 26011, 26005, 25996, 25962, 25937, 25932, 25917, 25902, 25885, 25841, 25833, 25831, 25825, 25816, 23760, 23732, 23731, 23705, 23642, 23623, 23576, 23566, 23549, 23545, 23531, 23522, 23514, 23499, 23463, 23403, 23384, 23383, 23368, 23365, 23353, 23350, |

TABLE 5-continued

The genes in the collection of pathway signatures used in this study

| Pathway | Reference | Genes (Entrez Gene ID) |
|---|---|---|
| | | 23327, 23321, 23316, 23310, 23287, 23286, 23270, 23250, 23247, 23230, 23200, 23189, 23171, 23150, 23143, 23133, 23120, 23107, 23105, 23101, 23097, 23094, 23092, 23085, 23059, 23043, 23029, 23026, 23024, 23012, 23007, 23002, 22989, 22985, 22947, 22941, 22933, 22920, 22917, 22901, 22890, 22889, 22887, 22882, 22877, 22875, 22874, 22873, 22871, 22843, 22820, 15116, 11335, 11331, 11277, 11270, 11243, 11238, 11236, 11167, 11148, 11144, 11141, 11138, 11107, 11103, 11079, 11077, 11057, 11016, 11010, 11005, 10954, 10947, 10919, 10910, 10752, 10742, 10735, 10718, 10712, 10667, 10656, 10648, 10647, 10643, 10637, 10611, 10579, 10578, 10563, 10560, 10551, 10538, 10529, 10521, 10512, 10497, 10490, 10488, 10458, 10455, 10451, 10436, 10418, 10417, 10404, 10402, 10397, 10370, 10329, 10307, 10298, 10276, 10257, 10250, 10242, 10229, 10221, 10217, 10211, 10208, 10207, 10200, 10179, 10160, 10142, 10129, 10124, 10087, 10082, 10067, 10058, 10057, 10036, 10026, 10011, 10008, 9967, 9901, 9886, 9863, 9830, 9827, 9804, 9788, 9781, 9766, 9739, 9734, 9732, 9725, 9723, 9722, 9699, 9698, 9687, 9686, 9679, 9678, 9673, 9657, 9650, 9649, 9645, 9622, 9612, 9609, 9607, 9603, 9586, 9580, 9578, 9577, 9550, 9545, 9518, 9516, 9515, 9501, 9493, 9472, 9455, 9439, 9404, 9382, 9378, 9369, 9318, 9223, 9219, 9209, 9202, 9197, 9181, 9169, 9166, 9146, 9120, 9117, 9110, 9071, 9066, 8994, 8992, 8915, 8893, 8874, 8864, 8840, 8833, 8814, 8749, 8743, 8738, 8678, 8671, 8667, 8629, 8622, 8621, 8620, 8607, 8600, 8563, 8556, 8555, 8553, 8538, 8496, 8495, 8439, 8434, 8419, 8412, 8379, 8289, 8241, 8226, 8091, 8036, 8000, 7994, 7993, 7982, 7978, 7975, 7881, 7879, 7850, 7837, 7832, 7786, 7704, 7681, 7597, 7534, 7517, 7498, 7494, 7482, 7474, 7464, 7462, 7458, 7433, 7419, 7373, 7369, 7357, 7323, 7294, 7216, 7204, 7169, 7163, 7113, 7104, 7094, 7090, 7088, 7084, 7068, 7052, 7050, 7047, 7038, 7029, 7015, 7014, 7007, 7006, 6938, 6926, 6907, 6897, 6895, 6876, 6873, 6811, 6809, 6788, 6742, 6733, 6726, 6711, 6695, 6687, 6668, 6655, 6642, 6641, 6629, 6622, 6586, 6575, 6533, 6520, 6506, 6491, 6482, 6480, 6455, 6453, 6403, 6400, 6338, 6317, 6303, 6282, 6207, 6198, 6194, 6182, 6176, 6146, 6137, 6119, 6118, 6094, 6093, 6091, 6046, 6016, 6001, 5982, 5935, 5918, 5890, 5873, 5867, 5865, 5834, 5799, 5797, 5795, 5788, 5787, 5784, 5747, 5740, 5641, 5602, 5597, 5596, 5587, 5581, 5580, 5578, 5577, 5550, 5540, 5530, 5500, 5495, 5468, 5435, 5414, 5337, 5327, 5317, 5314, 5313, 5311, 5286, 5244, 5208, 5207, 5201, 5195, 5192, 5169, 5156, 5152, 5149, 5144, 5142, 5139, 5101, 5098, 5090, 5087, 5073, 5049, 5045, 5028, 5019, 5007, 5001, 4953, 4931, 4926, 4925, 4921, 4919, 4915, 4869, 4856, 4849, 4824, 4799, 4783, 4782, 4781, 4774, 4773, 4758, 4718, 4715, 4690, 4681, 4660, 4653, 4651, 4638, 4604, 4430, 4292, 4286, 4254, 4246, 4245, 4224, 4215, 4171, 4154, 4149, 4128, 4121, 4088, 4071, 4026, 4012, 3987, 3977, 3964, 3960, 3930, 3909, 3899, 3851, 3850, 3849, 3848, 3817, 3816, 3782, 3781, 3778, 3768, 3751, 3747, 3732, 3725, 3714, 3709, 3708, 3680, 3664, 3642, 3638, 3632, 3613, 3612, 3592, 3570, 3480, 3475, 3295, 3290, 3191, 3181, 3169, 3158, 3156, 3109, 3108, 3098, 2982, 2975, 2969, 2936, 2932, 2919, 2917, 2909, 2878, 2824, 2823, 2813, 2804, 2781, 2768, 2752, 2737, 2692, 2651, 2632, 2629, 2587, 2585, 2568, 2549, 2515, 2494, 2331, 2329, 2317, 2309, 2242, 2224, 2222, 2201, 2200, 2194, 2169, 2158, 2153, 2138, 2132, 2131, 2120, 2118, 2115, 2104, 2052, 2051, 2029, 2009, 1998, 1982, 1956, 1937, 1896, 1891, 1879, 1857, 1839, 1836, 1805, 1803, 1769, 1767, 1756, 1740, 1719, 1718, 1716, 1674, 1659, 1657, 1630, 1622, 1612, 1611, 1607, 1600, 1591, 1523, 1512, 1501, 1500, 1496, 1489, 1488, 1468, 1452, 1408, 1389, 1365, 1364, 1356, 1345, 1305, 1280, 1198, 1196, 1180, 1131, 1124, 1119, 1112, 1053, 1052, 1050, 1047, 999, 987, 983, 950, 944, 928, 904, 883, 859, 845, 835, 832, 831, 820, 776, 768, 759, 753, 747, 687, 678, 654, 640, 636, 605, 604, 587, 574, 549, 545, 517, 495, 463, 419, 395, 364, 360, 354, 330, 311, 288, 284, 247, 242, 220, 216, 182, 164, 157, 154, 132, 120, 107, 55, 47, 40 |
| AR | Mendiratta et al., JCO (2009) | 3817, 3817, 7113, 65986, 27347, 4824, 10257, 55839, 8611, 1047, 56937, 57556, 9687, 2289, 7704, 2181, 7855, 10198, 3781, 10892, 79098, 354, 55839, 133, 10198, 29028, 10512, 5001, 9240, 51347, 354, 5192, 2181, 990, 6675, 22936, 7366, 10788, 8867, 5004, 3156, 445347, 11057, 55892, 220, 8495, 55081, 25816, 5865, 7057, 11057, 10892, 5001, 51514, 114882, 25816, 10638, 7113, 10892, 9935, 27232, 60481, 23052, 2181, 9455, 8611, 51465, 445347, 26046, 10198, 3156, 10645, 400451, 64780, 23099, 990, 56995, 23099, 8560, 5983, 3557, 5583, 79098, 51312, 10560, 2235, 23099, 5395, 22837, 2887, 55840, 1718, 1052, 10725, 5152, 9044, 57178, 5867, 3949, 54491, 55627, 4174, 114882, 7163, 6385, 54861, 10628, 23299, 25803, 481, 3177, 3613, 8756, 27244, 400451, 654342, 10954, 2237, 10059, 5366, 11167, 6936, 25840, 6659, 5062, 100506658, 6303, 1487, 9, 3638, 7088, 3915, 6482, 694, 54733, 90355, 10725, 6659, 4086, 8660, 5558, 55852, 55656, 23310, 993, 6652, 56829, 7976, 694, 2222, 8165, 6303, 3422, 100132565, 8165, 23327, 11057, 3108, 23086, 9686, 2235, 51002, 23001, 3422, 80232, 5867, 55623, 4173, 10096, 9619, 4172, 23216, 1487, 6652, 9518, 4792, 1487, 10397, 2542, 3817, 384, 79073, 23077, 23598, 50628, 10645, 4790, 55168, 5500, 6239, 10765, 23047, 6764, 5520, 8353, 8555, 4363, 4678, 8507, 10765, 23286, 31, 1119, 3417, 55718, |

TABLE 5-continued

The genes in the collection of pathway signatures used in this study

| Pathway | Reference | Genes (Entrez Gene ID) |
|---|---|---|
| | | 23112, 6309, 9686, 79170, 8349, 80003, 56985, 7795, 55604, 1831, 3915, 64087, 2800, 3229, 5797, 5293, 23327, 3983, 50814, 8473, 9261, 6867, 51317, 60481, 6774, 4047, 5373, 2222, 5813, 55041, 8050, 22998, 5962, 7703, 10903, 10096, 84187, 4121, 55144, 5074, 8879, 5813, 10276, 2734, 64710, 9894, 643854, 5927, 10715, 4077, 9019, 81671, 9813, 8237, 2063, 2582, 30850, 55252, 5687, 54676, 4953, 7763, 9750, 5908, 23355, 10475, 83440, 6310, 79726, 6809, 25800, 6655, 22845, 22905, 55347, 93487, 357, 3720, 8795, 9175, 26152, 23598, 1534, 3183, 11171, 9775, 8648, 3654, 7150, 10521, 2805, 80111, 8289 |
| AR | Nelson et al., PNAS (2002) | 3248, 8611, 6319, 6652, 1718, 6611, 51171, 220, 6303, 3157, 1622, 2683, 5264, 3422, 60481, 7358, 2181, 1644, 10788, 5238, 9455, 9590, 7163, 10611, 10645, 11099, 2982, 8821, 10461, 11217, 590, 5587, 6385, 5178, 56995, 8503, 57007, 6414, 2936, 6446, 27347, 4189, 3817, 354, 9622, 1362, 5274, 11047, 87, 3685, 3880, 3005, 11258, 10627, 4325, 2335, 56937, 567, 81563, 8916, 79689, 9510, 11057, 8241, 6675, 7982, 1801, 4094, 10397, 22936, 25816, 8555, 3398, 3398, 55502, 1487, 1024, 2289, 10497, 10257, 56172, 54407, 6616, 10513, 563, 3998, 5867, 6728, 1836, 9871, 9218, 6337, 2030, 4824, 25803, 65986, 8554, 8848, 84159, 9314, 4609 |
| AR-V | Hornberg et al., PLoS One (2011) | 72, 120, 140, 213, 216, 367, 699, 890, 983, 991, 1058, 1063, 1123, 1164, 1525, 1870, 1875, 1917, 2150, 2171, 2261, 2935, 2938, 3123, 3127, 3181, 3248, 3308, 3315, 3485, 3775, 3895, 4126, 4172, 4176, 4192, 4824, 5111, 5166, 5264, 5307, 5360, 5597, 5603, 5792, 5985, 6234, 6281, 6337, 6950, 7020, 7272, 7280, 7298, 7364, 7366, 7367, 7525, 7913, 8140, 8318, 8407, 8644, 8801, 8836, 9055, 9061, 9133, 9168, 9212, 9401, 10024, 10112, 10370, 10457, 10551, 10635, 11004, 11065, 11339, 22974, 23671, 25827, 25923, 25932, 26063, 26271, 29128, 51050, 51203, 51337, 51703, 55502, 55872, 57415, 57556, 57819, 64151, 79019, 81539, 81610, 81620, 81831, 83461, 83596, 83690, 83879, 84034, 84678, 84706, 93100, 116844, 127845, 139886, 140462, 140710, 145837, 146456, 151126, 154043, 201562, 203068, 221935, 253558, 259266, 388468, 388621, 391267, 399942, 400710, 401466, 402644, 440482, 440915, 642460, 645138, 645656, 646163, 647000, 647169, 653377, 653658, 100129028, 100131161 |
| AR-V | Hu et al., Cancer Res (2012) | 113130, 332, 699, 3838, 9735, 701, 994, 10459, 1062, 9700, 11004, 4751, 11113, 3835, 890, 11130, 22974, 995, 56992, 4085, 9088, 11065, 5347, 51203 |
| PTEN | Saal et al., PNAS (2007) | 330, 699, 891, 1010, 1062, 1164, 1207, 2618, 2999, 3066, 3608, 3833, 3838, 3925, 4172, 4175, 4259, 4291, 4751, 5052, 5290, 5359, 5612, 5718, 5870, 5873, 5889, 5984, 6612, 6619, 6632, 6732, 6772, 6941, 7159, 7307, 7372, 7444, 8208, 8317, 8532, 8833, 9133, 9232, 9392, 9493, 9711, 9833, 9928, 10440, 10541, 10589, 10606, 10951, 10963, 11004, 11073, 11169, 11222, 23279, 24137, 25852, 26973, 27238, 27316, 29028, 29127, 29979, 51642, 54503, 54534, 54625, 54845, 55248, 79694, 79894, 84056, 87178, 151188, 151246, 151636, 157313, 205564, 219988, 64844, 54906, 92342, 126731, 81610, 387103, 219285, 84955, 1503, 64789, 9787, 29105, 51773, 3192, 55827, 3796, 79132, 57380, 7936, 6426, 6434, 6596, 60313, 6790, 7280, 54014 |
| ERG | Tomlins et al., Neoplasia (2008); Setlur et al., JNCI (2008); Iljin et al., Cancer Res (2006) | 183, 272, 347, 397, 658, 776, 950, 999, 1280, 1298, 1485, 1627, 1644, 1824, 1889, 1983, 2078, 2152, 2153, 2528, 2690, 2705, 2812, 2867, 2982, 3065, 3109, 3249, 3549, 3710, 3781, 3783, 3790, 3800, 3918, 4035, 4217, 4646, 4725, 4883, 4905, 5074, 5140, 5152, 5192, 5226, 5575, 5585, 5597, 5607, 5719, 5754, 5796, 5832, 5989, 6001, 6294, 6602, 6629, 6675, 6833, 6899, 6908, 7027, 7088, 7174, 7291, 7326, 7358, 7520, 7551, 7941, 8030, 8505, 8507, 8618, 8648, 8672, 8766, 9053, 9073, 9112, 9411, 9529, 9766, 9892, 10202, 10269, 10321, 10477, 10551, 10557, 10656, 10801, 11052, 11079, 22877, 22881, 23250, 26037, 26751, 27199, 27314, 27347, 30848, 51365, 54880, 54997, 55384, 55623, 55753, 55884, 56099, 57630, 65108, 79570, 81557, 83988, 147741, 221395, 246100, 266977, 339260, 349160, 389432, 400710, 728239, 100133941, 100506658, 221061, 55614, 90625, 948, 8853, 3831, 5218, 23613, 5891, 4072, 23598 |
| FOXA1 | Jin et al., Cancer Res (2013) | 1644, 384, 6013, 2353, 3248, 7365, 6820, 150519, 1058, 8501, 84722, 2354, 222, 283651, 24137, 55771, 55388, 8034, 2030, 9609, 6038, 283651, 677765, 26793, 81035, 2731, 374393, 162681, 645121, 283349, 5406, 81624, 8825, 18, 1031, 642569, 100132106, 57198, 83463, 606551, 23252, 83849, 403, 10384, 730268, 83903, 647718, 653387, 2870, 647250, 441957, 2177, 5558, 648200, 132864, 1846, 282969, 149830, 6019, 643265, 127700, 84904, 729003, 83540, 157313, 57124, 650061, 84750, 387921, 729667, 2981, 7439, 59341, 7035, 11052, 100134006, 387761, 729384, 5651, 11086, 100131871, 653665, 4594, 5783, 4603, 100128295, 55425, 26747, 9687, 641, 409, 124976, 50614, 30820, 5228, 51435, 4135, 730809, 642153, 148103, 100134550, 4477, 653111, 84296, 649984, 646236, 503542, 91431, 654222, 7940, 647748, 729383, 145837, 25, 649067, 100302254, 54784, 590, 29893, 83992, 286207, 4595, 728340, 390507, 729012, 57245, 79187, 10160, 1734, 387775, 653468, 650995, 642130, 27077, 728217, 2030, 143503, 8350, 51102, 652102, 391427, |

TABLE 5-continued

The genes in the collection of pathway signatures used in this study

| Pathway | Reference | Genes (Entrez Gene ID) |
|---|---|---|
| | | 100134248, 574508, 100131392, 643035, 90381, 650003, 55711, 100128781, 85414, 51313, 388946, 388242, 338692, 23074, 51776, 407046, 649676, 440311, 26809, 84224, 79643, 375449, 645164, 27324, 80742, 8796, 643233, 118738, 100132029, 100131768, 84532, 22836, 389690, 51430, 647336, 6038, 729392, 3158, 440072, 651952, 727722, 388394, 641958, 10868, 135114, 650852, 84140, 386724, 399939, 2587, 65061, 728114, 1553, 3955, 652185, 100128862, 375347, 643326, 100128374, 158326, 643150, 728352, 57144, 5950, 100128653, 340990, 339476, 100132317, 63976, 100128191, 144678, 647534, 11221, 727833, 221150, 440040, 7170, 653620, 51340, 54143, 1587, 100129986, 652610, 284083, 100128765, 572, 483, 255812, 650036, 84767, 100131243, 1804, 642167, 84068, 643085, 728531, 100134365, 728686, 724027, 622, 127002, 4543, 130540, 348021, 10814, 730394, 5178, 644305, 445347, 2267, 55867, 9768, 340970, 339977, 392232, 728780, 168455, 84553, 404785, 100302116, 5239, 652251, 203430, 100133213, 652490, 652046, 642411, 644041, 10659, 646791, 100131454, 56953, 643943, 55120, 57402, 5947, 5741, 641714, 729198, 161635, 645113, 2260, 100126693, 100132649, 2155, 644990, 390705, 22999, 79370, 653527, 388507, 124, 341230, 128506, 92106, 50515, 651381, 644943, 645485, 55329, 201299, 100133599, 54490, 54821, 79097, 23510, 100134651, 643623, 643246, 91614, 645425, 729240, 285755, 10168, 340024, 158471, 64087, 100129200, 140432, 100134539, 643722, 649184, 406911, 55166, 9700, 643906, 256309, 100127952, 645726, 590, 646976, 650749, 650274, 80312, 995, 222, 3164, 388666, 80741, 146481, 100134050, 653333, 23273, 80204, 133609, 85462, 9793, 284260, 26018, 23178, 7480, 158471, 10720, 126, 648979, 653689, 142827, 121214, 730024, 217, 55199, 644785, 639, 100302203, 254428, 5004, 100128908, 100133311, 645875, 4951, 100129463, 41, 57464, 649214, 7035, 57824, 729051, 219, 730861, 56959, 89944, 57222, 440153, 100073347, 2650, 7033, 8821, 286527, 5831, 55504, 642362, 1404, 9882, 4751, 154091, 11200, 94104, 55247, 6080, 1010, 389206, 5557, 100133898, 5557, 26018, 84058, 57221, 112611, 51073, 4173, 100132464, 64946, 23306, 55504, 594837, 25953, 645691, 89876, 100132964, 259217, 53834, 441484, 2146, 594838, 91057, 53834, 5427, 65062, 55038, 55658, 23286, 151246, 3169, 5631, 4494, 10714, 26272 |
| FOXA1 | Robinson et al., Oncogene (2013) | 3336, 1981, 644634, 140901, 9415, 115948, 64061, 728643, 4627, 85456, 57805, 2975, 79977, 23420, 103, 220686, 10523, 3609, 388692, 29128, 445347, 9020, 5934, 9993, 25832, 338707, 22974, 221035, 23318, 11051, 11198, 5585, 124565, 8301, 63901, 8916, 10298, 949, 1399, 440270, 390916, 701, 56882, 55683, 116064, 55502, 26039, 644745, 2064, 3714, 10648, 6720, 22998, 10628, 3187, 10193, 728857, 22911, 286075, 7259, 7155, 7913, 10963, 84895, 23310, 2624, 9589, 9191, 3304, 65123, 7317, 6837, 7536, 353131, 6744, 652713, 23244, 56882, 54443, 132671, 3609, 399664, 2870, 4172, 441205, 7475, 653199, 126133, 6522, 9267, 4128, 339287, 1981, 440915, 11167, 4820, 1717, 3091, 392288, 9918, 3158, 27328, 25929, 25957, 326, 1982, 1108, 1949, 50628, 23052, 2289, 329, 7082, 3232, 1639, 652160, 221981, 389322, 729154, 83606, 2101, 5422, 200030, 51701, 55706, 9922, 51402, 26054, 11338, 5213, 9688, 23517, 645879, 8473, 23270, 64207, 647500, 3985, 56829, 56853, 653321, 4302, 649702, 64061, 647983, 54545, 201255, 4605, 55905, 729234, 8539, 23451, 6574, 6238, 100129543, 9013, 7544, 22985, 653419, 23306, 54093, 644322, 647000, 8897, 27333, 5192, 649908, 10985, 4627, 5925, 646665, 5584, 9854, 64848, 10594 |
| SPOP | Geng et al., Cancer Res (2014) | 730996, 6446, 3936, 58480, 354, 79054, 6446, 10397, 6446, 646723, 25803, 57801, 54490, 6590, 4070, 5225, 1811, 79054, 54206, 2235, 4316, 585, 55897, 148327, 649970, 4316, 4285, 85012, 8611, 10257, 246, 8611, 23623, 390557, 3710 |
| EZH2 | Xu et al., Science (2013) | 5036, 9401, 5315, 51069, 55052, 5886, 29082, 91057, 5707, 199699, 64426, 2289, 7398, 5810, 7417, 10155, 8550, 29028, 9768, 11004, 790, 4801, 55299, 122769, 6426, 132, 3029, 10592, 81620, 56834, 57696, 64222, 256126, 26517, 90480, 84262, 128239, 1111, 65003, 64105, 10921, 26528, 51081, 1164, 4796, 6883, 6883, 57819, 79902, 4176, 5514, 4173, 55631, 23204, 5889, 56683, 790955, 7329, 5434, 79171, 51154, 10535, 55146, 1869, 10640, 6520, 4860, 1981, 2091, 1537, 5757, 5718, 23548, 5216, 79959, 1841, 55706, 80179, 4893, 79447, 10426, 1810, 54069, 10614 |
| PRC | Lee et al., Cell (2006) | 6833, 25841, 170689, 170692, 105, 196883, 114, 116, 148, 150, 153, 155, 246, 257, 60529, 138649, 84210, 389002, 84079, 362, 57569, 132946, 429, 430, 460, 23245, 463, 467, 474, 84913, 579, 56751, 343472, 56033, 8538, 596, 79365, 128408, 27319, 353500, 646, 7832, 283078, 25789, 375061, 387597, 148753, 149499, 24141, 59271, 25927, 89876, 56934, 774, 776, 777, 8913, 796, 55450, 54897, 869, 140689, 874, 57332, 947, 925, 64072, 1005, 8941, 1031, 1045, 55803, 94027, 94115, 51673, 9023, 140578, 8646, 25884, 64377, 338917, 1149, 4435, 146225, 1184, 161198, 64084, 26507, 1271, 255631, 84570, 85301, 1280, 1287, 1288, 1298, 81035, 1311, 84940, 1394, 9244, 55118, 1412, 64478, 114788, 1501, 57369, 9547, 58191, 1591, 1592, 56603, 340665, 1594, 1602, 117154, 166614, 1630, 54798, 23576, |

TABLE 5-continued

The genes in the collection of pathway signatures used in this study

| Pathway | Reference | Genes (Entrez Gene ID) |
|---|---|---|
| | | 1608, 9162, 50846, 1735, 25849, 22943, 27123, 54567, 1745, 1746, 1747, 1748, 1761, 10655, 58524, 220164, 8110, 283417, 1816, 1825, 57453, 53905, 50506, 1846, 9427, 1942, 1944, 25975, 1960, 1961, 55531, 2019, 2020, 8320, 2034, 64097, 2044, 2047, 2049, 2066, 90952, 83715, 80712, 2149, 151647, 163933, 57795, 339479, 284716, 151354, 2201, 2203, 55336, 26273, 54738, 9638, 26281, 2248, 2250, 2254, 344018, 2313, 54508, 79962, 54790, 150538, 151278, 283212, 91607, 400765, 253650, 349152, 129804, 203111, 400591, 388336, 399717, 389064, 23768, 3170, 27023, 2306, 27022, 349334, 200350, 286380, 387054, 2304, 2294, 2290, 2302, 2300, 668, 257019, 2526, 11211, 2535, 2555, 2557, 2572, 2583, 124872, 374378, 8811, 2624, 2625, 2626, 2627, 2637, 392255, 151449, 2668, 2690, 2693, 55340, 2706, 23127, 9630, 2262, 2824, 2834, 83550, 2835, 338557, 54112, 2891, 2894, 2897, 2899, 116443, 2917, 145258, 2928, 219409, 170825, 2982, 3000, 9464, 3039, 3040, 54626, 84667, 23462, 55733, 3087, 64399, 3142, 3110, 3167, 340784, 3211, 10481, 3212, 3213, 3216, 3217, 3218, 3227, 3228, 3221, 3222, 3223, 3224, 3231, 3238, 3239, 3232, 3233, 3234, 3235, 51440, 60495, 8739, 9953, 388605, 266722, 3299, 3310, 3350, 3358, 3363, 7087, 51214, 84966, 26280, 3574, 9118, 84684, 3645, 3651, 79191, 50805, 10265, 3670, 64843, 3676, 3706, 3725, 81621, 3736, 3738, 7881, 3747, 3749, 3752, 3756, 23416, 56660, 56659, 3776, 50801, 3778, 3786, 27012, 22846, 57214, 57535, 85376, 84623, 9365, 9314, 339855, 10660, 3958, 8549, 9355, 89884, 64211, 26468, 431707, 4010, 124842, 127003, 143903, 148898, 150221, 153684, 200030, 340529, 388394, 388407, 389289, 400120, 405753, 440804, 441413, 441425, 441426, 441430, 441459, 56901, 92162, 23284, 4023, 57631, 145581, 4036, 347730, 4053, 4058, 256586, 4081, 10586, 9935, 4118, 5596, 4137, 55283, 55897, 284207, 84803, 145773, 440482, 340419, 403312, 4300, 9242, 4487, 4489, 4490, 4496, 4499, 326343, 4618, 4645, 4654, 162417, 89797, 4684, 4741, 4747, 4745, 4760, 4761, 4762, 63973, 50674, 4784, 90527, 4821, 159296, 26257, 4824, 4825, 84504, 145741, 8715, 4861, 255743, 4883, 4884, 4886, 7026, 8013, 3084, 9542, 220323, 84618, 9423, 84628, 4914, 4915, 266743, 4948, 25903, 10215, 3175, 9480, 4985, 84709, 130497, 133060, 92736, 347741, 23440, 5013, 5015, 64064, 5069, 5075, 5076, 5077, 5080, 5081, 7849, 5083, 27253, 5100, 9659, 5156, 9758, 23037, 5179, 5239, 5241, 401, 8929, 8395, 8544, 5307, 5308, 5309, 63876, 5317, 5339, 5362, 5376, 127435, 5426, 5453, 5456, 5457, 5458, 5459, 22843, 84366, 59335, 54886, 5581, 5592, 60675, 256297, 5729, 5732, 5733, 5734, 5737, 5744, 11122, 10076, 5827, 5697, 84084, 399694, 5923, 83593, 30062, 5950, 9185, 28984, 6001, 8601, 388531, 11035, 79836, 79589, 64221, 27330, 10633, 284654, 349667, 6263, 79966, 6330, 6340, 6344, 80031, 6422, 6425, 130367, 6469, 6473, 6474, 54847, 6493, 6495, 10736, 6496, 4990, 201780, 6506, 6509, 123041, 5172, 11001, 7780, 7781, 7782, 140679, 148641, 6529, 6531, 9152, 6549, 6550, 6578, 81796, 6585, 9353, 114798, 22865, 80235, 55509, 114815, 22986, 8403, 64321, 83595, 9576, 50859, 10418, 6716, 6751, 6752, 8128, 55351, 11075, 29091, 55061, 9899, 91683, 6886, 10716, 6899, 6909, 30009, 6926, 6910, 6920, 6928, 339488, 7056, 113091, 7080, 7092, 3195, 3196, 23671, 57393, 161291, 29767, 970, 7161, 8717, 7200, 55521, 440730, 114088, 7224, 85480, 57348, 7349, 7350, 8633, 389658, 124590, 11023, 25806, 7421, 30813, 49856, 51352, 7471, 80326, 7480, 7481, 51384, 7472, 89780, 7475, 7476, 7490, 284273, 7704, 340595, 9839, 57732, 7545, 84107, 84225, 55079, 80818, 84858, 22806 |
| PRC | Yu et al., Cancer Res (2007) | 26, 70, 627, 744, 783, 958, 1075, 1116, 1511, 1571, 1803, 1909, 2051, 2258, 2532, 2774, 3071, 3077, 3371, 3683, 3689, 3696, 3872, 4223, 4625, 4629, 4635, 4646, 5179, 5376, 5592, 5733, 6013, 6387, 6505, 6622, 6863, 6928, 7040, 7227, 7472, 8013, 8406, 8835, 8854, 9172, 9180, 9506, 9508, 10468, 11080, 11279, 23314, 24141, 25802, 25924, 25937, 26167, 27123, 27151, 28984, 30061, 51309, 51384, 51700, 53405, 54738, 55504, 55816, 57094, 57172, 57418, 57569, 57821, 60495, 64399, 66004, 79258, 79365, 81035, 81553, 91607, 114788, 133584, 168667, 221833, 283078 |
| RAS | Bild et al., Nature (2006) | 101, 154, 384, 490, 650, 688, 805, 813, 829, 1316, 1453, 1454, 1594, 1604, 1743, 1839, 1843, 1846, 1847, 1848, 1947, 1958, 1969, 1992, 2004, 2069, 2317, 2353, 2683, 2707, 2709, 2710, 2810, 2919, 2920, 2921, 3099, 3265, 3552, 3553, 3576, 3589, 3598, 3628, 3673, 3710, 3726, 3775, 3783, 3949, 3976, 4084, 4170, 4237, 4323, 4615, 4907, 4953, 5055, 5266, 5268, 5292, 5293, 5329, 5362, 5473, 5621, 5743, 5744, 5791, 5806, 5817, 6277, 6303, 6364, 6374, 6382, 6385, 6515, 6525, 6548, 6574, 6675, 6804, 6926, 7039, 7076, 7150, 7262, 7277, 7378, 7422, 7538, 7804, 7851, 7980, 8651, 8795, 8797, 8848, 8870, 8900, 9123, 9136, 9170, 9221, 9227, 9518, 9590, 9592, 9938, 9943, 9982, 10105, 10135, 10140, 10184, 10221, 10397, 10509, 10687, 10855, 10938, 11007, 11332, 22822, 23135, 23227, 23529, 23645, 23767, 26092, 29005, 29126, 50486, 50515, 50640, 51129, 51228, 51312, 51330, 54676, 54910, 55117, 55149, 55384, 55612, 55700, 56938, 64332, 64750, 64866, 65059, 79413, 79686, 79993, 80328, 80853, 81631, 81848, |

TABLE 5-continued

The genes in the collection of pathway signatures used in this study

| Pathway | Reference | Genes (Entrez Gene ID) |
|---|---|---|
| | | 83667, 84002, 84803, 84951, 84985, 85450, 89795, 94234, 117195, 119548, 120224, 129642, 135398, 144195, 152519, 163259, 201176, 201799, 285672 |
| ES | Assou et al., Stem Cells (2007) | 58, 70, 89, 119, 142, 249, 262, 332, 477, 657, 699, 701, 708, 836, 875, 890, 891, 934, 983, 990, 991, 993, 1075, 1111, 1381, 1382, 1400, 1434, 1525, 1592, 1690, 1719, 1730, 1741, 1763, 1788, 1789, 1829, 1894, 2030, 2041, 2058, 2064, 2115, 2118, 2171, 2237, 2239, 2247, 2258, 2260, 2289, 2308, 2558, 2562, 2571, 2618, 2697, 2731, 2824, 2842, 2956, 3038, 3070, 3149, 3159, 3161, 3182, 3308, 3312, 3329, 3609, 3620, 3710, 3720, 3730, 3790, 3800, 3818, 3838, 3856, 3932, 3964, 4072, 4074, 4124, 4141, 4144, 4171, 4172, 4173, 4174, 4175, 4176, 4240, 4257, 4277, 4361, 4436, 4521, 4522, 4678, 4801, 4838, 4869, 4913, 4922, 4947, 4998, 5058, 5097, 5134, 5163, 5198, 5291, 5331, 5366, 5393, 5411, 5420, 5427, 5460, 5495, 5519, 5521, 5557, 5558, 5613, 5631, 5771, 5803, 5865, 5919, 5932, 5983, 5984, 6059, 6091, 6229, 6241, 6297, 6299, 6337, 6422, 6423, 6426, 6432, 6480, 6535, 6566, 6611, 6626, 6638, 6653, 6657, 6741, 6997, 7004, 7013, 7019, 7072, 7112, 7138, 7360, 7374, 7447, 7546, 7547, 7748, 7804, 7855, 7913, 8087, 8239, 8324, 8433, 8519, 8577, 8607, 8611, 8615, 8745, 8805, 8820, 8842, 8880, 8886, 9053, 9074, 9143, 9184, 9188, 9201, 9212, 9221, 9232, 9282, 9350, 9456, 9473, 9573, 9603, 9787, 9908, 9910, 10011, 10036, 10049, 10053, 10146, 10149, 10153, 10157, 10196, 10308, 10346, 10360, 10383, 10434, 10439, 10459, 10528, 10606, 10606, 10622, 10635, 10637, 10643, 10644, 10797, 10874, 11004, 11040, 11051, 11061, 11083, 11143, 11145, 11168, 11169, 11200, 11245, 11339, 22800, 22823, 22929, 23108, 23170, 23178, 23195, 23242, 23246, 23397, 23401, 23411, 23468, 23534, 23683, 24137, 25788, 25926, 25957, 26018, 26047, 26053, 26135, 26207, 26354, 27022, 27231, 29078, 29785, 29920, 51018, 51053, 51083, 51104, 51268, 51385, 51444, 51491, 51574, 51575, 51582, 51599, 51659, 51704, 51816, 54014, 54069, 54478, 54517, 54566, 54596, 54821, 54845, 54892, 54989, 55003, 55010, 55120, 55211, 55237, 55270, 55299, 55320, 55366, 55388, 55660, 55706, 55726, 55749, 55759, 55920, 55975, 56548, 56915, 57122, 57167, 57181, 57380, 57405, 57486, 57502, 57504, 57541, 57556, 57633, 57685, 58516, 63978, 64318, 64782, 64849, 65981, 79007, 79012, 79023, 79071, 79075, 79158, 79647, 79664, 79727, 79923, 79960, 80155, 80179, 80324, 80775, 81539, 81542, 81554, 81620, 81848, 83439, 83596, 84101, 84296, 84343, 84549, 84889, 84891, 90806, 90990, 91431, 92667, 93099, 112399, 113130, 114569, 115572, 117156, 120071, 157627, 157695, 220042, 221079, 347733, 548596 |
| AV | Beltran et al., Cancer Discov (2011) | 268, 292, 317, 610, 613, 656, 699, 701, 745, 782, 835, 890, 899, 990, 991, 997, 1058, 1062, 1063, 1072, 1072, 1122, 1132, 1141, 1351, 1387, 1412, 1455, 1503, 1663, 1759, 1846, 1850, 1869, 1870, 1871, 1917, 1952, 1978, 2026, 2161, 2176, 2237, 2245, 2256, 2297, 2305, 2491, 2529, 2563, 2583, 2584, 2644, 2781, 2786, 2821, 2918, 3026, 3161, 3195, 3225, 3227, 3609, 3619, 3710, 3714, 3714, 3757, 3777, 3796, 3832, 3992, 4001, 4023, 4131, 4171, 4174, 4175, 4176, 4241, 4288, 4521, 4605, 4642, 4661, 4670, 4751, 4803, 4821, 4841, 4879, 4881, 4917, 4985, 4998, 5050, 5260, 5347, 5355, 5424, 5442, 5478, 5557, 5603, 5623, 5630, 5662, 5753, 5985, 6175, 6241, 6294, 6297, 6455, 6502, 6590, 6597, 6620, 6749, 6790, 6804, 6812, 6833, 6839, 6853, 6855, 6860, 6861, 7023, 7036, 7083, 7153, 7175, 7329, 7425, 7516, 7546, 7703, 8021, 8120, 8175, 8193, 8208, 8290, 8317, 8318, 8359, 8475, 8497, 8614, 8655, 8914, 8927, 8941, 9080, 9088, 9127, 9128, 9133, 9148, 9156, 9203, 9212, 9232, 9319, 9355, 9479, 9480, 9493, 9515, 9524, 9578, 9582, 9700, 9735, 9787, 9824, 9837, 9918, 9928, 10036, 10083, 10112, 10287, 10459, 10460, 10501, 10535, 10635, 10733, 10736, 10744, 10814, 10900, 10908, 10921, 10992, 10994, 11000, 11082, 11113, 11130, 11169, 11178, 11182, 11339, 22859, 22974, 22983, 22994, 23025, 23046, 23138, 23299, 23307, 23370, 23373, 23396, 23594, 23649, 24137, 24148, 25789, 25862, 26000, 26000, 26251, 26255, 26528, 27156, 27245, 27324, 27338, 28231, 29089, 29128, 29843, 29954, 51203, 51291, 51412, 51512, 51514, 51621, 51673, 51690, 53354, 53615, 53637, 53820, 53820, 54332, 54438, 54443, 54503, 54520, 54734, 54825, 55038, 55071, 55122, 55135, 55143, 55165, 55224, 55229, 55247, 55295, 55355, 55388, 55530, 55635, 55658, 55722, 55723, 55753, 55771, 55789, 55964, 56033, 56675, 56896, 56901, 56905, 56938, 56995, 57082, 57125, 57156, 57405, 57418, 57464, 57468, 57473, 57540, 57574, 57657, 57719, 58492, 58509, 60386, 63967, 64105, 64377, 64711, 64858, 65012, 65055, 79002, 79019, 79075, 79140, 79173, 79575, 79605, 79677, 79709, 79728, 79784, 79801, 79829, 79862, 79968, 80178, 80329, 80757, 81539, 81576, 81620, 81831, 81930, 83481, 83546, 83694, 83723, 83786, 83903, 84131, 84140, 84444, 84464, 84530, 84634, 84684, 84687, 84823, 84894, 85356, 85446, 85446, 85446, 85455, 89796, 89839, 89891, 90249, 90378, 90379, 90557, 90580, 90668, 90835, 91039, 92591, 92691, 93323, 94032, 108961, 113130, 114787, 115650, 115827, 115948, 116028, 124222, 126567, 128239, 134266, 138715, 146330, 146909, 147341, 147841, 149175, 150468, 151835, 153478, 158405, 164284, 165918, 169714, 170393, 170463, 171169, 192683, 195828, 196403, 199699, 201161, 201725, 219988, 220042, |

TABLE 5-continued

The genes in the collection of pathway signatures used in this study

| Pathway | Reference | Genes (Entrez Gene ID) |
|---|---|---|
| | | 220134, 220359, 221150, 222389, 222662, 245812, 253430, 253982, 254099, 254173, 254263, 254295, 254559, 255349, 256472, 259266, 283385, 283431, 283989, 284069, 284338, 284339, 284403, 284716, 284992, 285643, 286151, 286826, 338707, 339674, 339778, 343702, 348738, 349152, 374407, 374946, 386684, 387273, 389792, 391123, 399665, 401491, 401548, 401647, 401827, 404217, 440021, 494143, 494470, 574029, 645191, 653820, 654429, 728116, 100124700, 100130776, 100133941, 101927813, 101929705, 5426, 84642 |
| PN | Phillips et al., Cancer Cell (2006) | 108, 163, 230, 348, 403, 429, 534, 547, 650, 1038, 1272, 1410, 1645, 1826, 2037, 2047, 2147, 2257, 2258, 2259, 2550, 2556, 2562, 2571, 2746, 2747, 2774, 2775, 2890, 2891, 2893, 2894, 2900, 3131, 3400, 3745, 3782, 3798, 3821, 3823, 3983, 4093, 4094, 4137, 4168, 4330, 4675, 4684, 4915, 4926, 4974, 4978, 5017, 5027, 5046, 5067, 5138, 5164, 5166, 5590, 5662, 5730, 5881, 5911, 6125, 6137, 6167, 6252, 6319, 6328, 6445, 6456, 6505, 6509, 6571, 6585, 6751, 6752, 6886, 7067, 7079, 7168, 7477, 7915, 8502, 8549, 8787, 8812, 9026, 9185, 9229, 9241, 9568, 9699, 9844, 9846, 9892, 9951, 10014, 10083, 10129, 10203, 10215, 10276, 10580, 10633, 10683, 10690, 10718, 10882, 10900, 11074, 22885, 22986, 23017, 23046, 23220, 23236, 23373, 23492, 23493, 23542, 23544, 23769, 25789, 25817, 25956, 26032, 26033, 26050, 26052, 26232, 26999, 27087, 27254, 27344, 27439, 28514, 29106, 29767, 30812, 30845, 51560, 51704, 53342, 53616, 53826, 53829, 53844, 54988, 55022, 55217, 55273, 55553, 55612, 55966, 56288, 56475, 56479, 56521, 56884, 56899, 56961, 57338, 57348, 57406, 57447, 57453, 57512, 57628, 58473, 58504, 59277, 63827, 63876, 64093, 64101, 64376, 65258, 78986, 79176, 79187, 79754, 80309, 80351, 83698, 83937, 84440, 84457, 84502, 84631, 89874, 90362, 91752, 114788, 114805, 116154, 116173, 116448, 118738, 128414, 129049, 129807, 140767, 153811, 219654, 219736, 219931, 220164, 255426, 256987, 259217, 259232, 283455, 283576, 284244, 286499, 338645, 340554, 349136, 386618, 728215, 5414, 10777, 222389, 738, 196500, 28984, 55857, 134701, 4325, 375704, 286097, 220965, 2681, 143381, 202451, 254559, 650392, 8123, 387590, 54886 |
| MES | Phillips et al., Cancer Cell (2006) | 59, 87, 285, 290, 602, 715, 771, 861, 871, 976, 977, 1116, 1200, 1282, 1284, 1889, 1902, 1948, 2012, 2014, 2034, 2200, 2242, 2266, 2316, 2321, 2355, 2358, 2615, 2683, 3101, 3269, 3371, 3383, 3675, 3678, 3679, 3726, 3976, 4323, 4627, 4642, 5002, 5054, 5069, 5154, 5157, 5265, 5266, 5322, 5328, 5329, 5371, 5606, 5756, 5819, 6237, 6238, 6263, 6282, 6448, 6464, 6876, 7056, 7076, 7791, 8572, 8693, 8793, 8828, 8829, 9021, 9103, 9123, 9180, 9235, 9260, 9454, 9961, 10395, 10398, 10410, 10581, 10630, 11082, 11178, 22904, 25825, 26031, 26231, 27443, 29126, 30008, 30846, 50619, 51129, 51279, 51312, 53834, 53918, 55020, 55240, 56926, 56937, 56975, 56996, 57124, 57167, 57381, 57619, 63892, 64116, 79156, 80270, 80305, 81622, 81844, 83855, 83871, 84875, 90853, 91107, 114897, 126133, 140825, 196410, 199720, 221395, 284119, 284207, 388115, 399473, 647115, 8553, 55267, 9780, 100132244, 151300, 727901 |
| PRF | Phillips et al., Cancer Cell (2006) | 97, 580, 672, 699, 890, 891, 990, 995, 1017, 1029, 1031, 1058, 1062, 1063, 1111, 1164, 1719, 1869, 1894, 1964, 2013, 2146, 2177, 2491, 2730, 3070, 3148, 3161, 3598, 3673, 4001, 4085, 4116, 4171, 4175, 4291, 4678, 4751, 4867, 4925, 5074, 5111, 5163, 5303, 5393, 5480, 5558, 5634, 5888, 5932, 5965, 5984, 6119, 6240, 6241, 6474, 6491, 6790, 6941, 7112, 7153, 7272, 7298, 7398, 7465, 7518, 7913, 7979, 8089, 8208, 8833, 8836, 8914, 9134, 9140, 9360, 9493, 9735, 9768, 9787, 9833, 9837, 9928, 10036, 10040, 10051, 10052, 10403, 10592, 10605, 10635, 10733, 10926, 11130, 11169, 22823, 22995, 23089, 23366, 23397, 23421, 23461, 23658, 24137, 26271, 27101, 29957, 29969, 29980, 51203, 51514, 51605, 51659, 51668, 54821, 54970, 55055, 55110, 55151, 55215, 55329, 55355, 55521, 55732, 55839, 55871, 56938, 57001, 57415, 58487, 64105, 64149, 64151, 79022, 79733, 79980, 79989, 80173, 80204, 81853, 81930, 83540, 83879, 84057, 84250, 84283, 84288, 89891, 91057, 91687, 92092, 92610, 121227, 132430, 132884, 139886, 144455, 147841, 151246, 165055, 171586, 195828, 221662, 259266, 374618, 441054, 63926, 55010, 574036, 84791, 89876, 84984, 387103, 115106, 983, 54801, 643911, 79682, 23594, 122769, 8487 |

Identification and Validation of Molecular Subgroups

Figure 2A:
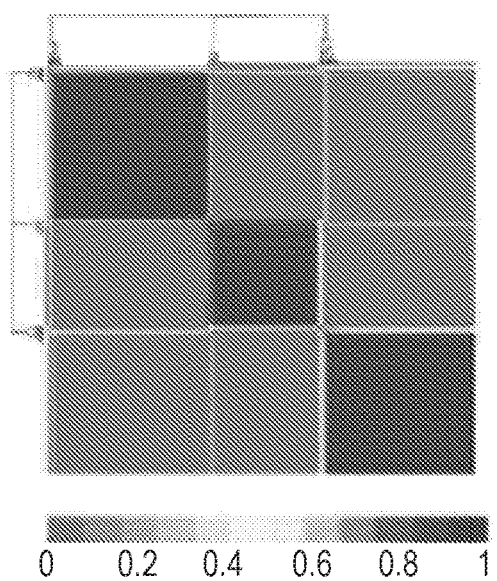
FIG. 2A-FIG. 2J illustrate, in accordance with various embodiments of the present invention, Identification and validation of novel prostate cancer subtypes.
Figure 2B:
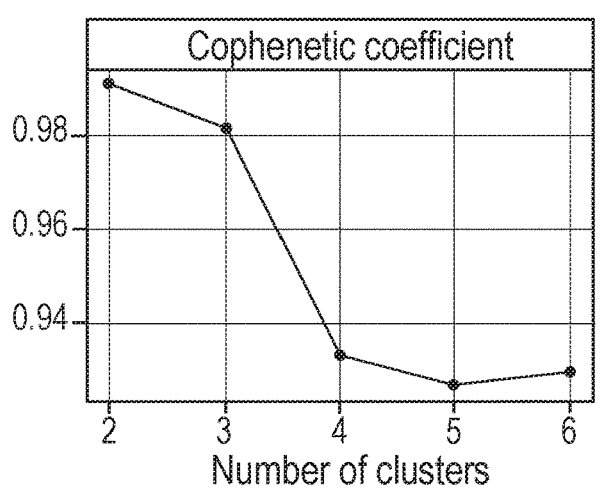
Figure 2B:
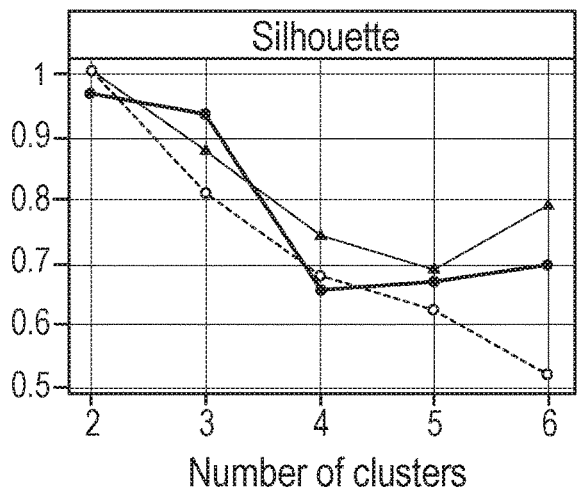
Figure 2C:
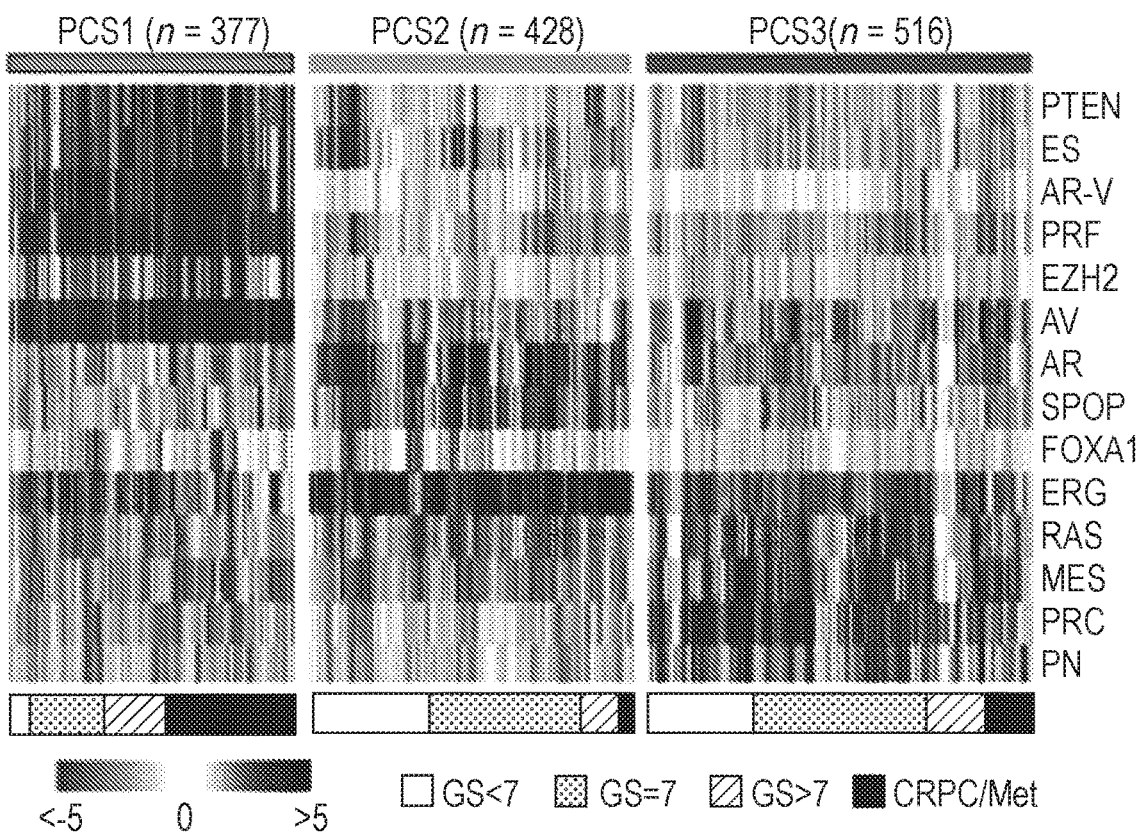
Figure 2D:
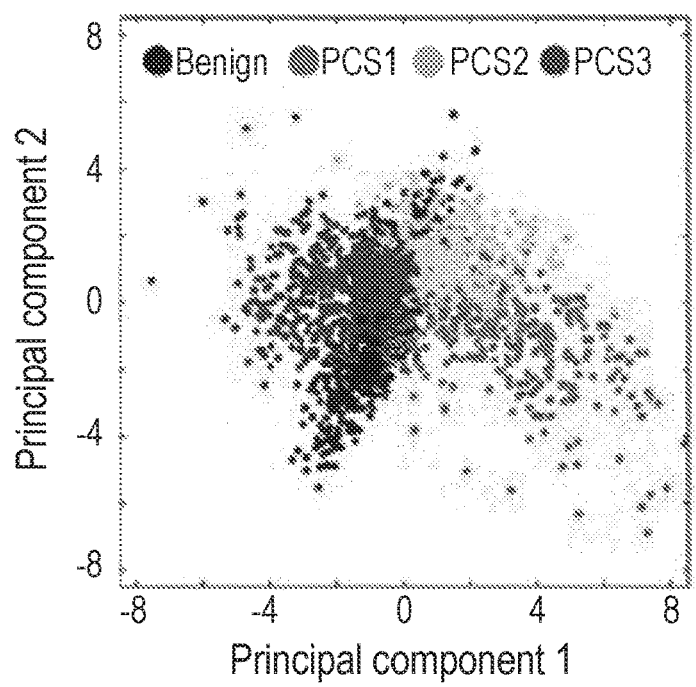
Figure 2F:
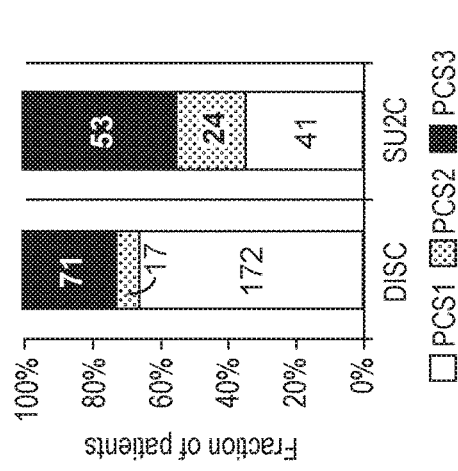
Figure 2E:
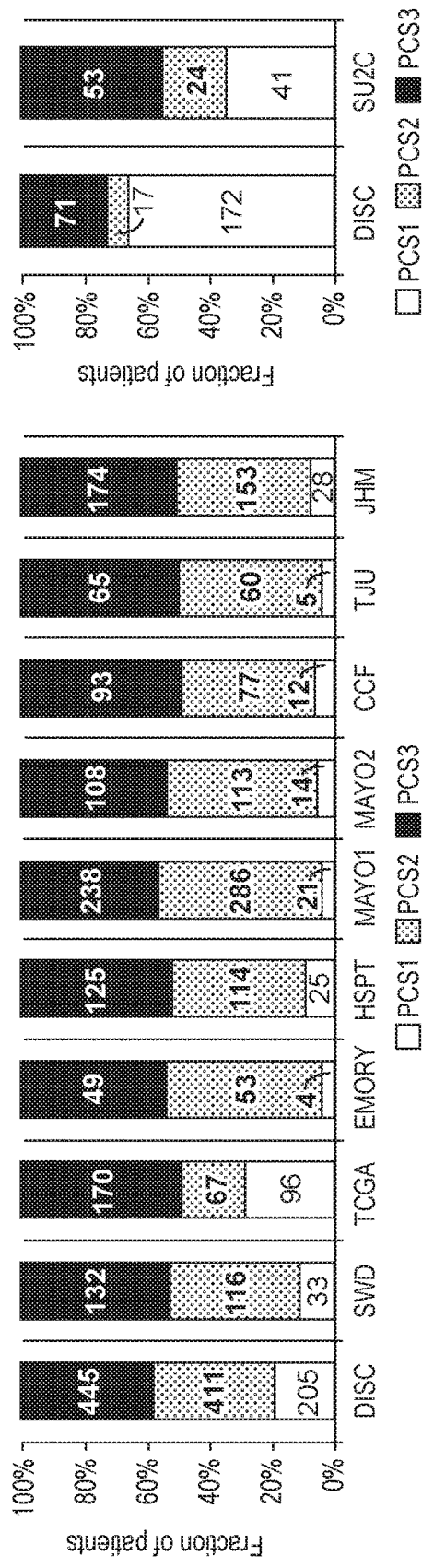
Figure 2H:
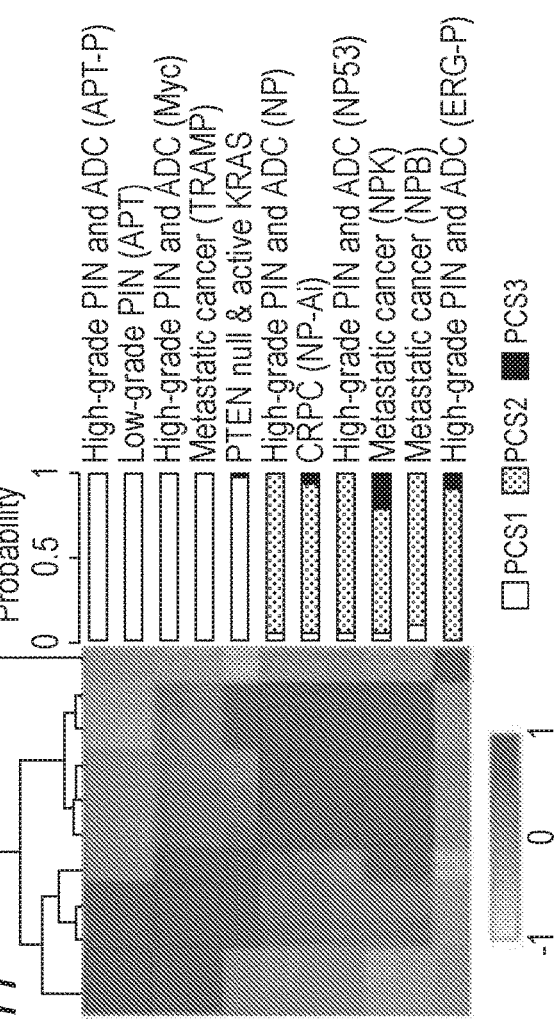
Figure 2G:
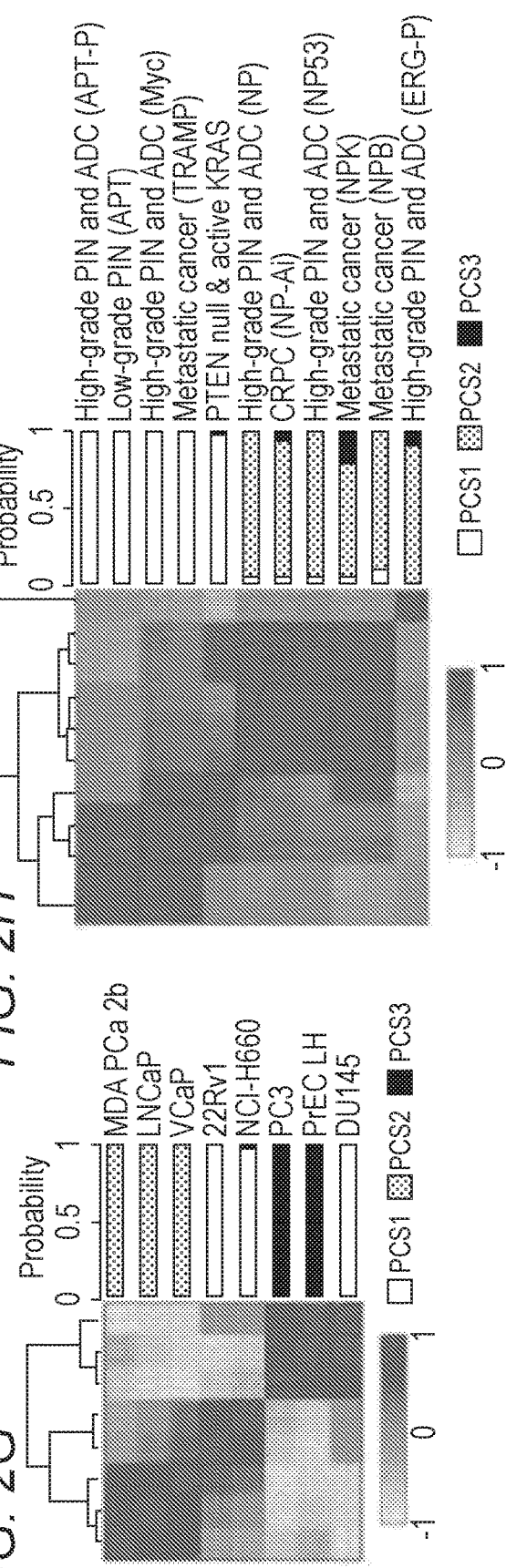
Figure 2I:
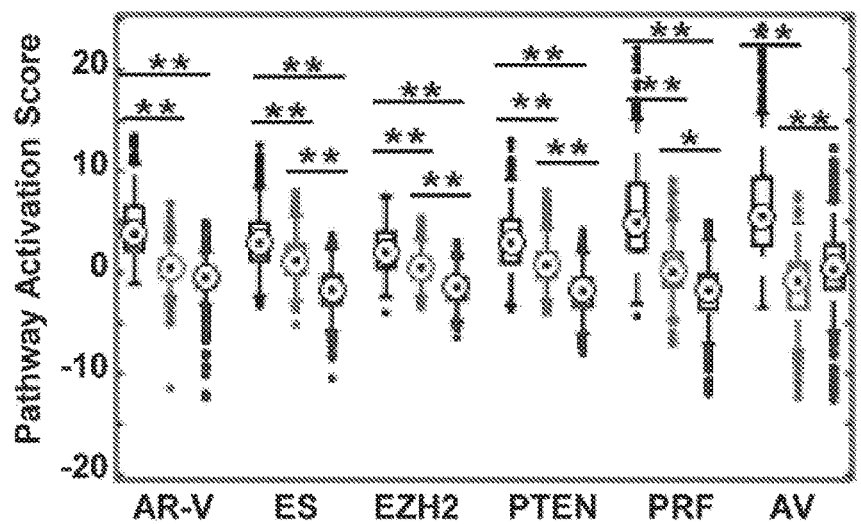
Figure 2I:
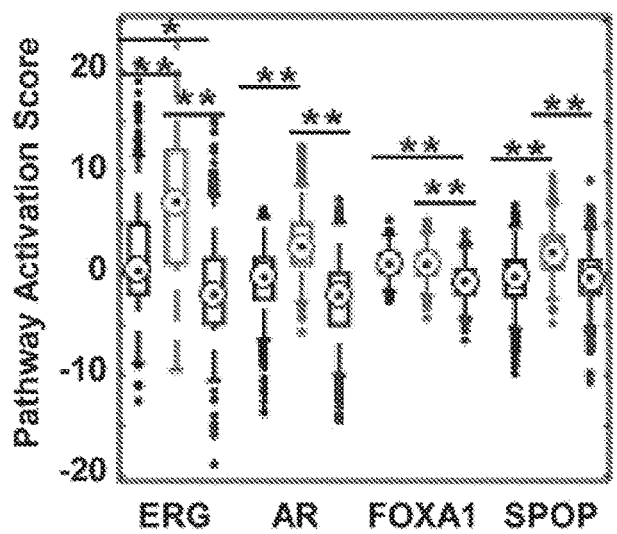
Figure 2I:
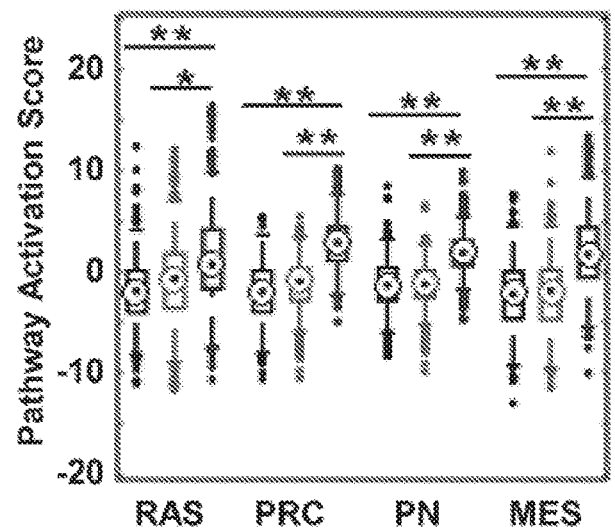

We performed unsupervised clustering based on consensus NMF clustering (Brunet J P, Tamayo P, Golub T R, Mesirov J P. Metagenes and molecular pattern discovery using matrix factorization. Proc Natl Acad Sci USA 2004; 101:4164-9) using the 14 pathway activation profiles in the DISC cohort. A consensus map of the NMF clustering results shows clear separation of the samples into three clusters (FIG. 2A). To identify the optimal number of clusters and to assess robustness of the clustering result, we computed the cophenetic coefficient and silhouette score using different numbers of clusters (Tomlins S A, Laxman B, Dhanasekaran S M, Helgeson B E, Cao X, Morris D S, et al. Distinct classes of chromosomal rearrangements create oncogenic ETS gene fusions in prostate cancer. Nature 2007; 448:595-9; Singh D, Febbo P G, Ross K, Jackson D G, Manola J, Ladd C, et al. Gene expression correlates of clinical prostate cancer behavior. Cancer Cell 2002; 1:203-9; Lapointe J, Li C, Higgins J P, van de Rijn M, Bair E, Montgomery K, et al. Gene expression profiling identifies clinically relevant subtypes of prostate cancer. Proc Natl Acad Sci USA 2004; 101:811-6; Taylor B S, Schultz N, Hieronymus H, Gopalan A, Xiao Y, Carver B S, et al. Integrative genomic profiling of human prostate cancer. Cancer Cell 2010; 18:11-22; Grasso C S, Wu Y M, Robinson D R, Cao X, Dhanasekaran S M, Khan A P, et al. The mutational landscape of lethal castration-resistant prostate cancer. Nature 2012; 487:239-43). These results indicate that 3 clusters is a statistically optimal representation of the data (FIG. 2B). A heatmap of 3 sample clusters demonstrates highly consistent pathway activation patterns within each group (FIG. 2C). These analyses suggest that the clusters correspond to three prostate cancer subtypes. We compared the magnitude of activation of each pathway across the 3 clusters evident in FIG. 2C using the Wilcoxon rank-sum test for pairwise comparisons (FIG. 2I). The PCS1 subtype exhibits high activation scores for EZH2, PTEN, PRF, ES, AV, and AR-V pathways. In contrast, ERG pathway activation predominates in PCS2, which is also characterized by high activation of AR, FOXA1, and SPOP. PCS3 exhibits high activation of RAS, PN, MES, while AR and AR-V activation are low.

Figure 2J:
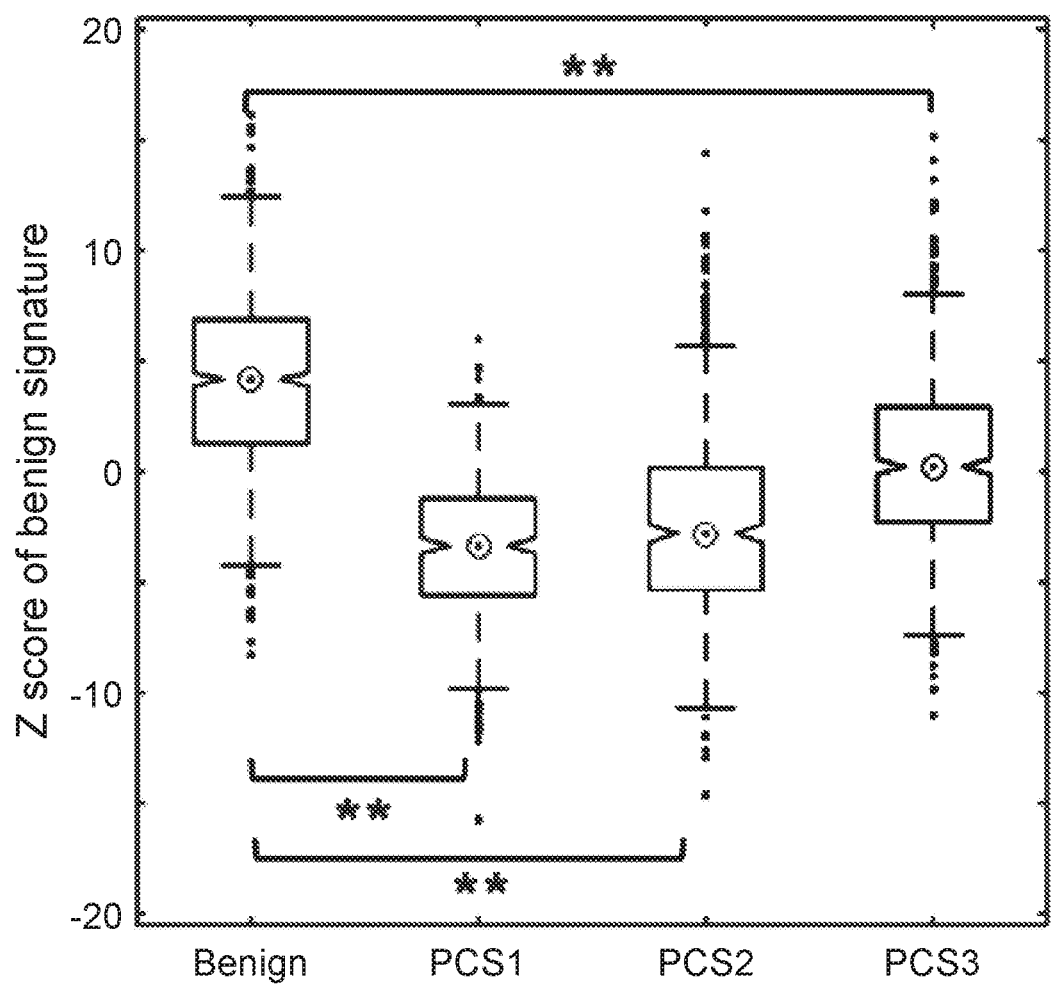

High enrichment of PRC and low AR within PCS3 raises the question of whether this subtype is an artifact of contaminating nontumor tissues. However, PCA demonstrates that samples in PCS3 are as distinct from benign tissues as samples in the other subtypes (FIG. 2D). To further confirm the difference from benign tissue, we made use of a gene signature shown to discriminate benign prostate tissue from cancer in a previous study (Stuart R O, Wachsman W, Berry C C, Wang-Rodriguez J, Wasserman L, Klacansky I, et al. In silico dissection of cell-type-associated patterns of gene expression in prostate cancer. Proc Natl Acad Sci USA 2004; 101:615-20) and found a significant difference ($P<0.001$) in all the tumors in the subtypes compared with benign tissues (FIG. 2J). These results demonstrate that prostate cancers retain distinct gene expression profiles between subtypes, which are not related to the amount of normal tissue contamination.

To validate the PCS classification scheme, a 14-pathway classifier was developed using a naïve Bayes machine learning algorithm (see details in Materials and Methods). This classifier was applied to 9 independent cohorts of localized tumors (i.e., SWD, TCGA, EMORY, HSPT, MAYO1/2, CCF, TJU, and JHM) and the SU2C cohort of CRPC/Met tumors. Out of these 10 independent cohorts, 5 cohorts (i.e., MAYO1/2, TJU, CCF, and JHM) were from the GRID (FIG. 2E; Table 1; Tomlins S A, Alshalalfa M, Davicioni E, Erho N, Yousefi K, Zhao S, et al. Characterization of 1577 primary prostate cancers reveals novel biological and clinicopathologic insights into molecular subtypes. Eur Urol 2015; 68:555-67). The 14-pathway classifier reliably categorized tumors in the DISC cohort into 3 subtypes, with an average classification performance=0.89 ($P<0.001$). The 3 subtypes were identified in all cohorts. Their proportions were similar across the localized disease cohorts, demonstrating the consistency of the classification algorithm across multiple practice settings (FIG. 2E). The 2 cohorts consisting of CRPC/Met tumors (DISC and SU2C) showed some differences in the frequency of PCS1 and PCS3; the most frequent subtype in the DISC CRPC/Met cohort was PCS1 (66%), while the most frequent subtype in SU2C was PCS3 (45%; FIG. 2F). PCS2 was the minor subtype in both CRPC/Met cohorts.

To determine whether the PCS classification is relevant to laboratory models of prostate cancer, we analyzed 8 human prostate cancer cell lines from The Cancer Cell Line Encyclopedia (CCLE; GSE36133; Barretina J, Caponigro G, Stransky N, Venkatesan K, Margolin A A, Kim S, et al. The Cancer Cell Line Encyclopedia enables predictive modelling of anticancer drug sensitivity. Nature 2012; 483:603-7 and 11 prostate cancer mouse models (Aytes A, Mitrofanova A, Lefebvre C, Alvarez M J, Castillo-Martin M, Zheng T, et al. Cross-species regulatory network analysis identifies a synergistic interaction between FOXM1 and CENPF that drives prostate cancer malignancy. Cancer Cell 2014; 25:638-51; Mulholland D J, Kobayashi N, Ruscetti M, Zhi A, Tran L M, Huang J, et al. Pten loss and RAS/MAPK activation cooperate to promote EMT and metastasis initiated from prostate cancer stem/progenitor cells. Cancer Res 2012; 72:1878-89). There are two datasets for mouse models. The first dataset (GSE53202) contains transcriptome profiles of 13 genetically engineered mouse models, including normal epithelium (i.e., wild-type), low-grade PIN (i.e., Nkx3.1 and APT), high-grade PIN, and adenocarcinoma (i.e., APT-P, APC, Myc, NP, Erg-P, and NP53), CRPC (i.e., NP-Ai), and metastatic prostate cancer (i.e., NPB, NPK, and TRAMP). Because of no available data for samples without drug treatment, the Nkx3.1 and APC models were excluded from this analysis. The second dataset (GSE34839) contains transcriptome profiles from mice with PTEN-null/KRAS activation mutation-driven high-grade, invasive prostate cancer and mice with only the PTEN-null background. This analysis revealed that all 3 prostate cancer subtypes were represented in the 8 human prostate cancer cell lines (FIG. 2G), while only 2 subtypes (PCS1 and PCS2) were represented in the mouse models (FIG. 2H). This result provides evidence that the subtypes are recapitulated in genetically engineered mouse models and persist in human cancer cells in cell culture.

Evaluation of PCS Subtypes in Comparison with Other Subtypes

Several categorization schemes of prostate cancer have been described, based mostly on tumor-specific genomic alterations and in some cases with integration of transcriptomic and other profiling data (Markert E K, Mizuno H, Vazquez A, Levine A J. Molecular classification of prostate cancer using curated expression signatures. Proc Natl Acad Sci USA 2011; 108:21276-81; Tomlins S A, Alshalalfa M, Davicioni E, Erho N, Yousefi K, Zhao S, et al. Characterization of 1577 primary prostate cancers reveals novel biological and clinicopathologic insights into molecular subtypes. Eur Urol 2015; 68:555-67; Erho N, Crisan A, Vergara I A, Mitra A P, Ghadessi M, Buerki C, et al. Discovery and validation of a prostate cancer genomic classifier that predicts early metastasis following radical prostatectomy. PLoS One 2013; 8:e66855). This prompted us to compare the PCS classification scheme with the genomic subtypes derived by TCGA (Cancer Genome Atlas Research Network. Electronic address scmo, Cancer Genome Atlas Research N. The Molecular Taxonomy of Primary Prostate Cancer. Cell 2015; 163:1011-25), because comprehensive genomic categorization was recently made available (Robinson D, Van Allen E M, Wu Y M, Schultz N, Lonigro R J, Mosquera J M, et al. Integrative clinical genomics of advanced prostate cancer. Cell 2015; 161:1215-28). We also compared the PCS classification with the subtypes recently defined by Tomlins and colleagues from RNA expression data (Tomlins S A, Alshalalfa M, Davicioni E, Erho N, Yousefi K, Zhao S, et al. Characterization of 1577 primary prostate cancers reveals novel biological and clinicopathologic insights into molecular subtypes. Eur Urol 2015; 68:555-67). The Tomlins subtyping scheme is defined using the 7 GRID cohorts (i.e., MAYO1/2, TJU, CCF, MSKCC, EMC, and JHM) that we used for validating the PCS system. The large number of cases in the 7 GRID cohorts (n=1,626) is comparable with our DISC cohort in terms of heterogeneity and complexity. TCGA identified several genomic subtypes, named ERG, ETV1, ETV4, FLI1, SPOP, FOXA1, IDH1, and "other." Tomlins and colleagues described 4 subtypes based on microarray gene expression patterns that are related to several genomic aberrations [i.e., ERG±, ETS±, SPINK1±, and triple negative (ERG⁻/ETS⁻/SPINK1⁻)].

Figure 3A:
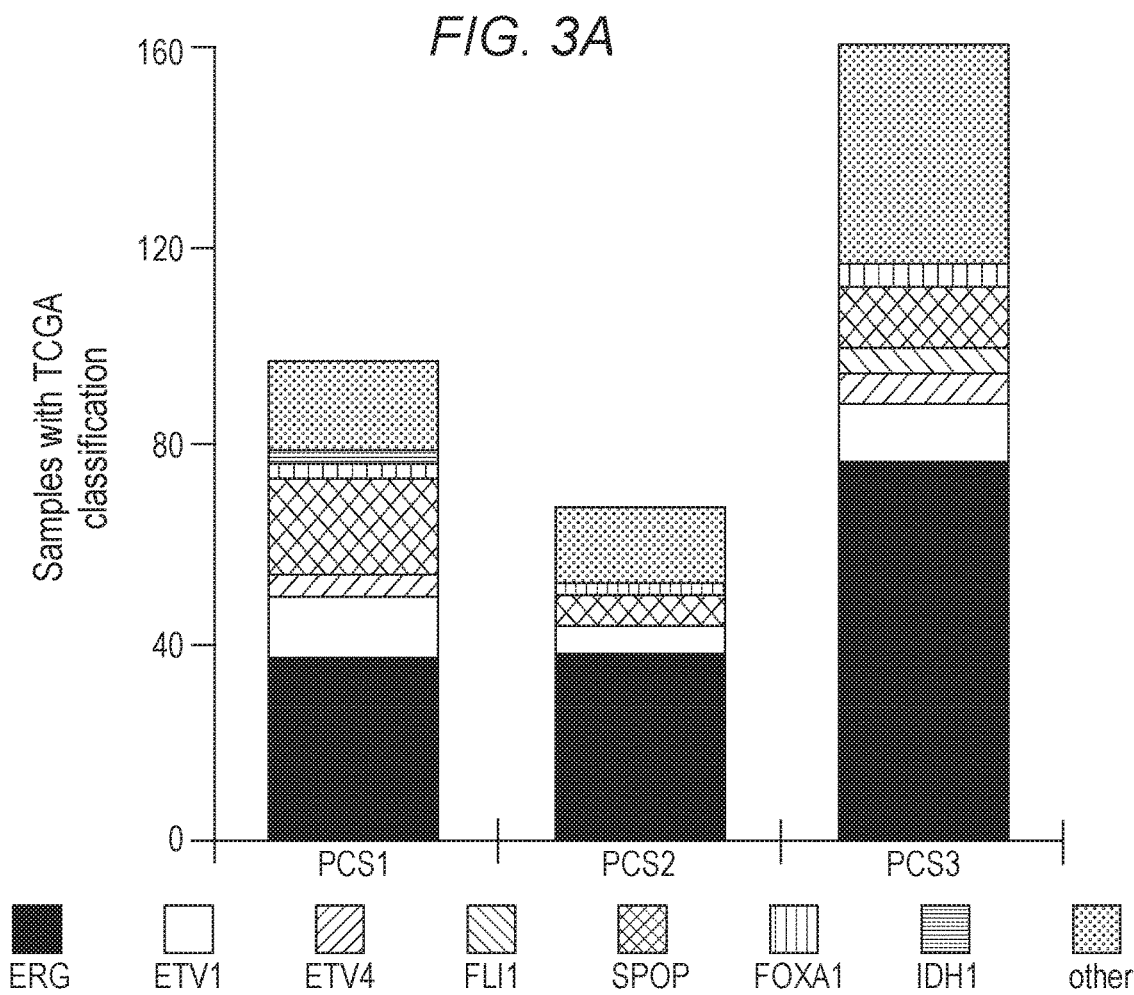
Figure 3B:
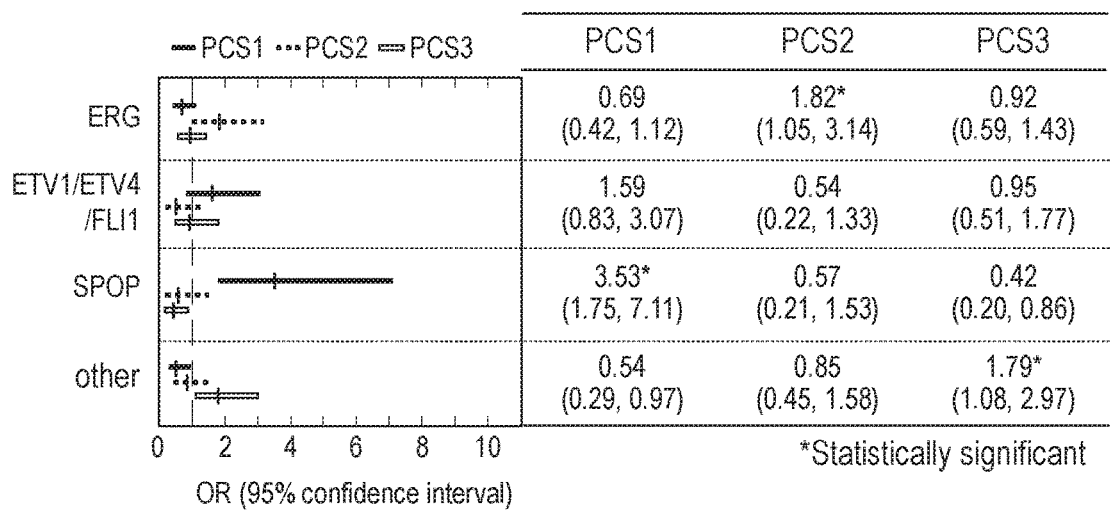
Figure 3C:
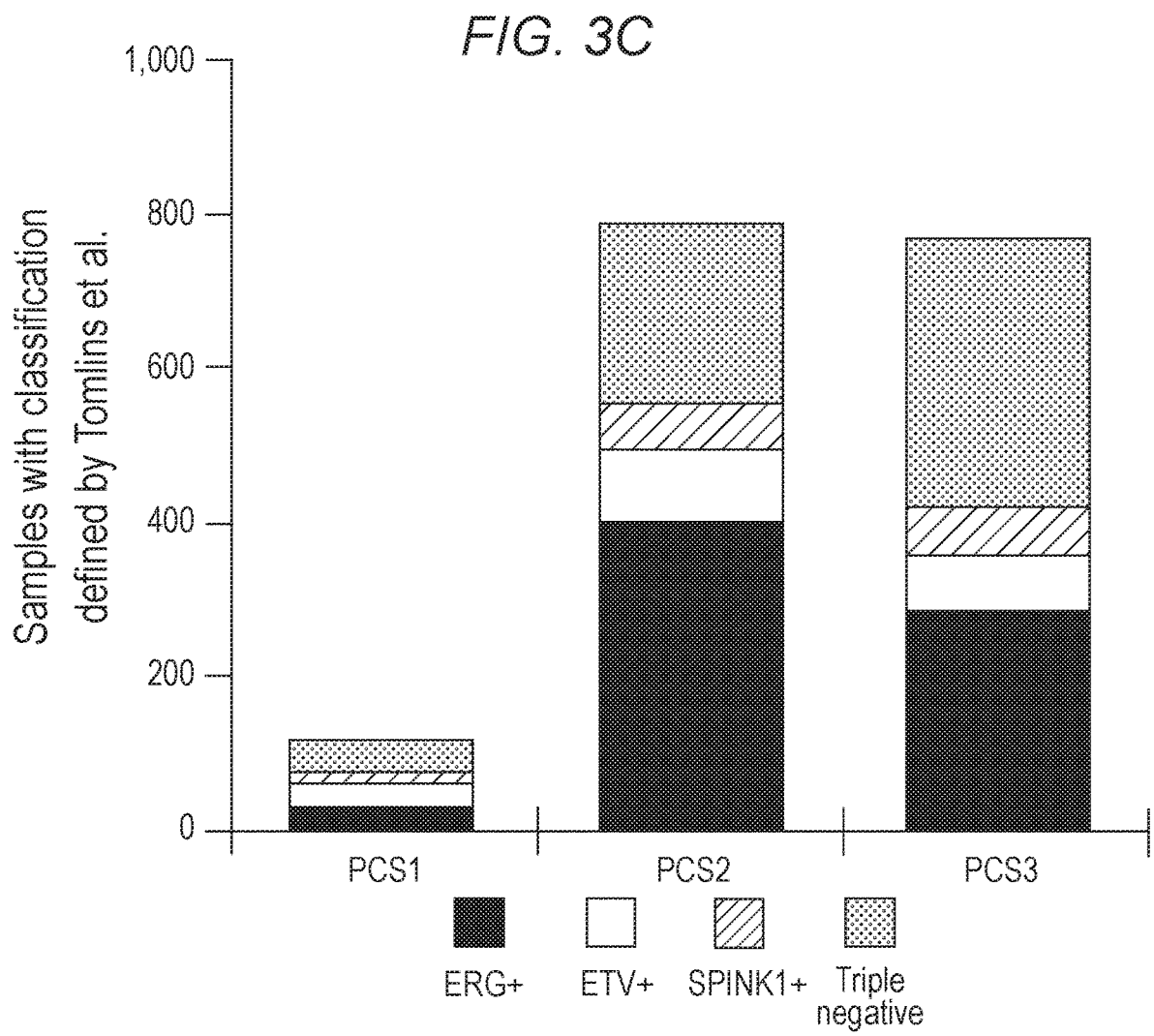
Figure 3D:
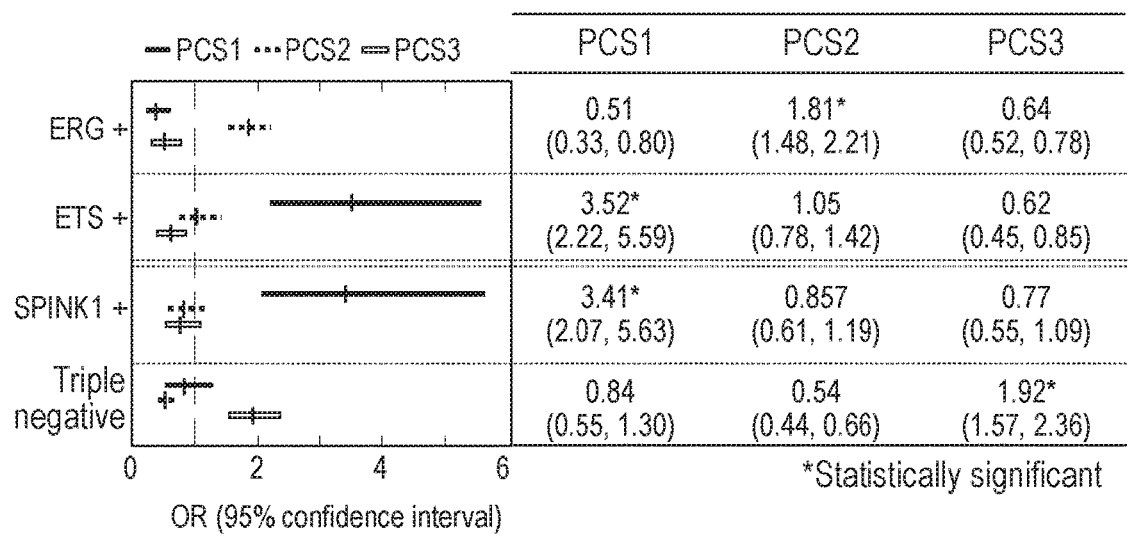
Figure 3E:
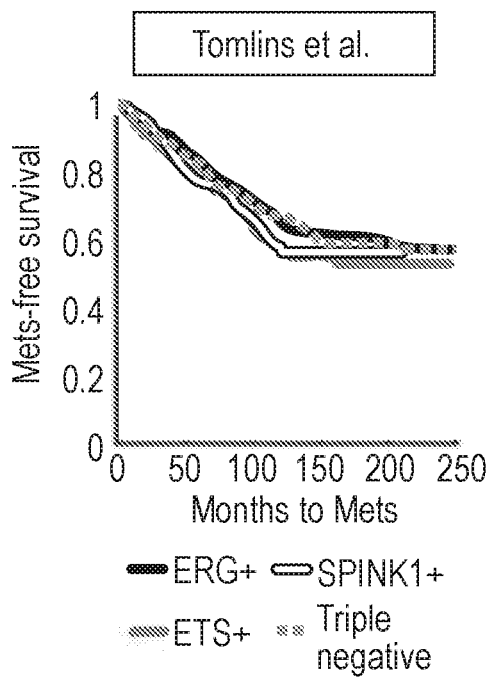
Figure 3F:
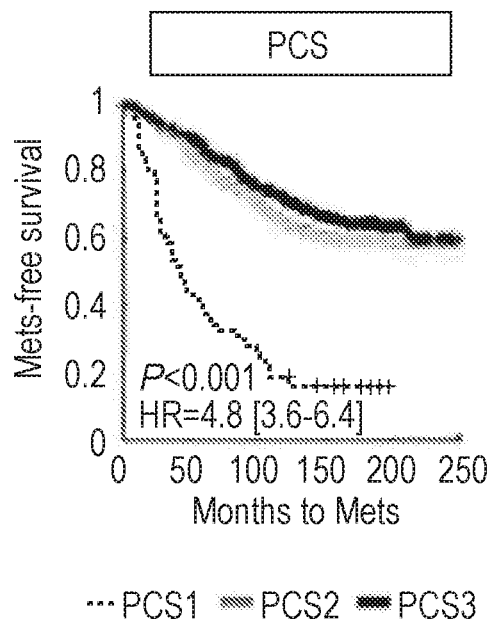

A comparison of the PCS categories with the TCGA genomic subtypes showed that the tumors classified as ERG, ETV1/4, SPOP, FOXA1, and "other" were present across all the PCS categories in the TCGA dataset (n=333; FIG. 3A). SPOP cancers were enriched in PCS1 (OR: 3.53), while PCS2 tumors were overrepresented in TCGA/ERG cancers (OR: 1.82) and TCGA/"other" cancers were enriched in PCS3 (OR: 1.79; FIG. 3B). In the GRID cohorts, we observed all PCS categories in all classification groups as defined by Tomlins and colleagues (FIG. 3C and FIG. 3D). We found a high frequency of the Tomlins/ERG± subtype in PCS2, but not in PCS1. PCS1 was enriched for Tomlins/ETS± and Tomlins/SPINK1± subtypes, while PCS3 was enriched for the triple-negative subtype but not the ERG± or ETS± subgroups. Finally, we compared the Tomlins classification method with the PCS classification using 5 of 7 GRID cohorts. PCS1 demonstrated significantly shorter metastasis-free survival compared with PCS2 and PCS3 ($P<0.001$; FIG. 3E). In contrast, no difference in metastatic progression was seen among the Tomlins categories (FIG. 3F).

Figure 3G:
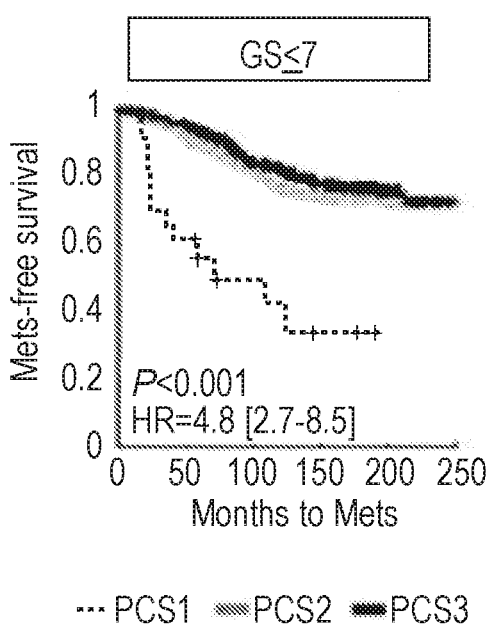
Figure 3G:
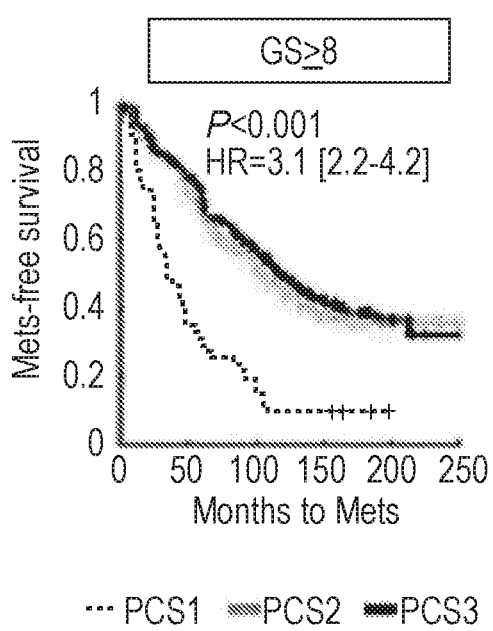

PCS1 contained the largest number of prostate cancers with GS>8 (FIG. 2C). Given the overall poorer outcomes seen in PCS1 tumors, we tested whether this result was simply a reflection of the enrichment of high-grade disease in this group (i.e., GS>8). For this analysis, we merged 5 GRID cohorts (i.e., MAYO1/2, TJU, CCF, and JHM) into a single dataset and separately analyzed low and high-grade disease. We observed a similarly significant ($P<0.001$) association between subtypes and metastasis-free survival in GS<7 and in GS>8 (FIG. 3G). Thus, tumors in the PCS1 group exhibit the poorest prognosis, including in tumors with low Gleason sum score. Finally, in the DISC cohort, although CRPC/Met tumors were present in all PCS categories, PCS1 predominated (66%), followed by PCS3 (27%) and PCS2 (7%) tumors. To confirm whether this clinical correlation is replicated in individual cohorts, we also assessed association with time to metastatic progression, prostate cancer-specific mortality (PCSM), and overall survival (OS) in 5 individual cohorts in the GRID (i.e., MAYO1/2, CCF, TJU, and JHM) and in the SWD cohorts. PCS1 was seen to be the most aggressive subtype, consistent with the above results (FIG. 3H(i-x)).

PCS Categories Possess Characteristics of Basal and Luminal Prostate Epithelial Cells Prostate cancer may arise from oncogenic transformation of different cell types in glandular prostate epithelium (Goldstein A S, Huang J, Guo C, Garraway I P, Witte O N. Identification of a cell of origin for human prostate cancer. Science 2010; 329:568-71; Wang Z A, Mitrofanova A, Bergren S K, Abate-Shen C, Cardiff R D, Califano A, et al. Lineage analysis of basal epithelial cells reveals their unexpected plasticity and supports a cell-of-origin model for prostate cancer heterogeneity. Nat Cell Biol 2013; 15:274-83; Baird A A, Muir T C. Membrane hyperpolarization, cyclic nucleotide levels and relaxation in the guinea-pig internal anal sphincter. Br J Pharmacol 1990; 100:329-35).

Breast cancers can be categorized into luminal and basal subtypes, which are associated with different patient outcomes (Visvader J E. Keeping abreast of the mammary epithelial hierarchy and breast tumorigenesis. Genes Dev 2009; 23:2563-77). It is unknown whether this concept applies to human prostate cancer. To examine whether the 3 PCS categories are a reflection of different cell types, we identified 428 SEGs (SEG1-3; 86 for PCS1, 123 for PCS2, and 219 for PCS3; Table 6) in each subtype. As expected, these genes are involved in pathways that are enriched in each subtype (FIG. 4A) and that define the perturbed cellular processes of the subtype. We then identified the cellular processes that are associated with the SEGs. Proliferation and lipid/steroid metabolism are characteristic of SEG1 and SEG2, while extracellular matrix organization, inflammation, and cell migration are characteristic of SEG3 (FIG. 4B). This result suggests that distinct biological functions are associated with the PCS categories.

TABLE 6

List of 428 SEGs.

Figure 4A:
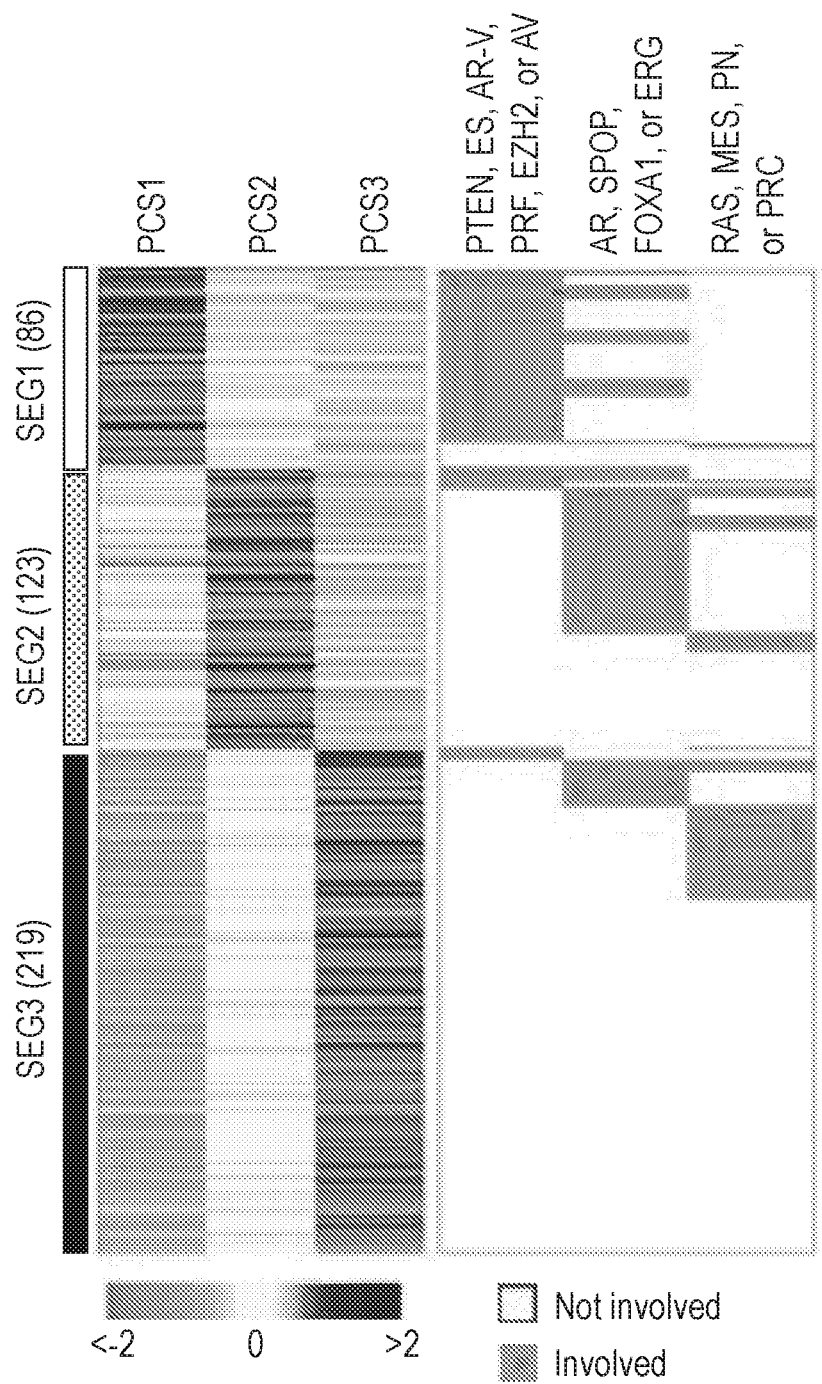
FIG. 4A-FIG. 4E illustrates, in accordance with various embodiments of the present invention, genes enriched in each of the three subtypes are associated with luminal and basal cell features.
Figures 4B, 4C:
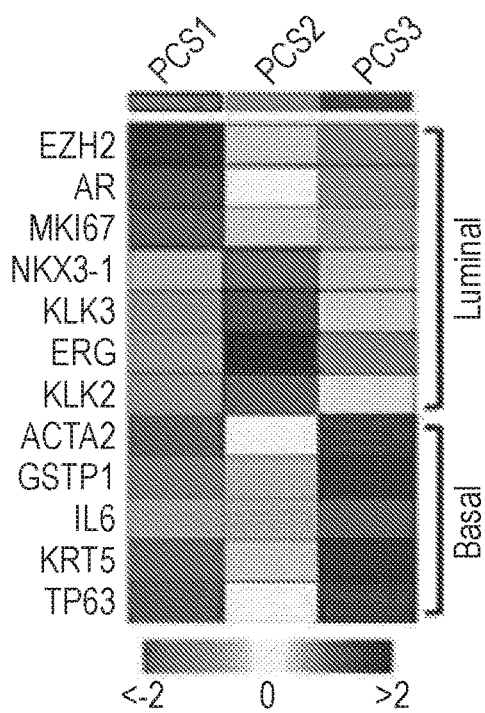
Figure 4D:
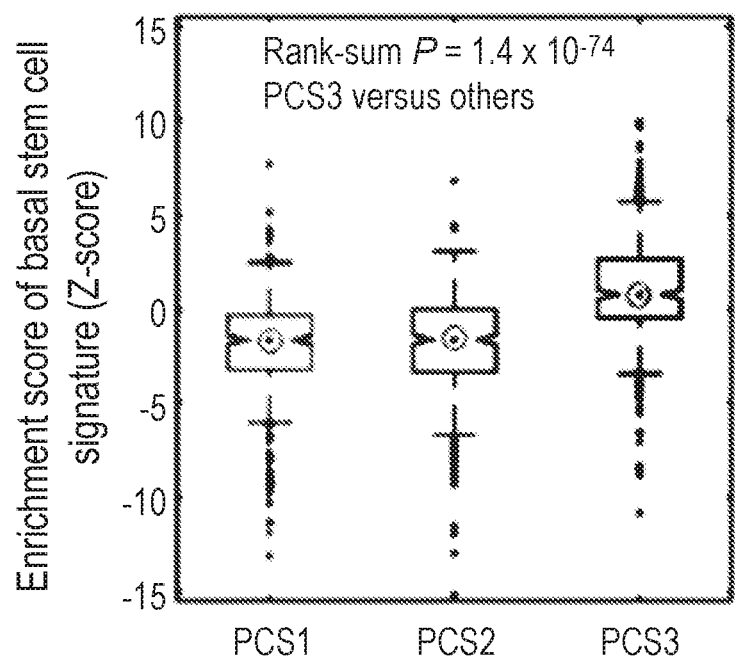

| FIG. 4A Order | Entrez Gene ID | Symbol | Sub-type ID | Fold change in PCS1 | Fold change in PCS2 | Fold change in PCS3 |
| --- | --- | --- | --- | --- | --- | --- |
| 1 | 699 | BUB1 | 1 | 0.733 | −0.29 | −0.359 |
| 2 | 24137 | KIF4A | 1 | 0.797 | −0.36 | −0.354 |
| 3 | 890 | CCNA2 | 1 | 0.705 | −0.23 | −0.389 |
| 4 | 1062 | CENPE | 1 | 0.607 | −0.25 | −0.29 |
| 5 | 1164 | CKS2 | 1 | 1.037 | −0.26 | −0.649 |
| 6 | 9787 | DLGAP5 | 1 | 0.832 | −0.31 | −0.423 |
| 7 | 11004 | KIF2C | 1 | 0.737 | −0.37 | −0.289 |
| 8 | 701 | BUB1B | 1 | 0.742 | −0.23 | −0.428 |
| 9 | 983 | CDK1 | 1 | 0.965 | −0.3 | −0.547 |
| 10 | 990 | CDC6 | 1 | 0.617 | −0.17 | −0.374 |
| 11 | 1058 | CENPA | 1 | 0.704 | −0.34 | −0.291 |
| 12 | 9493 | KIF23 | 1 | 0.61 | −0.32 | −0.227 |
| 13 | 891 | CCNB1 | 1 | 0.796 | −0.16 | −0.539 |
| 14 | 991 | CDC20 | 1 | 0.918 | −0.46 | −0.365 |
| 15 | 1063 | CENPF | 1 | 1.176 | −0.45 | −0.593 |
| 16 | 3161 | HMMR | 1 | 0.917 | −0.29 | −0.519 |
| 17 | 6241 | RRM2 | 1 | 0.963 | −0.26 | −0.582 |
| 18 | 6790 | AURKA | 1 | 0.789 | −0.26 | −0.435 |
| 19 | 9133 | CCNB2 | 1 | 0.869 | −0.2 | −0.561 |
| 20 | 9232 | PTTG1 | 1 | 1.163 | −0.55 | −0.492 |
| 21 | 9735 | KNTC1 | 1 | 0.611 | −0.26 | −0.287 |
| 22 | 9928 | KIF14 | 1 | 0.58 | −0.32 | −0.203 |
| 23 | 11130 | ZWINT | 1 | 0.904 | −0.19 | −0.602 |
| 24 | 51203 | NUSAP1 | 1 | 1.089 | −0.33 | −0.632 |
| 25 | 113130 | CDCA5 | 1 | 0.688 | −0.3 | −0.311 |
| 26 | 259266 | ASPM | 1 | 0.913 | −0.38 | −0.434 |
| 27 | 4173 | MCM4 | 1 | 0.662 | −0.25 | −0.341 |
| 28 | 9768 | KIAA0101 | 1 | 1.068 | −0.27 | −0.668 |
| 29 | 22974 | TPX2 | 1 | 1.099 | −0.39 | −0.579 |
| 30 | 29128 | UHRF1 | 1 | 0.748 | −0.35 | −0.316 |
| 31 | 51514 | DTL | 1 | 0.687 | −0.36 | −0.262 |
| 32 | 332 | BIRC5 | 1 | 0.927 | −0.4 | −0.423 |
| 33 | 1894 | ECT2 | 1 | 0.654 | 0.15 | −0.698 |
| 34 | 2171 | FABP5 | 1 | 0.59 | −0.08 | −0.428 |
| 35 | 4001 | LMNB1 | 1 | 0.691 | −0.26 | −0.357 |
| 36 | 7153 | TOP2A | 1 | 1.213 | −0.33 | −0.733 |
| 37 | 7272 | TTK | 1 | 0.785 | −0.2 | −0.493 |
| 38 | 7298 | TYMS | 1 | 0.717 | −0.34 | −0.303 |
| 39 | 8318 | CDC45 | 1 | 0.602 | −0.25 | −0.286 |
| 40 | 9088 | PKMYT1 | 1 | 0.608 | −0.37 | −0.182 |
| 41 | 9833 | MELK | 1 | 1.008 | −0.35 | −0.538 |
| 42 | 10112 | KIF20A | 1 | 0.878 | −0.38 | −0.406 |
| 43 | 11113 | CIT | 1 | 0.587 | −0.35 | −0.181 |
| 44 | 54845 | ESRP1 | 1 | 0.61 | 0.232 | −0.736 |
| 45 | 55355 | HJURP | 1 | 0.656 | −0.23 | −0.347 |
| 46 | 64151 | NCAPG | 1 | 0.872 | −0.35 | −0.429 |
| 47 | 79019 | CENPM | 1 | 0.59 | −0.31 | −0.221 |
| 48 | 81831 | NETO2 | 1 | 0.61 | 0.162 | −0.672 |
| 49 | 55502 | HES6 | 1 | 0.604 | −0.27 | −0.273 |

TABLE 6-continued

List of 428 SEGs.

| FIG. 4A Order | Entrez Gene ID | Symbol | Sub-type ID | Fold change in PCS1 | Fold change in PCS2 | Fold change in PCS3 |
|---|---|---|---|---|---|---|
| 50 | 2146 | EZH2 | 1 | 1.007 | −0.2 | −0.676 |
| 51 | 7366 | UGT2B15 | 1 | 0.609 | −0.43 | −0.122 |
| 52 | 54443 | ANLN | 1 | 0.696 | −0.32 | −0.3 |
| 53 | 54892 | NCAPG2 | 1 | 0.611 | −0.12 | −0.416 |
| 54 | 56992 | KIF15 | 1 | 0.699 | −0.31 | −0.312 |
| 55 | 83540 | NUF2 | 1 | 0.753 | −0.31 | −0.358 |
| 56 | 213 | ALB | 1 | 0.631 | −0.32 | −0.249 |
| 57 | 367 | AR | 1 | 0.739 | −0.09 | −0.555 |
| 58 | 2305 | FOXM1 | 1 | 0.693 | −0.34 | −0.279 |
| 59 | 3148 | HMGB2 | 1 | 0.594 | −0.18 | −0.346 |
| 60 | 3832 | KIF11 | 1 | 0.603 | −0.21 | −0.326 |
| 61 | 3925 | STMN1 | 1 | 0.756 | −0.2 | −0.465 |
| 62 | 4288 | MKI67 | 1 | 0.634 | −0.18 | −0.382 |
| 63 | 7083 | TK1 | 1 | 0.835 | −0.49 | −0.267 |
| 64 | 9055 | PRC1 | 1 | 0.881 | −0.29 | −0.487 |
| 65 | 9134 | CCNE2 | 1 | 0.6 | −0.18 | −0.353 |
| 66 | 9156 | EXO1 | 1 | 0.604 | −0.31 | −0.235 |
| 67 | 10024 | TROAP | 1 | 0.723 | −0.39 | −0.26 |
| 68 | 10460 | TACC3 | 1 | 0.619 | −0.38 | −0.185 |
| 69 | 11065 | UBE2C | 1 | 1.164 | −0.47 | −0.566 |
| 70 | 29089 | UBE2T | 1 | 0.894 | −0.39 | −0.411 |
| 71 | 29127 | RACGAP1 | 1 | 0.749 | −0.24 | −0.42 |
| 72 | 55143 | CDCA8 | 1 | 0.619 | −0.26 | −0.287 |
| 73 | 55165 | CEP55 | 1 | 0.698 | −0.28 | −0.336 |
| 74 | 55872 | PBK | 1 | 0.895 | −0.34 | −0.458 |
| 75 | 79682 | MLF1IP | 1 | 0.8 | −0.17 | −0.531 |
| 76 | 374393 | FAM111B | 1 | 0.581 | −0.19 | −0.326 |
| 77 | 3223 | HOXC6 | 1 | 0.633 | 0.21 | −0.735 |
| 78 | 1033 | CDKN3 | 1 | 0.868 | −0.29 | −0.481 |
| 79 | 1951 | CELSR3 | 1 | 0.659 | −0.39 | −0.202 |
| 80 | 6472 | SHMT2 | 1 | 0.599 | −0.03 | −0.485 |
| 81 | 6696 | SPP1 | 1 | 0.841 | −0.37 | −0.383 |
| 82 | 8438 | RAD54L | 1 | 0.618 | −0.32 | −0.234 |
| 83 | 10615 | SPAG5 | 1 | 0.785 | −0.31 | −0.387 |
| 84 | 10721 | POLQ | 1 | 0.581 | −0.28 | −0.238 |
| 85 | 29923 | HILPDA | 1 | 0.796 | −0.31 | −0.4 |
| 86 | 51155 | HN1 | 1 | 0.631 | −0.13 | −0.419 |
| 87 | 8611 | PPAP2A | 2 | −0.23 | 0.73 | −0.472 |
| 88 | 10551 | AGR2 | 2 | −0.58 | 0.974 | −0.395 |
| 89 | 4824 | NKX3-1 | 2 | −0.31 | 0.585 | −0.276 |
| 90 | 4072 | EPCAM | 2 | 0.349 | 0.63 | −0.879 |
| 91 | 5865 | RAB3B | 2 | −0.18 | 0.895 | −0.672 |
| 92 | 6480 | ST6GAL1 | 2 | −0.56 | 0.691 | −0.159 |
| 93 | 23671 | TMEFF2 | 2 | 0.147 | 0.789 | −0.852 |
| 94 | 262 | AMD1 | 2 | −0.32 | 0.657 | −0.326 |
| 95 | 10040 | TOM1L1 | 2 | −0.03 | 0.611 | −0.537 |
| 96 | 384 | ARG2 | 2 | −0.45 | 0.625 | −0.192 |
| 97 | 776 | CACNA1D | 2 | 0.129 | 0.628 | −0.688 |
| 98 | 2982 | GUCY1A3 | 2 | −0.09 | 0.655 | −0.527 |
| 99 | 6675 | UAP1 | 2 | −0 | 0.682 | −0.624 |
| 100 | 354 | KLK3 | 2 | −0.56 | 0.738 | −0.196 |
| 101 | 2153 | F5 | 2 | 0.265 | 0.774 | −0.939 |
| 102 | 3109 | HLA-DMB | 2 | −0.43 | 0.833 | −0.399 |
| 103 | 3781 | KCNN2 | 2 | −0.02 | 0.834 | −0.751 |
| 104 | 10257 | ABCC4 | 2 | −0.04 | 0.841 | −0.741 |
| 105 | 27347 | STK39 | 2 | −0.13 | 0.623 | −0.458 |
| 106 | 57630 | SH3RF1 | 2 | 0.047 | 0.602 | −0.594 |
| 107 | 445347 | TARP | 2 | −0.14 | 0.94 | −0.743 |
| 108 | 1298 | COL9A2 | 2 | −0.19 | 0.674 | −0.453 |
| 109 | 1803 | DPP4 | 2 | −0.86 | 0.714 | 0.082 |
| 110 | 2690 | GHR | 2 | −0.43 | 0.657 | −0.24 |
| 111 | 4646 | MYO6 | 2 | 0.077 | 0.905 | −0.898 |
| 112 | 81035 | COLEC12 | 2 | −0.09 | 0.589 | −0.468 |
| 113 | 55 | ACPP | 2 | −1.24 | 0.798 | 0.326 |
| 114 | 220 | ALDH1A3 | 2 | −0.75 | 0.875 | −0.16 |
| 115 | 288 | ANK3 | 2 | −0.18 | 0.585 | −0.386 |
| 116 | 1718 | DHCR24 | 2 | −0.1 | 0.661 | −0.519 |
| 117 | 1824 | DSC2 | 2 | −0.17 | 0.732 | −0.528 |
| 118 | 2078 | ERG | 2 | −0.48 | 1.143 | −0.643 |
| 119 | 2152 | F3 | 2 | −0.77 | 0.7 | 0.014 |
| 120 | 2181 | ACSL3 | 2 | −0.16 | 0.777 | −0.579 |
| 121 | 2331 | FMOD | 2 | −0.97 | 0.848 | 0.049 |
| 122 | 2650 | GCNT1 | 2 | −0.1 | 0.819 | −0.671 |
| 123 | 2705 | GJB1 | 2 | −0.16 | 0.678 | −0.484 |
| 124 | 3249 | HPN | 2 | 0.233 | 0.714 | −0.856 |
| 125 | 3817 | KLK2 | 2 | −0.52 | 0.619 | −0.124 |
| 126 | 3936 | LCP1 | 2 | −0.58 | 0.625 | −0.081 |
| 127 | 4070 | TACSTD2 | 2 | −0.68 | 0.711 | −0.069 |
| 128 | 4477 | MSMB | 2 | −1.67 | 0.865 | 0.635 |
| 129 | 4604 | MYBPC1 | 2 | −0.68 | 0.713 | −0.071 |
| 130 | 5238 | PGM3 | 2 | −0.12 | 0.676 | −0.522 |
| 131 | 5530 | PPP3CA | 2 | −0.01 | 0.613 | −0.555 |
| 132 | 6652 | SORD | 2 | −0.42 | 0.644 | −0.236 |
| 133 | 6695 | SPOCK1 | 2 | −0.43 | 0.959 | −0.512 |
| 134 | 7113 | TMPRSS2 | 2 | −0.35 | 0.626 | −0.278 |
| 135 | 7941 | PLA2G7 | 2 | −0.27 | 1.198 | −0.872 |
| 136 | 8671 | SLC4A4 | 2 | −0.37 | 0.704 | −0.328 |
| 137 | 9073 | CLDN8 | 2 | −0.17 | 0.826 | −0.617 |
| 138 | 10269 | ZMPSTE24 | 2 | −0.05 | 0.611 | −0.521 |
| 139 | 10321 | CRISP3 | 2 | −0.16 | 1.018 | −0.802 |
| 140 | 10611 | PDLIM5 | 2 | 0.137 | 0.592 | −0.661 |
| 141 | 10788 | IQGAP2 | 2 | −0.32 | 0.907 | −0.565 |
| 142 | 10954 | PDIA5 | 2 | −0.09 | 0.582 | −0.46 |
| 143 | 23316 | CUX2 | 2 | −0.43 | 0.605 | −0.185 |
| 144 | 23327 | NEDD4L | 2 | −0.06 | 0.646 | −0.541 |
| 145 | 25800 | SLC39A6 | 2 | −0.06 | 0.629 | −0.524 |
| 146 | 51109 | RDH11 | 2 | −0.38 | 0.588 | −0.212 |
| 147 | 51313 | FAM198B | 2 | −0.17 | 0.591 | −0.399 |
| 148 | 51365 | PLA1A | 2 | −0.13 | 0.826 | −0.652 |
| 149 | 57600 | FNIP2 | 2 | −0.12 | 0.742 | −0.578 |
| 150 | 58511 | DNASE2B | 2 | −0.07 | 0.682 | −0.568 |
| 151 | 59084 | ENPP5 | 2 | −0.27 | 0.585 | −0.304 |
| 152 | 60481 | ELOVL5 | 2 | −0.12 | 0.621 | −0.47 |
| 153 | 79054 | TRPM8 | 2 | −0.52 | 0.886 | −0.372 |
| 154 | 79689 | STEAP4 | 2 | −0.26 | 0.78 | −0.493 |
| 155 | 116285 | ACSM1 | 2 | 0.164 | 0.723 | −0.806 |
| 156 | 130733 | TMEM178A | 2 | −0.69 | 0.848 | −0.19 |
| 157 | 143503 | OR51E1 | 2 | −0.12 | 0.641 | −0.483 |
| 158 | 148327 | CREB3L4 | 2 | −0.19 | 0.621 | −0.412 |
| 159 | 151258 | SLC38A11 | 2 | −0.19 | 0.589 | −0.378 |
| 160 | 9185 | REPS2 | 2 | −0.05 | 0.647 | −0.549 |
| 161 | 2203 | FBP1 | 2 | −0.37 | 0.713 | −0.34 |
| 162 | 7782 | SLC30A4 | 2 | −0.49 | 0.678 | −0.201 |
| 163 | 10481 | HOXB13 | 2 | −0.04 | 0.611 | −0.531 |
| 164 | 11001 | SLC27A2 | 2 | 0.078 | 0.581 | −0.602 |
| 165 | 57535 | KIAA1324 | 2 | −0.6 | 0.837 | −0.258 |
| 166 | 120224 | TMEM45B | 2 | 0.173 | 0.677 | −0.772 |
| 167 | 306 | ANXA3 | 2 | −0.91 | 0.918 | −0.061 |
| 168 | 957 | ENTPD5 | 2 | −0.15 | 0.696 | −0.509 |
| 169 | 2346 | FOLH1 | 2 | 0.03 | 0.926 | −0.877 |
| 170 | 3081 | HGD | 2 | −0.57 | 0.717 | −0.175 |
| 171 | 4744 | NEFH | 2 | −1.38 | 0.58 | 0.646 |
| 172 | 4852 | NPY | 2 | −1.12 | 1.599 | −0.513 |
| 173 | 5320 | PLA2G2A | 2 | −0.88 | 0.833 | −0.012 |
| 174 | 5874 | RAB27B | 2 | −0.4 | 0.595 | −0.206 |
| 175 | 6296 | ACSM3 | 2 | 2E−04 | 0.653 | −0.601 |
| 176 | 6558 | SLC12A2 | 2 | −0.41 | 0.74 | −0.326 |
| 177 | 6646 | SOAT1 | 2 | −0.13 | 0.602 | −0.445 |
| 178 | 7103 | TSPAN8 | 2 | −0.43 | 0.63 | −0.214 |
| 179 | 9375 | TM9SF2 | 2 | −0.25 | 0.587 | −0.328 |
| 180 | 9413 | FAM189A2 | 2 | −0.52 | 0.58 | −0.089 |
| 181 | 10103 | TSPAN1 | 2 | −0.42 | 0.716 | −0.302 |
| 182 | 11013 | TMSB15A | 2 | −0.04 | 0.851 | −0.753 |
| 183 | 23600 | AMACR | 2 | 0.188 | 1.177 | −1.244 |
| 184 | 25874 | MPC2 | 2 | 0.115 | 0.594 | −0.645 |
| 185 | 26503 | SLC17A5 | 2 | −0.08 | 0.591 | −0.475 |
| 186 | 26872 | STEAP1 | 2 | 0.065 | 0.6 | −0.608 |
| 187 | 26996 | GPR160 | 2 | 0.169 | 0.821 | −0.9 |
| 188 | 27249 | MMADHC | 2 | −0.31 | 0.662 | −0.343 |
| 189 | 51084 | CRYL1 | 2 | −0.32 | 0.619 | −0.298 |
| 190 | 51170 | HSD17B11 | 2 | −0.06 | 0.601 | −0.506 |
| 191 | 51280 | GOLM1 | 2 | −0.31 | 0.914 | −0.574 |
| 192 | 51302 | CYP39A1 | 2 | −0.29 | 0.624 | −0.323 |
| 193 | 51635 | DHRS7 | 2 | −0.37 | 0.742 | −0.364 |
| 194 | 51809 | GALNT7 | 2 | −0.11 | 0.78 | −0.623 |
| 195 | 54431 | DNAJC10 | 2 | −0.14 | 0.767 | −0.59 |

TABLE 6-continued

List of 428 SEGs.

| FIG. 4A Order | Entrez Gene ID | Symbol | Sub-type ID | Fold change in PCS1 | Fold change in PCS2 | Fold change in PCS3 |
|---|---|---|---|---|---|---|
| 196 | 54502 | RBM47 | 2 | −0.21 | 0.585 | −0.359 |
| 197 | 55790 | CSGALNACT1 | 2 | −0.58 | 0.877 | −0.313 |
| 198 | 56165 | TDRD1 | 2 | −0.4 | 1.094 | −0.661 |
| 199 | 64094 | SMOC2 | 2 | −0.5 | 0.621 | −0.147 |
| 200 | 80110 | ZNF614 | 2 | −0.05 | 0.607 | −0.517 |
| 201 | 80157 | CWH43 | 2 | −0.35 | 0.614 | −0.261 |
| 202 | 81285 | OR51E2 | 2 | −0.51 | 1.197 | −0.661 |
| 203 | 84419 | C15orf48 | 2 | −0.46 | 0.607 | −0.166 |
| 204 | 84899 | TMTC4 | 2 | −0.08 | 0.66 | −0.54 |
| 205 | 90701 | SEC11C | 2 | −0.29 | 0.742 | −0.437 |
| 206 | 92292 | GLYATL1 | 2 | −0.06 | 0.704 | −0.595 |
| 207 | 131034 | CPNE4 | 2 | −0.29 | 0.788 | −0.477 |
| 208 | 219595 | FOLH1B | 2 | 0.156 | 0.635 | −0.718 |
| 209 | 284119 | ZNF615 | 2 | −0.09 | 0.586 | −0.464 |
| 210 | 70 | ACTC1 | 3 | −1.02 | −0.15 | 1.011 |
| 211 | 72 | ACTG2 | 3 | −1.77 | 0.32 | 1.218 |
| 212 | 477 | ATP1A2 | 3 | −0.87 | −0.17 | 0.899 |
| 213 | 5919 | RARRES2 | 3 | −0.66 | −0.29 | 0.839 |
| 214 | 2919 | CXCL1 | 3 | −0.46 | −0.24 | 0.612 |
| 215 | 5239 | PGM5 | 3 | −1.25 | −0.01 | 1.08 |
| 216 | 6876 | TAGLN | 3 | −0.95 | −0.05 | 0.856 |
| 217 | 7881 | KCNAB1 | 3 | −0.51 | −0.17 | 0.591 |
| 218 | 10418 | SPON1 | 3 | −0.55 | −0.21 | 0.662 |
| 219 | 284 | ANGPT1 | 3 | −0.69 | −0.17 | 0.75 |
| 220 | 1674 | DES | 3 | −1.32 | −0.07 | 1.193 |
| 221 | 1805 | DPT | 3 | −0.62 | −0.27 | 0.779 |
| 222 | 2354 | FOSB | 3 | −1.03 | 0.277 | 0.629 |
| 223 | 2568 | GABRP | 3 | −0.39 | −0.28 | 0.595 |
| 224 | 4638 | MYLK | 3 | −1.44 | 0.28 | 0.973 |
| 225 | 4660 | PPP1R12B | 3 | −0.76 | 0.013 | 0.637 |
| 226 | 4681 | NBL1 | 3 | −0.58 | −0.19 | 0.667 |
| 227 | 4921 | DDR2 | 3 | −0.62 | −0.06 | 0.581 |
| 228 | 5918 | RARRES1 | 3 | −0.67 | −0.18 | 0.738 |
| 229 | 5947 | RBP1 | 3 | −0.28 | −0.37 | 0.581 |
| 230 | 7047 | TGM4 | 3 | −0.71 | −0.12 | 0.719 |
| 231 | 7169 | TPM2 | 3 | −1.14 | −0.15 | 1.114 |
| 232 | 9510 | ADAMTS1 | 3 | −0.57 | −0.17 | 0.651 |
| 233 | 10563 | CXCL13 | 3 | −0.22 | −0.52 | 0.66 |
| 234 | 3371 | TNC | 3 | −0.58 | −0.12 | 0.606 |
| 235 | 4684 | NCAM1 | 3 | −0.27 | −0.42 | 0.619 |
| 236 | 59 | ACTA2 | 3 | −1.07 | 0.044 | 0.877 |
| 237 | 290 | ANPEP | 3 | −0.86 | 0.065 | 0.678 |
| 238 | 467 | ATF3 | 3 | −0.81 | 0.106 | 0.6 |
| 239 | 1288 | COL4A6 | 3 | −0.68 | −0.23 | 0.791 |
| 240 | 1410 | CRYAB | 3 | −0.72 | −0.39 | 0.983 |
| 241 | 2294 | FOXF1 | 3 | −0.64 | −0.19 | 0.722 |
| 242 | 2316 | FLNA | 3 | −0.8 | −0.06 | 0.739 |
| 243 | 2920 | CXCL2 | 3 | −0.46 | −0.24 | 0.611 |
| 244 | 3678 | ITGA5 | 3 | −0.51 | −0.28 | 0.695 |
| 245 | 3679 | ITGA7 | 3 | −0.58 | −0.18 | 0.655 |
| 246 | 3872 | KRT17 | 3 | −0.59 | −0.22 | 0.71 |
| 247 | 4118 | MAL | 3 | −0.3 | −0.4 | 0.63 |
| 248 | 4629 | MYH11 | 3 | −1.55 | 0.135 | 1.203 |
| 249 | 5179 | PENK | 3 | −0.42 | −0.41 | 0.73 |
| 250 | 5268 | SERPINB5 | 3 | −0.5 | −0.19 | 0.597 |
| 251 | 5376 | PMP22 | 3 | −0.58 | −0.23 | 0.712 |
| 252 | 5730 | PTGDS | 3 | −1.01 | −0.03 | 0.89 |
| 253 | 6277 | S100A6 | 3 | −0.63 | −0.22 | 0.746 |
| 254 | 6387 | CXCL12 | 3 | −0.46 | −0.21 | 0.587 |
| 255 | 6525 | SMTN | 3 | −0.73 | −0.21 | 0.818 |
| 256 | 6716 | SRD5A2 | 3 | −1.02 | 0.009 | 0.864 |
| 257 | 7168 | TPM1 | 3 | −0.88 | 0.135 | 0.631 |
| 258 | 7538 | ZFP36 | 3 | −1.11 | 0.393 | 0.592 |
| 259 | 8013 | NR4A3 | 3 | −0.65 | −0.03 | 0.586 |
| 260 | 8406 | SRPX | 3 | −0.57 | −0.14 | 0.621 |
| 261 | 8854 | ALDH1A2 | 3 | −0.78 | −0.03 | 0.696 |
| 262 | 8870 | IER3 | 3 | −0.53 | −0.24 | 0.668 |
| 263 | 9021 | SOCS3 | 3 | −0.77 | −0.02 | 0.672 |
| 264 | 9260 | PDLIM7 | 3 | −0.49 | −0.25 | 0.645 |
| 265 | 9506 | PAGE4 | 3 | −1.39 | 0.087 | 1.109 |
| 266 | 10398 | MYL9 | 3 | −1.13 | −0.16 | 1.117 |
| 267 | 10580 | SORBS1 | 3 | −0.98 | 0.011 | 0.831 |
| 268 | 22943 | DKK1 | 3 | −0.37 | −0.3 | 0.592 |
| 269 | 25802 | LMOD1 | 3 | −1.04 | −0.13 | 1.011 |
| 270 | 30008 | EFEMP2 | 3 | −0.36 | −0.32 | 0.609 |
| 271 | 50859 | SPOCK3 | 3 | −0.86 | −0.06 | 0.789 |
| 272 | 53826 | FXYD6 | 3 | −0.55 | −0.32 | 0.764 |
| 273 | 64093 | SMOC1 | 3 | −0.45 | −0.22 | 0.589 |
| 274 | 284119 | PTRF | 3 | −0.8 | −0.08 | 0.754 |
| 275 | 316 | AOX1 | 3 | −0.74 | −0.12 | 0.747 |
| 276 | 390 | RND3 | 3 | −0.8 | −0.05 | 0.735 |
| 277 | 443 | ASPA | 3 | −0.45 | −0.26 | 0.618 |
| 278 | 493 | ATP2B4 | 3 | −0.56 | −0.14 | 0.607 |
| 279 | 629 | CFB | 3 | −0.64 | −0.05 | 0.593 |
| 280 | 653 | BMP5 | 3 | −0.29 | −0.36 | 0.583 |
| 281 | 710 | SERPING1 | 3 | −0.68 | −0.18 | 0.75 |
| 282 | 716 | C1S | 3 | −0.81 | −0.03 | 0.723 |
| 283 | 857 | CAV1 | 3 | −0.93 | −0.08 | 0.872 |
| 284 | 858 | CAV2 | 3 | −0.52 | −0.16 | 0.595 |
| 285 | 894 | CCND2 | 3 | −0.51 | −0.16 | 0.583 |
| 286 | 1066 | CES1 | 3 | −0.71 | −0.19 | 0.788 |
| 287 | 1191 | CLU | 3 | −0.7 | −0.31 | 0.891 |
| 288 | 1264 | CNN1 | 3 | −1.54 | 0.019 | 1.302 |
| 289 | 1291 | COL6A1 | 3 | −0.4 | −0.41 | 0.719 |
| 290 | 1292 | COL6A2 | 3 | −0.53 | −0.24 | 0.677 |
| 291 | 1307 | COL16A1 | 3 | −0.51 | −0.29 | 0.708 |
| 292 | 1346 | COX7A1 | 3 | −0.8 | −0.23 | 0.904 |
| 293 | 1465 | CSRP1 | 3 | −1.1 | 0.122 | 0.832 |
| 294 | 1577 | CYP3A5 | 3 | −0.58 | −0.23 | 0.711 |
| 295 | 1580 | CYP4B1 | 3 | −0.4 | −0.27 | 0.591 |
| 296 | 1593 | CYP27A1 | 3 | −0.57 | −0.21 | 0.682 |
| 297 | 1672 | DEFB1 | 3 | −0.4 | −0.29 | 0.612 |
| 298 | 1675 | CFD | 3 | −0.58 | −0.31 | 0.777 |
| 299 | 1809 | DPYSL3 | 3 | −0.7 | −0.07 | 0.665 |
| 300 | 2192 | FBLN1 | 3 | −1.13 | 0.033 | 0.934 |
| 301 | 2202 | EFEMP1 | 3 | −0.54 | −0.2 | 0.647 |
| 302 | 2263 | FGFR2 | 3 | −0.67 | −0.09 | 0.655 |
| 303 | 2273 | FHL1 | 3 | −1.11 | −0.01 | 0.962 |
| 304 | 2274 | FHL2 | 3 | −0.84 | −0.03 | 0.745 |
| 305 | 2318 | FLNC | 3 | −0.75 | −0.29 | 0.911 |
| 306 | 2564 | GABRE | 3 | −0.72 | −0.18 | 0.776 |
| 307 | 2619 | GAS1 | 3 | −0.72 | −0.11 | 0.716 |
| 308 | 2934 | GSN | 3 | −0.82 | −0.02 | 0.725 |
| 309 | 2944 | GSTM1 | 3 | −0.57 | −0.23 | 0.696 |
| 310 | 2946 | GSTM2 | 3 | −0.7 | −0.25 | 0.828 |
| 311 | 2949 | GSTM5 | 3 | −0.61 | −0.2 | 0.708 |
| 312 | 2950 | GSTP1 | 3 | −0.81 | −0.31 | 0.979 |
| 313 | 3397 | ID1 | 3 | −0.75 | −0.15 | 0.779 |
| 314 | 3399 | ID3 | 3 | −0.55 | −0.16 | 0.622 |
| 315 | 3489 | IGFBP6 | 3 | −0.75 | −0.27 | 0.891 |
| 316 | 3491 | CYR61 | 3 | −1.01 | 0.247 | 0.635 |
| 317 | 3569 | IL6 | 3 | −0.39 | −0.33 | 0.64 |
| 318 | 3764 | KCNJ8 | 3 | −0.37 | −0.3 | 0.585 |
| 319 | 3779 | KCNMB1 | 3 | −0.95 | −0.25 | 1.044 |
| 320 | 3852 | KRT5 | 3 | −0.95 | −0.18 | 0.987 |
| 321 | 3860 | KRT13 | 3 | −0.61 | −0.19 | 0.701 |
| 322 | 3866 | KRT15 | 3 | −1.1 | −0.08 | 1.022 |
| 323 | 3910 | LAMA4 | 3 | −0.37 | −0.33 | 0.623 |
| 324 | 3914 | LAMB3 | 3 | −0.59 | −0.23 | 0.719 |
| 325 | 3934 | LCN2 | 3 | −0.71 | −0.19 | 0.781 |
| 326 | 3956 | LGALS1 | 3 | −0.64 | −0.23 | 0.762 |
| 327 | 4057 | LTF | 3 | −1.1 | 0.124 | 0.828 |
| 328 | 4129 | MAOB | 3 | −0.94 | 0.026 | 0.783 |
| 329 | 4147 | MATN2 | 3 | −0.74 | 0.051 | 0.583 |
| 330 | 4211 | MEIS1 | 3 | −0.71 | −0.05 | 0.651 |
| 331 | 4212 | MEIS2 | 3 | −0.83 | −0.03 | 0.732 |
| 332 | 4239 | MFAP4 | 3 | −0.7 | −0.19 | 0.775 |
| 333 | 4920 | ROR2 | 3 | −0.49 | −0.18 | 0.589 |
| 334 | 4969 | OGN | 3 | −0.86 | 0.074 | 0.667 |
| 335 | 5099 | PCDH7 | 3 | −0.52 | −0.17 | 0.601 |
| 336 | 5121 | PCP4 | 3 | −1.57 | 0.231 | 1.133 |
| 337 | 5176 | SERPINF1 | 3 | −0.64 | −0.26 | 0.785 |
| 338 | 5348 | FXYD1 | 3 | −0.53 | −0.32 | 0.75 |
| 339 | 5350 | PLN | 3 | −0.85 | 0.008 | 0.721 |
| 340 | 5579 | PRKCB | 3 | −0.39 | −0.3 | 0.606 |
| 341 | 5648 | MASP1 | 3 | −0.44 | −0.22 | 0.586 |

TABLE 6-continued

List of 428 SEGs.

| FIG. 4A Order | Entrez Gene ID | Symbol | Sub-type ID | Fold change in PCS1 | Fold change in PCS2 | Fold change in PCS3 |
|---|---|---|---|---|---|---|
| 342 | 5764 | PTN | 3 | −0.98 | 0.065 | 0.779 |
| 343 | 5837 | PYGM | 3 | −0.52 | −0.16 | 0.591 |
| 344 | 6273 | S100A2 | 3 | −0.54 | −0.14 | 0.599 |
| 345 | 6275 | S100A4 | 3 | −0.42 | −0.39 | 0.726 |
| 346 | 6347 | CCL2 | 3 | −0.78 | 0.006 | 0.663 |
| 347 | 6376 | CX3CL1 | 3 | −0.68 | −0.21 | 0.78 |
| 348 | 6401 | SELE | 3 | −0.8 | 0.056 | 0.635 |
| 349 | 6442 | SGCA | 3 | −0.41 | −0.26 | 0.59 |
| 350 | 6518 | SLC2A5 | 3 | −0.51 | −0.22 | 0.638 |
| 351 | 6563 | SLC14A1 | 3 | −0.79 | −0.06 | 0.739 |
| 352 | 6604 | SMARCD3 | 3 | −0.36 | −0.32 | 0.607 |
| 353 | 6769 | STAC | 3 | −0.47 | −0.21 | 0.596 |
| 354 | 6840 | SVIL | 3 | −0.67 | −0.03 | 0.595 |
| 355 | 7041 | TGFB1I1 | 3 | −0.52 | −0.25 | 0.667 |
| 356 | 7043 | TGFB3 | 3 | −0.57 | −0.29 | 0.759 |
| 357 | 7077 | TIMP2 | 3 | −0.44 | −0.26 | 0.614 |
| 358 | 7123 | CLEC3B | 3 | −0.34 | −0.36 | 0.618 |
| 359 | 7145 | TNS1 | 3 | −0.85 | −0.09 | 0.809 |
| 360 | 7205 | TRIP6 | 3 | −0.47 | −0.24 | 0.62 |
| 361 | 7356 | SCGB1A1 | 3 | −0.46 | −0.33 | 0.693 |
| 362 | 7414 | VCL | 3 | −0.6 | −0.11 | 0.619 |
| 363 | 7732 | RNF112 | 3 | −0.37 | −0.28 | 0.582 |
| 364 | 8309 | ACOX2 | 3 | −0.51 | −0.21 | 0.631 |
| 365 | 8404 | SPARCL1 | 3 | −1.2 | 0.169 | 0.874 |
| 366 | 8425 | LTBP4 | 3 | −0.53 | −0.15 | 0.596 |
| 367 | 8613 | PPAP2B | 3 | −0.67 | −0.04 | 0.612 |
| 368 | 8626 | TP63 | 3 | −1.07 | 0.025 | 0.896 |
| 369 | 8639 | AOC3 | 3 | −0.72 | −0.14 | 0.74 |
| 370 | 8654 | PDE5A | 3 | −0.88 | 0.092 | 0.67 |
| 371 | 9843 | HEPH | 3 | −0.45 | −0.27 | 0.638 |
| 372 | 10231 | RCAN2 | 3 | −0.64 | −0.22 | 0.749 |
| 373 | 10278 | EFS | 3 | −0.5 | −0.23 | 0.636 |
| 374 | 10290 | SPEG | 3 | −0.54 | −0.24 | 0.685 |
| 375 | 10335 | MRVI1 | 3 | −0.66 | −0.16 | 0.709 |
| 376 | 10406 | WFDC2 | 3 | −0.64 | −0.23 | 0.76 |
| 377 | 10562 | OLFM4 | 3 | −1.1 | 0.132 | 0.823 |
| 378 | 10826 | FAXDC2 | 3 | −0.48 | −0.23 | 0.623 |
| 379 | 10974 | ADIRF | 3 | −1.01 | 0.115 | 0.758 |
| 380 | 11030 | RBPMS | 3 | −0.63 | −0.17 | 0.701 |
| 381 | 11117 | EMILIN1 | 3 | −0.41 | −0.27 | 0.601 |
| 382 | 11155 | LDB3 | 3 | −0.53 | −0.22 | 0.656 |
| 383 | 11170 | FAM107A | 3 | −0.87 | −0.13 | 0.867 |
| 384 | 11259 | FILIP1L | 3 | −0.6 | −0.18 | 0.685 |
| 385 | 11341 | SCRG1 | 3 | −0.48 | −0.35 | 0.731 |
| 386 | 23022 | PALLD | 3 | −0.75 | −0.03 | 0.674 |
| 387 | 23336 | SYNM | 3 | −1.45 | 0.191 | 1.067 |
| 388 | 23584 | VSIG2 | 3 | −0.6 | −0.14 | 0.642 |
| 389 | 23650 | TRIM29 | 3 | −0.82 | −0.18 | 0.871 |
| 390 | 25959 | KANK2 | 3 | −0.56 | −0.14 | 0.61 |
| 391 | 25984 | KRT23 | 3 | −0.76 | −0.14 | 0.778 |
| 392 | 25999 | CLIP3 | 3 | −0.39 | −0.41 | 0.71 |
| 393 | 26353 | HSPB8 | 3 | −0.91 | −0.17 | 0.933 |
| 394 | 26577 | PCOLCE2 | 3 | −0.73 | −0.11 | 0.728 |
| 395 | 27122 | DKK3 | 3 | −0.7 | −0.09 | 0.684 |
| 396 | 27129 | HSPB7 | 3 | −0.36 | −0.32 | 0.598 |
| 397 | 29951 | PDZRN4 | 3 | −0.83 | −0.01 | 0.714 |
| 398 | 51285 | RASL12 | 3 | −0.57 | −0.31 | 0.769 |
| 399 | 51676 | ASB2 | 3 | −0.56 | −0.16 | 0.632 |
| 400 | 55679 | LIMS2 | 3 | −0.54 | −0.26 | 0.703 |
| 401 | 58189 | WFDC1 | 3 | −0.86 | −0.28 | 0.996 |
| 402 | 59353 | TMEM35 | 3 | −0.73 | −0.05 | 0.676 |
| 403 | 64091 | POPDC2 | 3 | −0.59 | −0.13 | 0.627 |
| 404 | 79625 | NDNF | 3 | −0.49 | −0.23 | 0.634 |
| 405 | 79630 | C1orf54 | 3 | −0.42 | −0.26 | 0.597 |
| 406 | 80206 | FHOD3 | 3 | −0.5 | −0.22 | 0.635 |
| 407 | 83643 | CCDC3 | 3 | −0.34 | −0.31 | 0.583 |
| 408 | 83716 | CRISPLD2 | 3 | −0.7 | −0.02 | 0.621 |
| 409 | 84417 | C2orf40 | 3 | −0.7 | −0.25 | 0.823 |
| 410 | 84617 | TUBB6 | 3 | −0.57 | −0.19 | 0.667 |
| 411 | 89927 | C16orf45 | 3 | −0.46 | −0.23 | 0.604 |
| 412 | 91624 | NEXN | 3 | −0.89 | −0.06 | 0.815 |
| 413 | 91851 | CHRDL1 | 3 | −0.99 | −0.05 | 0.896 |
| 414 | 93649 | MYOCD | 3 | −0.61 | −0.13 | 0.64 |
| 415 | 94274 | PPP1R14A | 3 | −0.46 | −0.32 | 0.688 |
| 416 | 112464 | PRKCDBP | 3 | −0.49 | −0.26 | 0.655 |
| 417 | 113146 | AHNAK2 | 3 | −0.49 | −0.31 | 0.709 |
| 418 | 116535 | MRGPRF | 3 | −0.64 | −0.13 | 0.67 |
| 419 | 118425 | PCAT4 | 3 | −0.84 | 0.126 | 0.604 |
| 420 | 126393 | HSPB6 | 3 | −0.51 | −0.29 | 0.704 |
| 421 | 140597 | TCEAL2 | 3 | −0.82 | −0.13 | 0.83 |
| 422 | 146713 | RBFOX3 | 3 | −0.6 | −0.1 | 0.611 |
| 423 | 147906 | DACT3 | 3 | −0.52 | −0.16 | 0.591 |
| 424 | 148741 | ANKRD35 | 3 | −0.57 | −0.2 | 0.676 |
| 425 | 171024 | SYNPO2 | 3 | −1.27 | 0.266 | 0.842 |
| 426 | 253827 | MSRB3 | 3 | −0.64 | −0.08 | 0.625 |
| 427 | 387763 | C11orf96 | 3 | −0.48 | −0.27 | 0.661 |
| 428 | 728264 | MIR143HG | 3 | −0.67 | −0.1 | 0.673 |

Figure 4E:
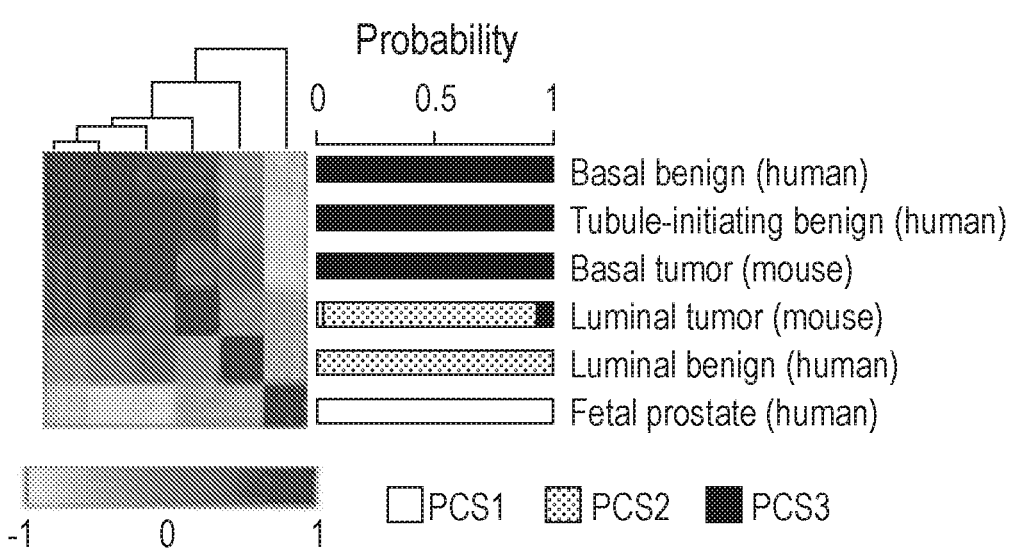

To determine whether the PCS categories reflect luminal or basal cell types of the prostatic epithelium, we analyzed the mean expression of genes known to be characteristic of luminal (EZH2, AR, MKI67, NKX3-1, KLK2/3, and ERG) or basal (ACTA2, GSTP1, IL6, KRT5, and TP63) prostatic cells (FIG. 4C). We observed a strong association (FDR<0.001; fold change>1.5) between luminal genes and PCS1 and PCS2, and basal genes and PCS3. To verify this observation, we used two independent datasets derived from luminal and basal cells from human (Liu H, Cadaneanu R M, Lai K, Zhang B, Huo L, An D S, et al. Differential gene expression profiling of functionally and developmentally distinct human prostate epithelial populations. Prostate 2015; 75:764-76) and mouse (GSE39509; Wang Z A, Mitrofanova A, Bergren S K, Abate-Shen C, Cardiff R D, Califano A, et al. Lineage analysis of basal epithelial cells reveals their unexpected plasticity and supports a cell-of-origin model for prostate cancer heterogeneity. Nat Cell Biol 2013; 15:274-83 prostates. The assignment of a basal designation to PCS3 is further supported by the highly significant enrichment in PCS3, in comparison with the other two subtypes, of a recently described prostate basal cell signature derived from CD49f-Hi versus CD49f-Lo benign and malignant prostate epithelial cells (FIG. 4D; Smith B A, Sokolov A, Uzunangelov V, Baertsch R, Newton Y, Graim K, et al. A basal stem cell signature identifies aggressive prostate cancer phenotypes. Proc Natl Acad Sci USA 2015; 112: E6544-52). In addition, using the 14-pathway classifier, mouse basal tumors and human basal cells from benign tissues were classified as PCS3, while mouse luminal tumors and benign prostate human luminal cells were classified into PCS2 (FIG. 4E). These results are consistent with the conclusion that the PCS categories can be divided into luminal and basal subtypes.

A Gene Expression Classifier for Assignment to Subtypes

Figure 5A:
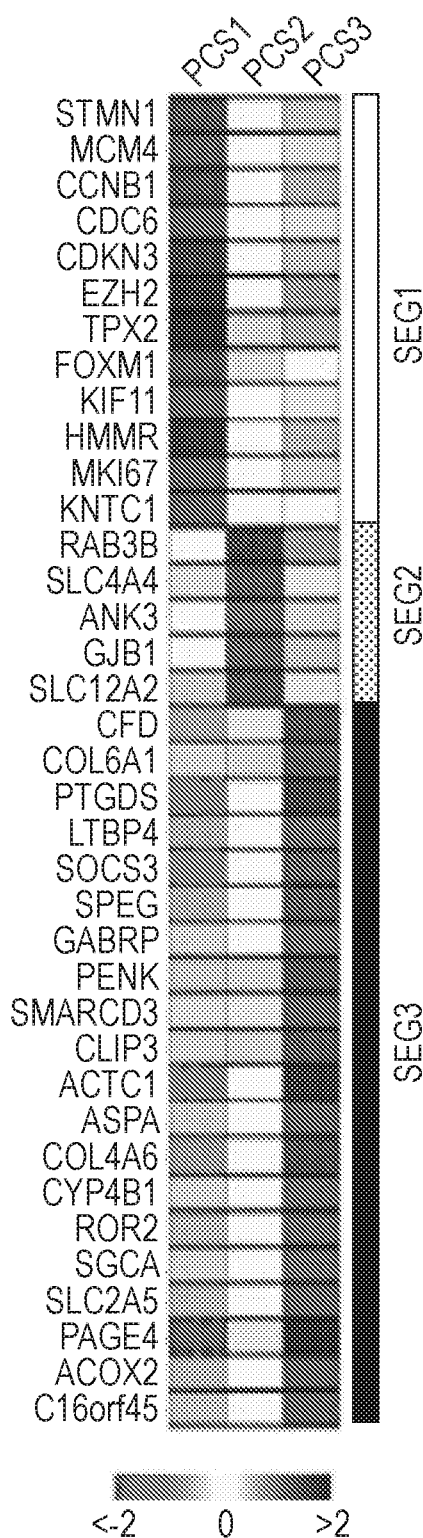
FIG. 5A-FIG. 5D illustrates, in accordance with various embodiments of the present invention, a 37-gene classifier employed in patient tissues and CTCs.
Figure 5B:
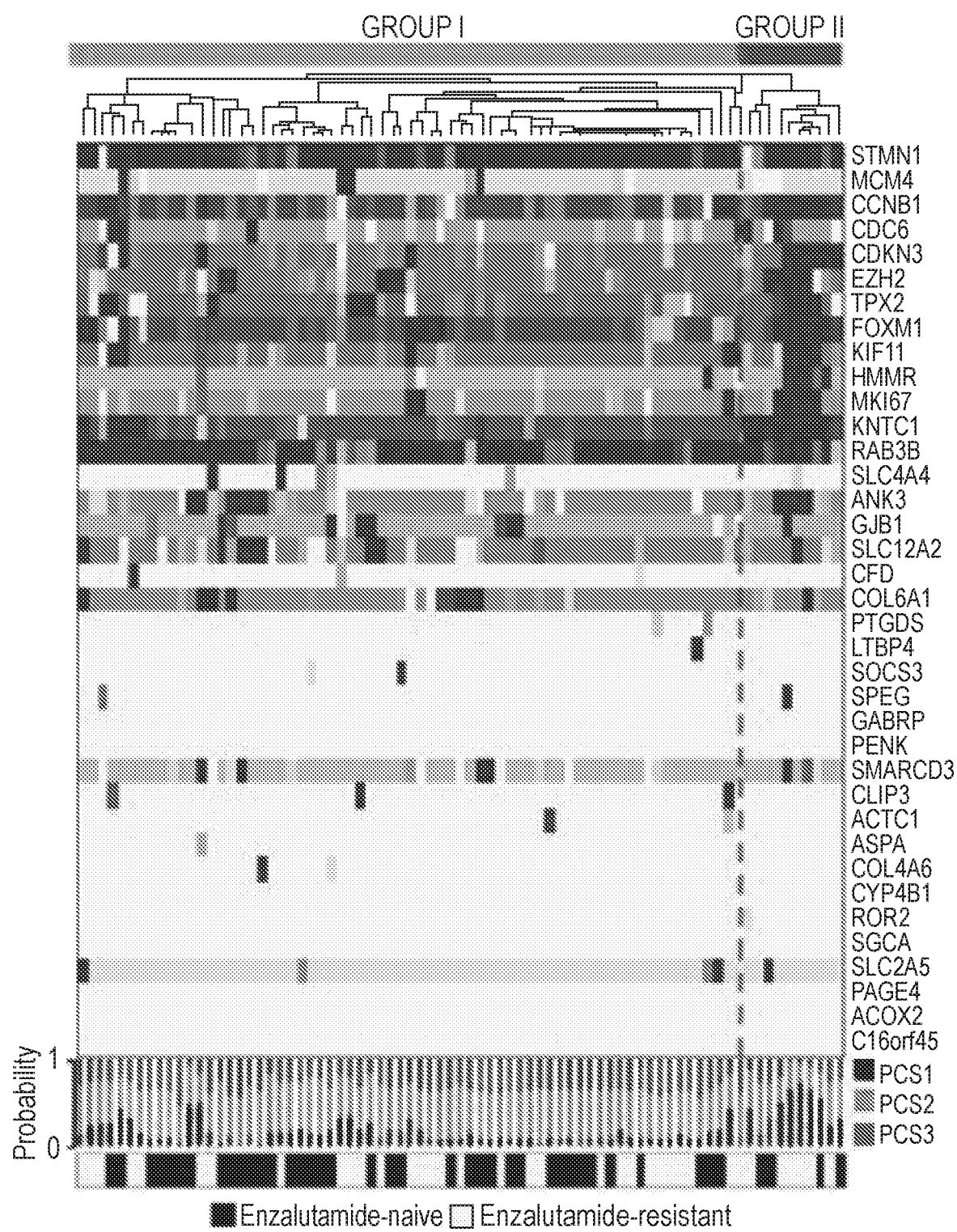
Figure 5C:
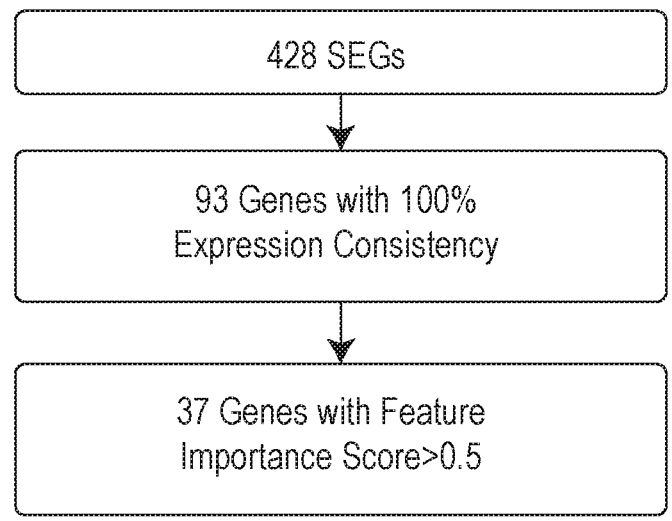
Figure 5D:
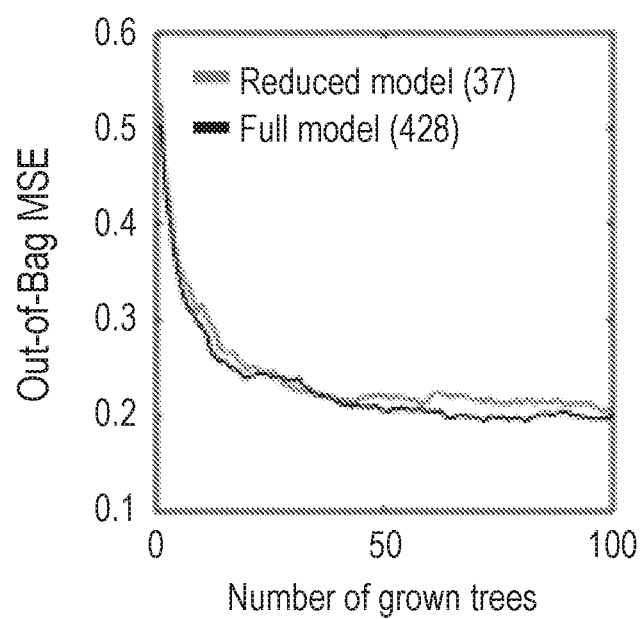

Given the potential advantages of the PCS system to classify tumor specimens, we constructed a classifier that can be applied to an individual patient specimen in a clinical setting (FIG. 5C). First, of 428 SEGs, 93 genes were selected on the basis of highly consistent expression patterns in 10 cohorts (i.e., SWD, TCGA, EMORY, HSPT, SU2C, MAYO1/2, CCF, TJU, and JHM). Second, using a random forest machine learning algorithm, we selected 37 genes with feature importance scores>0.5, showing a comparable level of error with the full model based on 428 SEGs (FIG. 5D). Performance of the classifier was assessed in the GRID cohort (AUC ¼ 0.97). The 37-gene panel displays significantly different expression patterns between the three subtypes in the DISC cohort (FIG. 5A).

The robust performance of the gene panel led us to determine whether it could be used to profile circulating tumor cells (CTC) from patients with CRPC. We analyzed single-cell RNA-seq data from 77 intact CTCs isolated from 13 patients (Miyamoto D T, Zheng Y, Wittner B S, Lee R J, Zhu H, Broderick K T, et al. RNA-Seq of single prostate CTCs implicates noncanonical Wnt signaling in antiandrogen resistance. Science 2015; 349:1351-6). Prior to the clustering analysis to investigate the expression patterns of these CTC data, the normalized read counts as read-per-million (RPM) mapped reads were transformed on a log 2 scale for each gene. The 77 CTCs were largely clustered into two groups using median-centered expression profiles corresponding to the 37-gene PCS panel by the hierarchical method (FIG. 5B). One group (GROUP I), consisting of 67 CTCs displays low expression of PCS1-enriched genes, while the other group (GROUP II) consisting of 10 CTCs has high expression of PCS1-enriched genes. In addition, we observed that PCS3-enriched genes in the panel were not detected or have very low expression changes across all CTCs as shown in the heatmap of FIG. 5B. The results suggest that CTCs can be divided into two groups with the 37-gene PCS panel. Given this result, we hypothesized that the 37-gene classifier might assign CTCs to PCS1 or PCS2, consistent with the clustering result. The bar graph below the heatmap illustrates the probability of likelihood of PCS assignment, with the result that all the CTCs were assigned to PCS1 (n=12) or PCS2 (n=65), while no PCS3 CTCs were assigned on the basis of the largest probability score. By comparing with the CTC group assignment, 7 (70%) of 10 CTCs in the GROUP II were assigned to PCS1 by the 37-gene classifier and 62 (95%) of 65 CTCs in the GROUP I were assigned to PCS2 by the classifier. We then tested whether GROUP I and II exhibit any difference in terms of therapeutic responses. Of note, 5 of the 7 CTCs in GROUP II (OR: 1.74; 95% confidence interval: 0.49-6.06) were from patients whose cancer exhibited radiographic and/or PSA progression during enzalutamide therapy, suggesting that the 37-gene PCS panel can potentially identify patients with resistance to enzalutamide therapy.

Collectively, the results demonstrate that the 37-gene classifier has a potential to assign individual prostate cancers to PCS1 using both prostate tissues and blood CTCs, suggesting that the classifier can be applied to subtype individual prostate cancers using clinically relevant technology platforms (Geiss G K, Bumgarner R E, Birditt B, Dahl T, Dowidar N, Dunaway D L, et al. Direct multiplexed measurement of gene expression with color-coded probe pairs. Nat Biotechnol 2008; 26:317-25; Morrison T, Hurley J, Garcia J, Yoder K, Katz A, Roberts D, et al. Nanoliter high throughput quantitative PCR. Nucleic Acids Res 2006; 34:e123), including by noninvasive methods.

Herein, the inventors describe a novel classification system for prostate cancer, based on an analysis of over 4,600 prostate cancer specimens, which consists of only 3 distinct subtypes, designated PCS1, PCS2, and PCS3. PCS1 exhibits the highest risk of progression to advanced disease, even for low Gleason grade tumors. Although sampling methods across the cohorts we studied were different, classification into the 3 subtypes was reproducible. For example, the SWD cohort consists of specimens that were obtained by transurethral resection of the prostate rather than radical prostatectomy; however, subtype assignment and prognostic differences between the subtypes were similar to the other cohorts we examined (FIG. 3H(x)). Genes that are significantly enriched in the PCS1 category were highly expressed in the subset of CTCs (58%, 7 CTCs out of 12) from patients with enzalutamide-resistant tumors. This proportion of resistant cases in PCS1 CTCs is very high compared with PCS2 CTCs (8%, 5 CTCs out of 65). The characteristics of the PCS categories are summarized in Table 7.

TABLE 7

Summary of PCS characteristics

| Sample Type | Features | PCS1 | PCS2 | PCS3 |
|---|---|---|---|---|
| Patient Tumors | Proportion | 6% | 47% | 47% |
| | Pathology | Enriched GS ≥8 | Enriched GS ≤7 | Enriched GS ≤7 |
| | Prognosis | Poor | Variable | Variable |
| | Subtypes - TCGA | SPOP | ERG | 'Other' |
| | Subtypes - Tomlins | ETS+, SPINK+ | ERG+ | Triple Negative |
| | Pathway signatures | AR-V, ES, PTEN, PRF, EZH2, NE | AR, FOXA1, SPOP, ERG | PRC, RAS, PN, MES |
| | Cell Lineage | Luminal-like | Luminal-like | Basal-like |
| Patient CTCs | Proportion | 16% | 84% | 0% |
| | Enzalutamide resistance | Yes (58%) | No (8%) | Unknown |

Previously published prostate cancer classifications have defined subtypes largely based on the presence or absence of genomic alterations (e.g., TMPRSS2-ERG translocations). Tumors with ERG rearrangement (ERG[b]) are overrepresented in PCS2; however, it is not the presence or absence of an ERG rearrangement that defines the PCS2 subtype, but rather ERG pathway activation features based on coordinate expression levels of genes in the pathway. Our findings provide evidence for biologically distinct forms of prostate cancer that are independent of Gleason grade, currently the gold standard for clinical decision-making. In addition, by comparing prognostic profiles between the PCS categories and the Tomlins and colleagues categories, prognostic information was evident only from the PCS classification scheme in the same cohort. Taken together, this indicates that the PCS classification is unique.

Although the current report has provided evidence that PCS classification can assign subtypes within groups of "indolent" as well as aggressive tumors, and in a wide range of preclinical models, it remains to be determined whether the PCS categories might be stable during tumor evolution in an individual patient. An interesting alternative possibility is that disease progression results in phenotypic diversification with respect to the PCS assignment. We have shown that preclinical model systems, including genetically engineered mouse models (GEMM), can be assigned with high statistical confidence to the PCS categories. We believe the simplest explanation for this finding is that these subtypes reflect distinct epigenetic features of chromatin that are potentially stable, even in the setting of genomic instability associated with advanced disease. This possibility needs to be formally tested. The human prostate cancer cell lines we evaluated could be assigned to all 3 subtypes; however, the GEMMs we tested could only be assigned to PCS1 and PCS2. This finding suggests that approximately 1 of 3 of human prostate cancers are not being modeled in widely used GEMMs. It should be feasible to generate mouse models for PCS3 through targeted genetic manipulation of pathways that are deregulated in PCS3 and through changing chromatin structure, such as by altering the activity of the PRC2 complex.

A major clinical challenge remains the early recognition of aggressive disease, in particular, due to the multifocal nature of prostate cancer (Martin N E, Mucci L A, Loda M, Depinho R A. Prognostic determinants in prostate cancer. Cancer J 2011; 17:429-37). The classification scheme we describe predicts the risk of progression to lethal prostate cancer in patients with a diagnosis of low-grade localized disease (FIG. 3G). It is possible that in these cancers, pathway activation profiles are independent of Gleason grade and that pathways indicating high risk of progression are manifested early in the disease process and throughout multiple cancer clones in the prostate. In addition to predicting the risk of disease progression, PCS subtyping might also assist with the selection of drug treatment in advanced cancer by profiling CTCs in patient blood. With the 37-gene classifier we present here, it will be possible to assign individual tumors to PCS categories in a clinical setting. This new classification method may provide novel opportunities for therapy and clinical management of prostate cancer.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method for classifying prostate cancer into subtypes and treating prostate cancer, comprising:
   a) obtaining a sample from a subject who has prostate cancer;
   b) measuring gene expression of genes in the sample from the subject, wherein the genes are STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45;
   c) detecting changes in gene expression of the genes relative to reference samples or values;
   d) determining the presence of an expression pattern of the genes associated with PCS1 subtype in the sample from the subject based on the detected changes wherein the expression pattern is an increased expression levels in STMN1, MCM4, CCNB1, CDC6, CDKN3, EZH2, TPX2, FOXM1, KIF11, HMMR, MKI67, and KNTC1 genes, and a decreased expression levels in RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45 genes;
   e) classifying the prostate cancer in the subject into the PCS1 subtype; and
   f) administering to the subject a therapeutically effective amount of one or more DNA damaging agents selected from cisplatin, PARP inhibitors, or combinations thereof, or a therapeutically effective amount of a mitotic inhibitor, or a therapeutically effective amount of doxetaxel or a salt thereof.

2. The method of claim 1, wherein the sample comprises a tissue sample or blood.

3. The method of claim 1, wherein the sample comprises prostate tissue or circulating tumor cells.

4. The method of claim 1, wherein the PCS1 subtype is resistant to enzalutamide.

5. The method of claim 1, wherein the PCS1 subtype is characterized in that it has an increased probability of progressing to metastatic disease or prostate cancer specific mortality when compared to PCS2 subtype or PCS3 subtype.

6. A method for prognosing and treating prostate cancer in a subject, comprising:
   a) obtaining a sample from the subject who has prostate cancer;
   b) measuring expression levels of genes in the sample from the subject, wherein the genes are STMN1, MCM4, CCNB1, CDC6, CDKN3, EZH2, TPX2, FOXM1, KIF11, HMMR, MKI67, KNTC1, RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45;
   c) detecting changes in the expression levels of the genes in the sample from the subject relative to reference samples or values;
   d) determining the presence of PCS1 subtype's expression pattern of the genes in the sample based on the detected changes wherein the PCS1 subtype expression pattern has increased expression levels in STMN1, MCM4, CCNB1, CDC6, CDKN3, EZH2, TPX2, FOXM1, KIF11, HMMR, MKI67, and KNTC1 genes, and decreased expression levels in RAB3B, SLC4A4, ANK3, GJB1, SLC12A2, CFD, COL6A1, PTGDS, LTBP4, SOCS3, SPEG, GABRP, PENK, SMARCD3, CLIP3, ACTC1, ASPA, COL4A6, CYP4B1, ROR2, SGCA, SLC2A5, PAGE4, ACOX2, and C16orf45 genes;
   e) prognosing the prostate cancer in the subject as having a poor clinical outcome; and
   f) administering to the subject a therapeutically effective amount of one or more DNA damaging agents selected from cisplatin, PARP inhibitors, or combinations thereof, or a therapeutically effective amount of a mitotic inhibitor, or a therapeutically effective amount of doxetaxel or a salt of doxetaxel, or a combination thereof.

7. The method of claim 6, wherein the poor clinical outcome comprises lower metastasis-free survival, higher risk of metastatic progression, higher rate of prostate cancer specific mortality, lower overall survival, or more aggressive form of prostate cancer, or a combination thereof.

8. The method of claim 1, wherein the therapeutic agent is one or more DNA damaging agents selected from cisplatin, PARP inhibitors, or combinations thereof.

9. The method of claim 1, wherein the subtype is PCS1, and the administered therapeutic agent is a mitotic inhibitor.

10. The method of claim 1, wherein the subtype is PCS1, and the administered therapeutic agent is docetaxel, or salt of docetaxel, or a combination thereof.

11. The method of claim 1, wherein the one or more genes further comprise TOP2A, CENPF, ESRP1, SHMT2, AR, RAD54L, HN1, CELSR3, TACC3, and CCNA2.

12. The method of claim 11, wherein the subtype PSC1 and has an increased expression of TOP2A, CENPF, ESRP1, SHMT2, AR, RAD54L, HN1, CELSR3, TACC3, and CCNA2.

13. The method of claim 11, wherein the sample comprises circulating tumor cells.

14. The method of claim 6, wherein the therapeutic agent is one or more DNA damaging agents selected from cisplatin, PARP inhibitors, or combinations thereof.

15. The method of claim 6, wherein the subtype is PCS1, and the administered therapeutic agent is a mitotic inhibitor.

16. The method of claim 6, wherein the subtype is PCS1, and the administered therapeutic agent is docetaxel, or salt of docetaxel, or a combination thereof.

* * * * *